US012534529B1

(12) United States Patent
Watkins et al.

(10) Patent No.: US 12,534,529 B1
(45) Date of Patent: Jan. 27, 2026

(54) PTK7-BINDING PROTEINS

(71) Applicant: Solve Therapeutics, Inc., San Diego, CA (US)

(72) Inventors: Jeffry D. Watkins, Encinitas, CA (US); Andrew Pow, Encinitas, CA (US); Brian Lannutti, Solana Beach, CA (US); Katti Jessen, San Diego, CA (US)

(73) Assignee: Solve Therapeutics, Inc., San Diego, CA (US)

( * ) Notice: Subject to any disclaimer, the term of this patent is extended or adjusted under 35 U.S.C. 154(b) by 0 days.

(21) Appl. No.: 19/175,619

(22) Filed: Apr. 10, 2025

Related U.S. Application Data

(60) Provisional application No. 63/722,437, filed on Nov. 19, 2024.

(51) Int. Cl.
*C07K 16/28* (2006.01)

(52) U.S. Cl.
CPC ...... *C07K 16/2803* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,222,375 | B2 | 7/2012 | Terrett et al. |
| 9,102,738 | B2 * | 8/2015 | Terrett .................... A61P 35/00 |
| 9,409,995 | B2 | 8/2016 | Foord et al. |
| 9,505,845 | B2 | 11/2016 | Terrett et al. |
| 9,777,070 | B2 | 10/2017 | Damelin et al. |
| 9,914,784 | B2 | 3/2018 | Foord et al. |
| 10,836,831 | B2 | 11/2020 | Foord et al. |
| 2020/0140815 | A1 | 5/2020 | Terrett et al. |

FOREIGN PATENT DOCUMENTS

| | | | |
|---|---|---|---|
| EP | 2675827 | B1 | 8/2020 |
| EP | 3137114 | B1 | 12/2020 |

* cited by examiner

*Primary Examiner* — Daniel E Kolker
*Assistant Examiner* — James Ryland Melchior
(74) *Attorney, Agent, or Firm* — Steptoe LLP; Z. Ying Li; Debashree Chatterjee

(57) ABSTRACT

The present disclosure provides recombinant proteins that bind to PTK7 and methods of using them to treat cancer.

28 Claims, 21 Drawing Sheets

Specification includes a Sequence Listing.

Heavy Chain CDR Definitions

| Definition | HCDR1 | SEQ | HCDR2 | SEQ | HCDR3 | SEQ |
|---|---|---|---|---|---|---|
| Kabat | TYWMH | 149 | EIDPSDSYTTYNQKFTG | 155 | PAWFGY | 160 |
| Chothia | GYTFTTY | 150 | DPSDSY | 156 | PAWFGY | 160 |
| IMGT | GYTFTTYW | 151 | IDPSDSYT | 157 | LLPAWFGY | 161 |
| North/Aho | KASGYTFTTYWMH | 152 | EIDPSDSYTT | 158 | LLPAWFGY | 161 |
| Contact | TTYWMH | 153 | WIGEIDPSDSYTT | 159 | LLPAWFG | 162 |
| Grafted Seq. | GYTFTTYWMH | 154 | EIDPSDSYTTYNQKFTG | 155 | LLPAWFGY | 161 |

Light Chain CDR Definitions

| Definition | LCDR1 | SEQ | LCDR2 | SEQ | LCDR3 | SEQ |
|---|---|---|---|---|---|---|
| Kabat | RASQEISGYLS | 163 | AASTLDS | 166 | LQYATYPFT | 170 |
| Chothia | RASQEISGYLS | 163 | AASTLDS | 166 | LQYATYPFT | 170 |
| IMGT | QEISGY | 164 | AAS | 167 | LQYATYPFT | 170 |
| North/Aho | RASQEISGYLS | 163 | YAASTLDS | 168 | LQYATYPFT | 170 |
| Contact | SGYLSWL | 165 | RLIYAASTLD | 169 | LQYATYPF | 171 |
| Grafted Seq. | RASQEISGYLS | 163 | AASTLDS | 166 | LQYATYPFT | 170 |

FIG. 9A

```
1832
IGHV1-46*01         V S   VK       V                 R A       M
CDR graft       QVQLVQSGAEVKKPGASVKVSCKAS GYTFTTYWMH WVRQAPGQGLEWMG EIDPSDSYTTYNQKFTG
Back Mutations                     *                             *

18327 VH        KATLTVDTSSSTAYMQLSSLTSEDSAVYFC LLPAWFGY WGQGTLVTVSA
IGHV1-46*01     RV M R   T  V  E    R   T   Y                     S
CDR graft       RVTMTRDTSTSTVYMELSSLRSEDTAVYYC LLPAWFGY WGQGTLVTVSS
Back Mutations     * *      *               *

18327 VL        DIQMTQSPSSLSASLGERVSLTC RASQEISGYLS WLQQKPDGTIKRLIY AASTLDS
IGKV1D-16*01                  V D  TI                Y    EKAP S
CDR graft       DIQMTQSPSSLSASVGDRVTITC RASQEISGYLS WYQQKPEKAPKSLIY AASTLDS
Back Mutations                      *                *      *  *

18327 VL        GVPKRFSGSRSGSDYSLTISSLESEDFANYYC LQYATYPFT FGSGTKLEIK
IGKV1D-16*01       S     G  T FT      QP    T                  Q
CDR graft       GVPSRFSGSGSGTDFTLTISSLQPEDFATYYC LQYATYPFT FGQGTKLEIK
Back Mutations           *  * *
```

FIG. 9B

| Variant ID | VH FR Mutations | SEQ | VL FR Mutations | SEQ |
|---|---|---|---|---|
| ch18327 | Not applicable (mVH) | 76 | Not applicable (mVL) | 75 |
| Z1 | None (CDR graft) | 172 | None (CDR graft) | 183 |
| Z2 | None (CDR graft) | 172 | S46R | 184 |
| Z3 | None (CDR graft) | 172 | S46R + Y36L | 185 |
| Z4 | R71V | 173 | S46R + Y36L | 185 |
| Z5 | V78A | 174 | S46R + Y36L | 185 |
| Z6 | Y91F | 175 | S46R + Y36L | 185 |
| Z7 | Y91F + R71V | 176 | S46R + Y36L | 185 |
| Z8 | Y91F + V78A | 177 | S46R + Y36L | 185 |
| Z9 | Y91F + R71V + V78A | 178 | S46R + Y36L | 185 |
| Z10 | Y91F + R71V + V78A | 178 | S46R + Y36L + G66R | 186 |
| Z11 | Y91F + R71V + V78A | 178 | S46R + Y36L + F71Y | 187 |
| Z12 | Y91F + R71V + V78A | 178 | S46R + Y36L + G66R + F71Y | 188 |
| Z13 | Y91F + R71V + V78A + M48I | 179 | S46R + Y36L + G66R + F71Y | 188 |
| Z14 | Y91F + R71V + V78A + M69L | 180 | S46R + Y36L + G66R + F71Y | 188 |
| Z15 | Y91F + R71V + V78A + M48I + M69L | 181 | S46R + Y36L + G66R + F71Y | 188 |
| Z16 | Y91F + R71V + V78A + M48I + M69L | 181 | S46R + Y36L + G66R + F71Y + A43T | 189 |
| Z17 | Y91F + R71V + V78A + M48I + M69L | 181 | S46R + Y36L + G66R + F71Y + T69S | 190 |
| Z18 | Y91F + R71V + V78A + M48I + M69L | 181 | S46R + Y36L + G66R + F71Y + A43T + T69S | 191 |
| Z19 | Y91F + R71V + V78A + M48I + M69L + V20L | 182 | S46R + Y36L + G66R + F71Y + A43T + T69S | 191 |
| Z20 | Y91F + R71V + V78A + M48I + M69L + V20L | 182 | S46R + Y36L + G66R + F71Y + A43T + T69S + I21L | 192 |
| Z21 | Y91F + R71V + V78A + M48I + M69L + V20L | 182 | NA (mVL) | 75 |
| Z22 | NA (mVH) | 76 | S46R + Y36L + G66R + F71Y + A43T + T69S + I21L | 192 |

FIG. 9C

| ID | VH FR Mutations | SEQ ID | VL FR Mutations | SEQ ID |
|---|---|---|---|---|
| **Z12** | Y91F + R71V + V78A | 178 | S46R + Y36L + G66R + F71Y | 188 |
| **Z23** | R71V + V78A | 193 | S46R + Y36L + G66R + F71Y | 188 |
| **Z24** | Y91F + R71V + V78A | 178 | S46R + Y36L + G66R | 186 |
| **Z25** | R71V + V78A | 193 | S46R + Y36L + G66R | 186 |
| **Z26** | R71V | 173 | S46R + Y36L + G66R | 186 |
| **Z27** | R71V | 174 | Y36L + G66R | 194 |
| **Z28** | Y91F + R71V | 176 | S46R + Y36L + G66R | 186 |
| **Z29** | Y91F + R71V | 176 | S46R + Y36L + G66R + F71Y | 188 |
| **Z30** | Y91F + R71V | 176 | Y36L + G66R | 194 |
| **Z31** | R71V | 173 | S46R + Y36L + G66R + F71Y | 188 |
| **Z32** | R71V | 173 | Y36L + G66R + F71Y | 195 |
| **Z33** | R71V + V78A + M69L | 196 | S46R + Y36L + G66R + F71Y | 188 |
| **Z34** | R71V + M69L | 197 | S46R + Y36L + G66R + F71Y | 188 |

FIG. 9D

| | Freeze/ Thaw Cycles | Z12 | | | Z23 | | | Z31 | | |
|---|---|---|---|---|---|---|---|---|---|---|
| Protein Concentration (mg/mL) | 0 | 0.99 | | | 1.05 | | | 1.03 | | |
| | 5 | 0.99 | | | 1.02 | | | 1.00 | | |
| Purity (SEC-HPLC) | | HMW % | Mono % | LMW % | HMW % | Mono % | LMW % | HMW % | Mono % | LMW % |
| | 0 | 1.0 | 99.0 | 0 | 0.7 | 99.3 | 0 | 0.8 | 99.2 | 0 |
| | 5 | 1.0 | 99.0 | 0 | 0.6 | 99.4 | 0 | 0.8 | 99.2 | 0 |
| Charge Variants (iCIEF) | | Acidic % | Main % | Basic % | Acidic % | Main % | Basic % | Acidic % | Main % | Basic % |
| | 0 | 11.7 | 76.0 | 12.3 | 11.9 | 74.2 | 13.9 | 12.3 | 73.0 | 14.6 |
| | 5 | 12.1 | 75.3 | 12.6 | 12.1 | 74.2 | 13.8 | 12.4 | 73.8 | 13.8 |

FIG. 17

| | Temp. | Z12 | | | Z23 | | | Z31 | | |
|---|---|---|---|---|---|---|---|---|---|---|
| Protein Concentration (mg/mL) | 4°C | 1.02 | | | 1.06 | | | 1.02 | | |
| | 40°C | 1.03 | | | 1.06 | | | 1.02 | | |
| Purity (SEC-HPLC) | | HMW % | Mono % | LMW % | HMW % | Mono % | LMW % | HMW % | Mono % | LMW % |
| | 4°C | 1.0 | 99.0 | 0 | 0.6 | 99.4 | 0 | 0.7 | 99.3 | 0 |
| | 40°C | 1.0 | 97.6 | 1.4 | 0.6 | 98.0 | 1.4 | 0.8 | 97.8 | 1.4 |
| Charge Variants (iCIEF) | | Acidic % | Main % | Basic % | Acidic % | Main % | Basic % | Acidic % | Main % | Basic % |
| | 4°C | 11.7 | 75.1 | 13.2 | 12.1 | 73.7 | 14.1 | 11.7 | 73.1 | 15.1 |
| | 40°C | 23.5 | 62.9 | 13.6 | 24.4 | 60.8 | 14.8 | 24.0 | 59.2 | 16.9 |

FIG. 18

PTK7-BINDING PROTEINS

CROSS REFERENCE TO RELATED APPLICATIONS

This application claims priority to U.S. Provisional Patent Application 63/722,437, filed Nov. 19, 2024, the disclosure of which is incorporated by reference herein in its entirety.

SEQUENCE LISTING

The instant application contains a Sequence Listing which has been submitted electronically in XML format and is part of the specification, and is hereby incorporated by reference herein in its entirety. The electronic copy of the Sequence Listing, created on Apr. 7, 2025, is named 122878.US016.xml and is 320,717 bytes in size.

BACKGROUND OF THE INVENTION

Protein tyrosine kinase 7 (PTK7), also known as colon carcinoma kinase 4 (CCK4), is a receptor tyrosine kinase involved in non-canonical Wnt signaling and was first identified as a gene upregulated in colon cancer cells. PTK belongs to the Wnt ligand binding receptor family whose other members include receptor tyrosine kinase-like orphan receptors 1 (ROR1) and 2 (ROR2), and receptor tyrosine kinase RYK. Members of this receptor family are transmembrane proteins that are void of kinase activity. PTK7 plays roles in embryonic development, maintenance of tissue homeostasis, and stem cell signaling; however, expression of PTK7 is absent or minimal in differentiated healthy adult tissues. Overexpression of PTK7 has been reported in a variety of cancers including head and neck cancer, non-small cell lung cancer (NSCLC), triple-negative breast cancer (TNBC), bladder cancer, and ovarian cancer. In this milieu, PTK7 promotes cell survival, migration, and invasion, and chemotherapy resistance.

PTK7 expression has been associated with poor prognosis and higher metastatic potential in patients with various cancers, and thus represents a promising therapeutic target. In view of PTK7's critical role in tumor progression, there is a need for new and improved cancer immunotherapies that target PTK7.

SUMMARY OF THE INVENTION

The present disclosure provides recombinant proteins that bind specifically to PTK7. In some embodiments, the present PTK7-binding protein is an anti-PTK7 antibody or an antigen-binding portion thereof.

In some embodiments, the anti-PTK7 antibody or antigen-binding portion thereof comprises heavy chain CDR (HCDR) 1-3 and light chain CDR (LCDR) 1-3 comprising SEQ ID NOs: 151, 157, 161, 164, 167, and 170, respectively. In some embodiments, the anti-PTK7 antibody or antigen-binding portion thereof comprises a heavy chain variable domain ($V_H$) and a light chain variable domain ($V_L$) comprising SEQ ID NOs: 76 and 75, respectively.

In some embodiments, the anti-PTK7 antibody or antigen-binding portion thereof comprises a $V_H$ that comprises SEQ ID NOs: 154, 155, and 161, and a $V_L$ that comprises SEQ ID NOs: 163, 166, and 170. In some embodiments, the anti-PTK7 antibody or antigen-binding portion is humanized. In certain embodiments, the anti-PTK7 antibody or antigen-binding portion thereof comprises a $V_H$ that comprises framework regions derived from a human IGHV1-46*01 germline gene. The $V_H$ may, for example, comprise one or more back mutations selected from Y91F, R71V, V78A, M481, M69L, and V20L, wherein the numbering is according to SEQ ID NO:172. In certain embodiments, additionally or alternatively, the anti-PTK7 antibody or antigen-binding portion thereof comprises a $V_L$ that comprises framework regions derived from a human IGKVID-16*01 germline gene. The $V_L$ may, for example, comprise one or more back mutations selected from I21L, Y36L, A43T, S46R, G66R, T69S, and F71Y, wherein the numbering is according to SEQ ID NO: 183.

In some embodiments, the anti-PTK7 antibody or antigen-binding portion thereof comprises a) a $V_H$ that comprises any one of SEQ ID NOs: 172-182, 193, 196, and 197, or an amino acid sequence that is at least 95% identical thereto;

b) a $V_L$ that comprises any one of SEQ ID NOs: 183-192, 194, and 195, or an amino acid sequence that is at least 95% identical thereto; or c) a) and b).

In particular embodiments, the anti-PTK7 antibody or antigen-binding portion thereof comprises a $V_H$ and $V_L$ that comprise SEQ ID NOs: 178 and 188, respectively, SEQ ID NOs: 193 and 188, respectively, or SEQ ID NOs: 173 and 188, respectively.

In some embodiments, the anti-PTK7 antibody or antigen-binding portion thereof, the antibody comprises a human $IgG_1$ constant region. The human $IgG_1$ constant region may comprise, for example, SEQ ID NO:201, optionally without the C-terminal lysine. In some embodiments, additionally or alternatively, the anti-PTK7 antibody or antigen-binding portion thereof comprises a human light chain constant region that comprises SEQ ID NO: 199.

The present disclosure also provides an isolated anti-PTK7 antibody comprising a heavy chain that comprises the amino acid sequences of SEQ ID NOs: 193 and 201, optionally without the C-terminal lysine, and a light chain that comprises the amino acid sequences or SEQ ID NOs: 188 and 199.

The present disclosure also provides an isolated anti-PTK7 antibody that comprises a) HCDR1-3 and LCDR1-3 comprising SEQ ID NOs: 204, 209, 213, 216, 219, and 222, respectively;

b) $V_H$ and $V_L$ comprising SEQ ID NOs: 112 and 111, respectively; or c) an HC comprising SEQ ID NOs: 112 and 201, optionally without the C-terminal lysine, and an LC comprising SEQ ID NOs: 111 and 199.

The present disclosure also provides an isolated anti-PTK7 antibody that comprises a) HCDR1-3 and LCDR1-3 comprising SEQ ID NOs: 226, 231, 235, 238, 241, and 244, respectively;

b) $V_H$ and $V_L$ comprising SEQ ID NOs: 128 and 127, respectively; or c) an HC comprising SEQ ID NOs: 128 and 201, optionally without the C-terminal lysine, and an LC comprising SEQ ID NOs: 127 and 199.

In some embodiments, the isolated anti-PTK7 antibody or antigen-binding portion thereof is conjugated to a cytotoxin or a detectable label.

The present disclosure also provides pharmaceutical compositions comprising an anti-PTK7 antibody or antigen-binding portion thereof as described herein and a pharmaceutically acceptable excipient.

The present disclosure also provides nucleic acid molecule(s) encoding an anti-PTK7 antibody or antigen-binding portion thereof as described herein, as well as expression vector(s) comprising the nucleic acid molecule(s) and recombinant host cells comprising the expression vector(s). Also provided is a method of making an anti-PTK7 antibody or an antigen-binding portion thereof, comprising:

culturing a recombinant host cell described herein under conditions that allow expression of the antibody or portion, and isolating the antibody or portion from the cell culture.

The present disclosure also provides a method of treating a PTK7-positive cancer in a patient in need thereof (e.g., a human patient), comprising administering to the patient an anti-PTK7 antibody or antigen-binding portion thereof described herein or a pharmaceutical composition described herein. Also provided are use of an anti-PTK7 antibody or antigen-binding portion thereof described herein for the manufacture of a medicament for treating a PTK7-positive cancer in a patient in need thereof, or an anti-PTK7 antibody or antigen-binding portion thereof described herein or a pharmaceutical composition described herein for use in treating a PTK7-positive cancer in a patient in need thereof. In certain embodiments, the PTK7-positive cancer is selected from head and neck cancer, non-small cell lung cancer, small-cell lung cancer, breast cancer, cervical cancer, endometrial cancer, ovarian cancer, and sarcoma.

Other features, objectives, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTION OF THE FIGURES

FIG. 9A is a pair of tables showing different definitions of CDRs for antibody SLX-1040. SEQ: SEQ ID NO. Grafted Seq.: sequence grafted to human acceptor frameworks during humanization.

FIG. 9B is a sequence alignment of the heavy and light chain variable domains of antibody SLX-1040 ("18327") (SEQ ID NOs: 76 and 75, respectively) with the most homologous human heavy and light chain germline sequences (IGHV1-46*01 and IGKVID-16*01, respectively) (CDR graft sequences shown in SEQ ID NOs: 172 and 183, respectively). CDRs to be grafted to human acceptor sequences for humanization are in boldface. Asterisks indicate potential positions for making back mutations during humanization.

FIGS. 9C and 9D are tables showing humanized versions of SLX-1040 with various combinations of $V_H$ and $V_L$ variants having the indicated framework back mutations. SEQ: SEQ ID NO.

FIG. 17 is a table showing molecular stability data of antibody variants after freeze/thaw cycles.

FIG. 18 is a table showing molecular stability data of antibody variants after thermal stress.

DETAILED DESCRIPTION OF THE INVENTION

Figure 1:
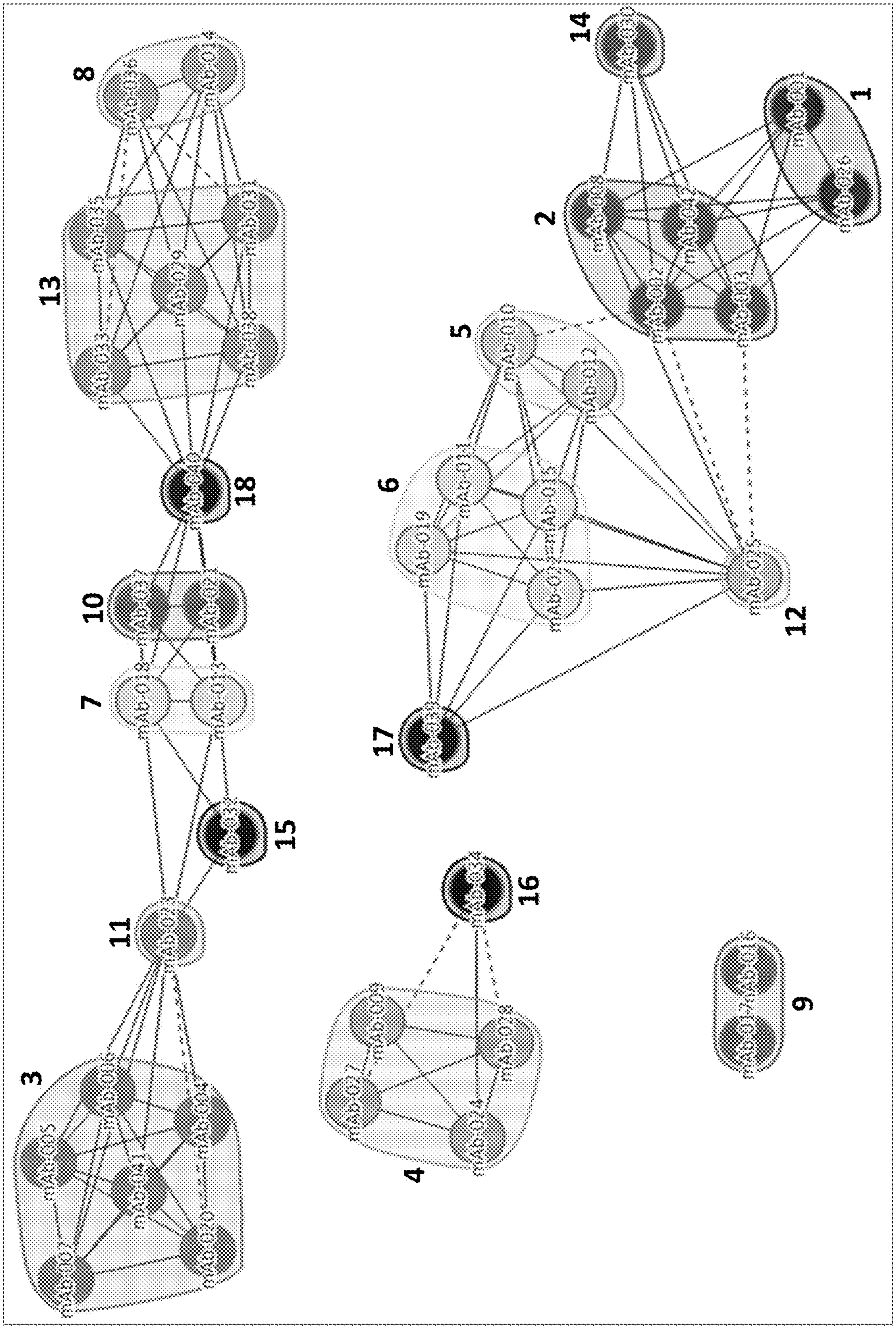
FIG. 1 shows an overview of the epitope groups (epitope bins) identified by binding competition analysis of a panel of 42 anti-PTK7 antibodies. Antibodies connected by black lines indicate cross blocking activity in both orientations (ligand and analyte). Antibodies connected by dashed lines indicate unidirectional blocking (antibody is blocked when tested as an analyte only, for example). Antibodies are grouped according to competition patterns with other anti-PTK7 antibodies. The antibodies are separated into four major groupings and are further are categorized into eighteen communities (shaded outlines).

The present disclosure provides novel proteins that specifically bind to PTK7 ("PTK7-binding proteins"). These proteins may be antibodies or comprise antigen-binding portions thereof. The proteins can be used to treat cancer (e.g., PTK7-positive cancer) in patients in need thereof.

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain ($V_H$) and a heavy chain constant region (CH). Each light chain is composed of a light chain variable domain ($V_L$) and a light chain constant region (CL). The $V_H$ and $V_L$ domains can be subdivided further into regions of hypervariability, termed "complementarity determining regions" (CDRs), interspersed with regions that are more conserved, termed "framework regions" (FRs). Each $V_H$ and $V_L$ is composed of three CDRs (HCDR herein designates a CDR from the heavy chain; and LCDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers, and of FR and CDR regions, in the heavy or light chain may be in accordance with IMGT® definitions (Lefranc et al., *Dev Comp Immunol.* (2003) 27 (1): 55-77); or the definitions of Kabat, *Sequences of Proteins of Immunological Interest* (National Institutes of Health, Bethesda, MD (1987 and 1991)); Chothia & Lesk, *J Mol Biol.* (1987) 196:901-17; Chothia et al., *Nature* (1989) 342:878-83; Abhinandan et al., *Molecular Immunology* (2008) 45(14):3832-39; MacCallum et al., *J Mol Biol.* (1996) 262:732-45; or Honegger and Plückthun, *J Mol Biol.* (2001) 309 (3): 657-70. The CDR boundaries of various schemes are illustrated in Table 1, where the amino acid numbers are Kabat numbers unless otherwise indicated.

TABLE 1

CDR Delineations According to Various Schemes

| CDR | Kabat | AbM | Chothia | Contact |
|---|---|---|---|---|
| VL-CDR1 | L24-L34 | L24-L34 | L26-L32 | L30-L36 |
| VL-CDR2 | L50-L56 | L50-L56 | L50-L52 | L46-L55 |
| VL-CDR3 | L89-L97 | L89-L97 | L91-L96 | L89-L96 |
| VH-CDR1 (Kabat nos.) | H31-H35B | H26-H35B | H26-H32 | H30-H35B |
| VH-CDR1 (Chothia nos.) | H31-H35 | H26-H35 | H26-H32 | H30-H35 |
| VH-CDR2 | H50-H65 | H50-H58 | H53-H55 | H47-H58 |
| VH-CDR3 | H95-H102 | H95-H102 | H95-H101 | H93-H101 |

The term "recombinant antibody" or "recombinant protein" refers to a non-naturally occurring antibody or protein that is expressed from a cell or cell line comprising nucleotide sequence(s) that encode the antibody or protein, wherein said nucleotide sequence(s) are not naturally associated with the cell.

The term "isolated protein," "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ for the binding is ≤1 μM, e.g., =100 nM or =10 nM. A $K_D$ binding affinity constant can be measured, e.g., by surface plasmon resonance (Biacore™) using the Biacore™ system, the IBIS MX96 SPR system from IBIS Technologies or the Carterra LSA SPR platform, or by Bio-Layer Interferometry, for example using the Octet™ system from ForteBio.

The term "epitope" as used herein refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (e.g., an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., PTK7) or a relevant portion thereof, then screening for binding to the epitope. An antibody to a particular epitope also may be generated using phage display methods.

One can determine whether an antibody binds to the same epitope as or competes for binding with an anti-PTK7 antibody of the invention by using methods known in the art, including, without limitation, competition assays, epitope binning, and alanine scanning. In one embodiment, one allows the anti-PTK7 antibody of the invention to bind to PTK7 under saturating conditions, and then measures the ability of the test antibody to bind to PTK7. If the test antibody is able to bind to PTK7 at the same time as the reference anti-PTK7 antibody, then the test antibody binds to a different epitope than the reference anti-PTK7 antibody. However, if the test antibody is not able to bind to PTK7 at the same time, then the test antibody binds to the same epitope, an overlapping epitope, or an epitope that is in close proximity to the epitope bound by the anti-PTK7 antibody of the invention. This experiment can be performed using, e.g., ELISA, RIA, Biacore™, SPR, Bio-Layer Interferometry or flow cytometry. To test whether an anti-PTK7 antibody cross-competes with another anti-PTK7 antibody, one may use the competition method described above in two directions, i.e., determining if the known antibody blocks the test antibody and vice versa. Such cross-competition experiments may be performed, e.g., using an IBIS MX96 or Carterra LSA SPR instrument or the Octet™ system.

The term "antigen-binding portion" of an antibody (or simply "antibody portion"), as used herein, refers to one or more portions or fragments of an antibody that retain the ability to specifically bind to an antigen (e.g., human PTK7, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the $V_L$, $V_H$, CL and CHI domains; (ii) a F(ab')2 fragment: a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated complementarity determining region (CDR) capable of specifically binding to an antigen. Furthermore, although the two domains of the Fv fragment, VL and VH, are encoded by separate genes, they can be joined, using recombinant methods, by a synthetic linker that enables them to be made as a single protein chain in which the VL and VH domains pair to form monovalent molecules (known as single chain Fv (scFv)). Also within the present disclosure are antigen-binding molecules comprising a VH and/or a VL. In the case of a VH, the molecule may also comprise one or more of a CHI, hinge, CH2, or CH3 region. Such single chain antibodies are also intended to be encompassed within the term “antigen-binding portion” of an antibody. Other forms of single chain antibodies, such as diabodies, are also encompassed. Diabodies are bivalent, bi-specific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and $F(ab')_2$ fragments, can be prepared from whole antibodies using conventional techniques, such as papain or pepsin digestion of whole antibodies. Moreover, antibodies, antibody portions and immunoadhesin molecules can be obtained using standard recombinant DNA techniques, e.g., as described herein.

In some embodiments, antibodies may originate from non-human sources and have been humanized to reduce anti-antibody immune responses. The term “humanize” refers to the fact that where an antibody is wholly or partially of non-human origin (for example, a murine or chicken antibody obtained from immunization of mice or chickens, respectively, with an antigen of interest, or a chimeric antibody based on such a murine or chicken antibody), it is possible to replace certain amino acids, in particular in the framework regions and constant regions of the heavy and light chains, in order to avoid or minimize an immune response in humans. Although it is not possible to precisely predict the immunogenicity, and thereby the human anti-antibody response, of a particular antibody, non-human antibodies tend to be more immunogenic in humans than human antibodies. Antibodies of non-human origin thus can be humanized to reduce the risk of a human anti-antibody response.

Humanization typically involves modification of the framework regions of the variable domain sequences. Amino acid residues that are part of complementarity determining regions (CDRs) most often will not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ser, Asn-Thr, and Asn-Ala. When such a deamidation site, in particular Asn-Gly, is present in a CDR sequence, it may therefore be desirable to remove the site, typically by conservative substitution to remove one of the implicated residues.

The class (isotype) and subclass of anti-PTK7 antibodies may be determined by any method known in the art. In general, the class and subclass of an antibody may be determined using antibodies that are specific for a particular class and subclass of antibody. Such antibodies are available commercially. The class and subclass can be determined by ELISA or Western blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies.

The term “monoclonal antibody” or “monoclonal antibody composition” means a preparation of antibody molecules of single molecular composition, which displays a single binding specificity and affinity for a particular epitope.

Unless otherwise indicated, all antibody variable region amino acid residue numbers referred to in this disclosure are those under the Kabat numbering scheme. Eu numbering is employed for constant regions.

I. PTK7-Binding Proteins

The present disclosure provides PTK-binding proteins (e.g., anti-PTK7 antibodies and proteins comprising the antibodies or antigen-binding portions thereof). Unless otherwise stated, “PTK7” refers to human PTK7 herein. A human PTK7 polypeptide sequence is available under UniProt Accession No. Q13308 (PTK7_HUMAN) and is shown below:

```
                                        (SEQ ID NO: 198)
MGAARGSPAR PRRLPLLSVL LLPLLGGTQT AIVFIKQPSS

QDALQGRRAL LRCEVEAPGP VHVYWLLDGA PVQDTERRFA

QGSSLSFAAV DRLQDSGTFQ CVARDDVTGE EARSANASFN

IKWIEAGPVV LKHPASEAEI QPQTQVTLRC HIDGHPRPTY

QWFRDGTPLS DGQSNHTVSS KERNLTLRPA GPEHSGLYSC

CAHSAFGQAC SSQNFTLSIA DESFARVVLA PQDVVVARYE

EAMFHCQFSA QPPPSLQWLF EDETPITNRS RPPHLRRATV

FANGSLLLTQ VRPRNAGIYR CIGQGQRGPP IILEATLHLA

EIEDMPLFEP RVFTAGSEER VTCLPPKGLP EPSVWWEHAG

VRLPTHGRVY QKGHELVLAN IAESDAGVYT CHAANLAGQR

RQDVNITVAT VPSWLKKPQD SQLEEGKPGY LDCLTQATPK

PTVVWYRNQM LISEDSRFEV FKNGTLRINS VEVYDGTWYR

CMSSTPAGSI EAQARVQVLE KLKFTPPPQP QQCMEFDKEA

TVPCSATGRE KPTIKWERAD GSSLPEWVTD NAGTLHFARV

TRDDAGNYTC IASNGPQGQI RAHVQLTVAV FITFKVEPER

TTVYQGHTAL LQCEAQGDPK PLIQWKGKDR ILDPTKLGPR

MHIFQNGSLV IHDVAPEDSG RYTCIAGNSC NIKHTEAPLY

VVDKPVPEES EGPGSPPPYK MIQTIGLSVG AAVAYIIAVL

GLMFYCKKRC KAKRLQKQPE GEEPEMECLN GGPLQNGQPS

AEIQEEVALT SLGSGPAATN KRHSTSDKMH FPRSSLQPIT

TLGKSEFGEV FLAKAQGLEE GVAETLVLVK SLQSKDEQQQ

LDFRRELEMF GKLNHANVVR LLGLCREAEP HYMVLEYVDL

GDLKQFLRIS KSKDEKLKSQ PLSTKQKVAL CTQVALGMEH
```

-continued

```
LSNNRFVHKD LAARNCLVSA QRQVKVSALG LSKDVYNSEY

YHFRQAWVPL RWMSPEAILE GDFSTKSDVW AFGVLMWEVF

THGEMPHGGQ ADDEVLADLQ AGKARLPQPE GCPSKLYRLM

QRCWALSPKD RPSFSEIASA LGDSTVDSKP
```

In the above sequence, amino acids 1-30 correspond to the signal sequence; amino acids 31-704 correspond to the extracellular domain (ECD); amino acids 705-725 correspond to the transmembrane domain; and amino acids 726-1070 correspond to the intracellular domain. The PTK7 binders herein bind to the ECD of PTK7.

The present disclosure provides antibodies directed against PTK7, and antigen-binding portions thereof. One advantage of the novel anti-PTK7 antibodies of the invention is that they are able to effectively bind to tumor cells as measured by increased mean fluorescence intensity (MFI) in cells exposed to the different antibody candidates; see, e.g., Examples 4 and 11. Furthermore, the novel anti-PTK7 antibodies of the invention are able to be effectively internalized in tumor cell lines as measured by the decrease in surface bound antibody over time, as demonstrated in Examples 5 and 12.

In some embodiments, the present disclosure provides an anti-PTK7 antibody or an antigen-binding portion thereof that competes or cross-competes for binding to human PTK7 with, or binds to the same epitope of human PTK7 as, any one of SLX-1040, Z12, Z23, Z31, SLX-1042, or SLX-1059.

The present disclosure also provides an anti-PTK7 antibody or an antigen-binding portion thereof that competes or cross-competes for binding to human PTK7 with, or binds to the same epitope of human PTK7 as, an antibody comprising:

a) a heavy chain variable region ($V_H$) comprising the amino acid sequence of SEQ ID NO: 76 and a light chain variable region ($V_L$) comprising the amino acid sequence of SEQ ID NO: 75;

b) a $V_H$ comprising the amino acid sequence of SEQ ID NO:178 and a $V_L$ comprising the amino acid sequence of SEQ ID NO:188;

c) a $V_H$ comprising the amino acid sequence of SEQ ID NO: 193 and a $V_L$ comprising the amino acid sequence of SEQ ID NO:188;

d) a $V_H$ comprising the amino acid sequence of SEQ ID NO:173 and a $V_L$ comprising the amino acid sequence of SEQ ID NO:188;

c) a $V_H$ comprising the amino acid sequence of SEQ ID NO: 112 and a $V_L$ comprising the amino acid sequence of SEQ ID NO: 111; or f) a $V_H$ comprising the amino acid sequence of SEQ ID NO:128 and a $V_L$ comprising the amino acid sequence of SEQ ID NO: 127.

In some embodiments, the anti-PTK7 antibody has a heavy chain CDR1 (H-CDR1) that is or is at least 90% identical in sequence to any one of SEQ ID NO:151 or 154, e.g. at least 92% identical, such as at least 95%, 96%, 97%, 98%, or 99% identical to SEQ ID NO: 151 or 154.

In some embodiments, the anti-PTK7 antibody has a heavy chain CDR2 (H-CDR2) that is or is at least 90% identical in sequence to SEQ ID NO:155 or 157, e.g. at least 92% identical, such as at least 95%, 96%, 97%, 98%, or 99% identical to SEQ ID NO:155 or 157.

In some embodiments, the anti-PTK7 antibody has a heavy chain CDR3 (H-CDR3) that is or is at least 90% identical in sequence to SEQ ID NO:161, e.g. at least 92% identical, such as at least 95%, 96%, 97%, 98% or 99% identical to SEQ ID NO:161. In some embodiments, the anti-PTK7 antibody has a light chain CDR1 (L-CDR1)

that is or is at least 90% identical in sequence to SEQ ID NO:163 or 164, e.g. at least 92% identical, such as at least 95%, 96%, 97%, 98%, or 99% identical to SEQ ID NO:163 or 164.

In some embodiments, the anti-PTK7 antibody has a light chain CDR2 (L-CDR2) that is or is at least 90% identical in sequence to SEQ ID NO:166 or 167, e.g. at least 92% identical, such as at least 95%, 96%, 97%, 98%, or 99% identical to SEQ ID NO: 166 or 167.

In some embodiments, the anti-PTK7 antibody has a light chain CDR3 (L-CDR3) that is or is at least 90% identical in sequence to SEQ ID NO:170, e.g. at least 92% identical, such as at least 95%, 96%, 97%, 98%, or 99% identical to SEQ ID NO:170.

Any combination of the above H-CDR1, H-CDR2, H-CDR3, L-CDR1, L-CDR2, and L-CDR3 sequences is also contemplated.

In some embodiments, the anti-PTK7 antibody or antigen-binding portion of the present disclosure comprises the HCDR1-3 and LCDR1-3 amino acid sequences of any one of the antibodies exemplified herein. The assignment of CDR regions may be in accordance with any method known in the art, such as IMGT®, Kabat, Chothia, Martin, Contact, or AHo definitions, or any combination of any of these definitions (Kabat plus Chothia, for example). Examples of CDR definitions under different methods are shown below for SLX-1040 (SEQ: SEQ ID NO):

SLX-1040 HCDRs

| Definition | HCDR1 | SEQ | HCDR2 | SEQ | HCDR3 | SEQ |
|---|---|---|---|---|---|---|
| IMGT ® | GYTFTTYW | 151 | IDPSDSYT | 157 | LLPAWFGY | 161 |
| Kabat | TYWMH | 149 | EIDPSDSYTTYNQKFTG | 155 | PAWFGY | 160 |
| Chothia | GYTFTTY | 150 | DPSDSY | 156 | PAWFGY | 160 |
| AHo | KASGYTFTTYWMH | 152 | EIDPSDSYTT | 158 | LLPAWFGY | 161 |
| Contact | TTYWMH | 153 | WIGEIDPSDSYTT | 159 | LLPAWFG | 162 |

| SLX-1040 LCDRs | | | | | | |
|---|---|---|---|---|---|---|
| Definition | LCDR1 | SEQ | LCDR2 | SEQ | LCDR3 | SEQ |
| IMGT ® | QEISGY | 164 | AAS | 167 | LQYATYPFT | 170 |
| Kabat | RASQEISGYLS | 163 | AASTLDS | 166 | LQYATYPFT | 170 |
| Chothia | RASQEISGYLS | 163 | AASTLDS | 166 | LQYATYPFT | 170 |
| AHo | RASQEISGYLS | 163 | YAASTLDS | 168 | LQYATYPFT | 170 |
| Contact | SGYLSWL | 165 | RLIYAASTLD | 169 | LQYATYPF | 171 |

Thus, for example, the SLX-1040 IMGT®-defined HCDR1-3 and LCDR1-3 sequences of SEQ ID NOs: 151, 157, 161, 164, 167, and 170, respectively, may be replaced in any embodiment described herein by SEQ ID NOs: 149, 155, 160, 163, 166, and 170, respectively;

SEQ ID NOs: 150, 156, 160, 163, 166, and 170, respectively;

SEQ ID NOs: 152, 158, 161, 163, 168, and 170, respectively; or

SEQ ID NOs: 153, 159, 162, 165, 169, and 171, respectively.

Also contemplated is a set of SLX-1040 CDRs wherein each of HCDR1, HCDR2, HCDR3, LCDR1, LCDR2, and LCDR3 may individually be specified according to any of the methods for defining SLX-1040 CDRs as shown above (e.g., HCDR1 specified by the Kabat definition, HCDR2 specified by the Chothia definition, etc.). The same means for defining SLX-1040 CDRs are contemplated for any of the exemplified antibodies herein.

In some embodiments, the anti-PTK7 antibody or antigen-binding portion thereof has:

an HCDR1 selected from SEQ ID NOs: 149-154;

an HCDR2 selected from SEQ ID NOs: 155-159;

an HCDR3 selected from SEQ ID NOs: 160-162;

an LCDR1 selected from SEQ ID NOs: 163-165;

an LCDR2 selected from SEQ ID NOs: 166-169; and an LCDR3 selected from SEQ ID NOs: 170 and 171.

In some embodiments, the anti-PTK7 antibody or antigen-binding portion thereof has HCDR1-3 and LCDR1-3 comprising SEQ ID NOs: 151, 157, 161, 164, 167, and 170, respectively. In some embodiments, the anti-PTK7 antibody or antigen-binding portion has HCDR1-3 and LCDR1-3 comprising SEQ ID NOs: 154, 155, 161, 163, 166, and 170, respectively.

In some embodiments, the anti-PTK7 antibody or antigen-binding portion has HCDR1-3 and LCDR1-3 comprising SEQ ID NOs: 204, 209, 213, 216, 219, and 222, respectively.

In some embodiments, the anti-PTK7 antibody or antigen-binding portion has HCDR1-3 and LCDR1-3 comprising SEQ ID NOs: 226, 231, 235, 238, 241, and 244, respectively.

In some embodiments, the anti-PTK7 antibody or antigen-binding portion thereof has a $V_H$ that is at least 90% identical in sequence to any one of SEQ ID NOs: 76, 173, 178, and 193, e.g. at least 92% identical, such as at least 95%, 96%, 97%, 98%, or 99% identical to any one of SEQ ID NOs: 76, 173, 178, and 193. Additionally or alternatively, the anti-PTK7 antibody or antigen-binding portion thereof may have a $V_L$ that is at least 90% identical in sequence to SEQ ID NO:75 or 188, e.g. at least 92% identical, such as at least 95%, 96%, 97%, 98%, or 99% identical to SEQ ID NO:75 or 188. Any combination of these $V_H$ and $V_L$ amino acid sequences is contemplated.

In some embodiments, the $V_H$ may be any one of SEQ ID NOs: 76, 173, 178, and 193 and the $V_L$ may be SEQ ID NO:75 or 188. In some embodiments, the $V_H$ may be any one of SEQ ID NOs: 173, 178, and 193 and the $V_L$ may be SEQ ID NO:188.

In some embodiments, the antibody or portion has a $V_H$ comprising SEQ ID NO: 76 or an amino acid sequence that is at least 85%, 90%, 91%, 92%, 93%, 94%, 95%, 96%, 97%, 98%, or 99% identical thereto, and a $V_L$ comprising SEQ ID NO:75 or an amino acid sequence that is at least 85%, 90%, 91%, 92%, 93%, 94%, 95%, 96%, 97%, 98%, or 99% identical thereto. In certain embodiments, the antibody or portion has a $V_H$ and a $V_L$ comprising SEQ ID NOs: 76 and 75, respectively.

In some embodiments, the antibody or portion has a $V_H$ comprising SEQ ID NO: 178 or an amino acid sequence that is at least 85%, 90%, 91%, 92%, 93%, 94%, 95%, 96%, 97%, 98%, or 99% identical thereto, and a $V_L$ comprising SEQ ID NO:188 or an amino acid sequence that is at least 85%, 90%, 91%, 92%, 93%, 94%, 95%, 96%, 97%, 98%, or 99% identical thereto. In certain embodiments, the antibody or portion has a $V_H$ and a $V_L$ comprising SEQ ID NOs: 178 and 188, respectively.

In some embodiments, the antibody or portion has a $V_H$ comprising SEQ ID NO: 193 or an amino acid sequence that is at least 85%, 90%, 91%, 92%, 93%, 94%, 95%, 96%, 97%, 98%, or 99% identical thereto, and a $V_L$ comprising SEQ ID NO: 188 or an amino acid sequence that is at least 85%, 90%, 91%, 92%, 93%, 94%, 95%, 96%, 97%, 98%, or 99% identical thereto. In certain embodiments, the antibody or portion has a $V_H$ and a $V_L$ comprising SEQ ID NOs: 193 and 188, respectively.

In some embodiments, the antibody or portion has a $V_H$ comprising SEQ ID NO: 173 or an amino acid sequence that is at least 85%, 90%, 91%, 92%, 93%, 94%, 95%, 96%, 97%, 98%, or 99% identical thereto, and a $V_L$ comprising SEQ ID NO:188 or an amino acid sequence that is at least 85%, 90%, 91%, 92%, 93%, 94%, 95%, 96%, 97%, 98%, or 99% identical thereto. In certain embodiments, the antibody or portion has a $V_H$ and a $V_L$ comprising SEQ ID NOs: 173 and 188, respectively.

In some embodiments, the antibody or portion has a $V_H$ comprising SEQ ID NO: 112 or an amino acid sequence that is at least 85%, 90%, 91%, 92%, 93%, 94%, 95%, 96%, 97%, 98%, or 99% identical thereto, and a $V_L$ comprising SEQ ID NO:111 or an amino acid sequence that is at least 85%, 90%, 91%, 92%, 93%, 94%, 95%, 96%, 97%, 98%, or 99% identical thereto. In certain embodiments, the antibody or portion has a $V_H$ and a $V_L$ comprising SEQ ID NOs: 112 and 111, respectively.

In some embodiments, the antibody or portion has a $V_H$ comprising SEQ ID NO: 128 or an amino acid sequence that is at least 85%, 90%, 91%, 92%, 93%, 94%, 95%, 96%, 97%, 98%, or 99% identical thereto, and a $V_L$ comprising SEQ ID NO:127 or an amino acid sequence that is at least 85%, 90%, 91%, 92%, 93%, 94%, 95%, 96%, 97%, 98%, or 99% identical thereto. In certain embodiments, the antibody or portion has a $V_H$ and a $V_L$ comprising SEQ ID NOs: 128 and 127 respectively.

In some embodiments, the anti-PTK7 antibody has a heavy chain (HC) amino acid sequence comprising a $V_H$ that is or is at least 80%, 85%, 90%, 91%, 92%, 93%, 94%, 95%, 96%, 97%, 98%, or 99% identical to the amino acid sequence of SEQ ID NO:76, 173, 178, or 193 and a heavy chain constant domain (CH) that is or is at least 80%, 85%, 90%, 91%, 92%, 93%, 94%, 95%, 96%, 97%, 98%, or 99% identical to the amino acid sequence of SEQ ID NO: 201, optionally without the C-terminal lysine. Additionally or alternatively, the anti-PTK7 antibody may have a light chain (LC) amino acid sequence comprising a $V_L$ that is or is at least 80%, 85%, 90%, 91%, 92%, 93%, 94%, 95%, 96%, 97%, 98%, or 99% identical to the amino acid sequence of SEQ ID NO:75 or 188 and a light chain constant domain (CL) that is or is at least 80%, 85%, 90%, 91%, 92%, 93%, 94%, 95%, 96%, 97%, 98%, or 99% identical to the amino acid sequence of SEQ ID NO: 199. Any combination of these HC and LC amino acid sequences is also contemplated.

In some embodiments, the anti-PTK7 antibody has an HC amino acid sequence comprising a $V_H$ that is or is at least 80%, 85%, 90%, 91%, 92%, 93%, 94%, 95%, 96%, 97%, 98%, or 99% identical to the amino acid sequence of SEQ ID NO: 112 and a CH that is or is at least 80%, 85%, 90%, 91%, 92%, 93%, 94%, 95%, 96%, 97%, 98%, or 99% identical to the amino acid sequence of SEQ ID NO:201, optionally without the C-terminal lysine. Additionally or alternatively, the anti-PTK7 antibody may have an LC amino acid sequence comprising a $V_L$ that is or is at least 80%, 85%, 90%, 91%, 92%, 93%, 94%, 95%, 96%, 97%, 98%, or 99% identical to the amino acid sequence of SEQ ID NO:111 and a CL that is or is at least 80%, 85%, 90%, 91%, 92%, 93%, 94%, 95%, 96%, 97%, 98%, or 99% identical to the amino acid sequence of SEQ ID NO: 199.

In some embodiments, the anti-PTK7 antibody has an HC amino acid sequence comprising a $V_H$ that is or is at least 80%, 85%, 90%, 91%, 92%, 93%, 94%, 95%, 96%, 97%, 98%, or 99% identical to the amino acid sequence of SEQ ID NO: 128 and a heavy chain constant domain CH that is or is at least 80%, 85%, 90%, 91%, 92%, 93%, 94%, 95%, 96%, 97%, 98%, or 99% identical to the amino acid sequence of SEQ ID NO:201, optionally without the C-terminal lysine. Additionally or alternatively, the anti-PTK7 antibody may have an LC amino acid sequence comprising a $V_L$ that is or is at least 80%, 85%, 90%, 91%, 92%, 93%, 94%, 95%, 96%, 97%, 98%, or 99% identical to the amino acid sequence of SEQ ID NO: 127 and a CL, that is or is at least 80%, 85%, 90%, 91%, 92%, 93%, 94%, 95%, 96%, 97%, 98%, or 99% identical to the amino acid sequence of SEQ ID NO:199.

In some embodiments, the anti-PTK7 antibody comprises an HC amino acid sequence comprising SEQ ID NOs: 76 and 201, optionally without the C-terminal lysine, and an LC amino acid sequence comprising SEQ ID NOs: 75 and 199.

In some embodiments, the anti-PTK7 antibody comprises an HC amino acid sequence comprising SEQ ID NOs: 178 and 201, optionally without the C-terminal lysine, and an LC amino acid sequence comprising SEQ ID NOs: 188 and 199.

In some embodiments, the anti-PTK7 antibody comprises an HC amino acid sequence comprising SEQ ID NOs: 193 and 201, optionally without the C-terminal lysine, and an LC amino acid sequence comprising SEQ ID NOs: 188 and 199.

In some embodiments, the anti-PTK7 antibody comprises an HC amino acid sequence comprising SEQ ID NOs: 173 and 201, optionally without the C-terminal lysine, and an LC amino acid sequence comprising SEQ ID NOs: 188 and 199.

In some embodiments, the anti-PTK7 antibody comprises an HC amino acid sequence comprising SEQ ID NOs: 112 and 201, optionally without the C-terminal lysine, and an LC amino acid sequence comprising SEQ ID NOs: 111 and 199.

In some embodiments, the anti-PTK7 antibody comprises an HC amino acid sequence comprising SEQ ID NOs: 128 and 201, optionally without the C-terminal lysine, and an LC amino acid sequence comprising SEQ ID NOs: 127 and 199.

The anti-PTK7 antibody of the present disclosure can be an IgG, an IgM, an IgE, an IgA, or an IgD molecule, but is typically of the IgG isotype, e.g., of IgG subclass $IgG_1$, $IgG_2$, $IgG_3$ or $IgG_4$. In some embodiments, the antibody is of the isotype subclass $IgG_1$.

In some embodiments, any of the anti-PTK7 antibodies may bind to human PTK7 with an $EC_{50}$ of no more than 200 nM, for example, no more than 100, 90, 80, 70, 60, 50, 40, 30, 20, 15, 10, 5, 1, 0.5, or 0.25 nM.

In some embodiments, any of the anti-PTK7 antibodies may be internalized in cells with a loss of cell surface binding signal over time of, for example, about 85%, 80%, 75%, 70%, 65%, 60%, 55%, 50%, 45%, 40%, 35%, 30%, 25%, or 20% loss of surface binding signal.

The present disclosure also contemplates an anti-PTK7 antibody or antigen-binding portion with any combination of the above properties.

The present disclosure also encompasses PTK7-binding proteins that are variants of those specifically described herein. For example, the variants may comprise mutations that confer desired properties to the proteins, e.g., increased half-life, altered (e.g., reduced) immunogenicity in humans, and/or engineered sites for covalent or non-covalent binding to another molecule (e.g., a cytotoxic, radioactive, or detectable agent). These mutations may be introduced in the framework (FR) regions, the CDRs, or other parts of the proteins (e.g., the Ig constant regions, if the proteins contain such regions).

In some embodiments, the anti-PTK7 antibody may comprise at least one mutation in the Fc region. A number of different Fc mutations are known, where these mutations alter, e.g., the antibody's effector functions or half-life. For example, in some embodiments, the constant region of an antibody (e.g., an anti-PTK7 antibody herein) may comprise mutations that improve the therapeutic potential of the antibody, such as mutations that reduce or eliminate effector functions of the antibody. An antibody may comprise, for instance, a human $IgG_1$ constant region with the mutation L235E, "LALA" mutations (L234A/L235A), "LALAGA" mutations (L234A/L235A/G237A), "LALAGR" mutations (L234A/L235A/G236R), or "LALAPG" mutations (L234A/L235A/P329G) (Eu numbering is used when referring to constant region mutations, unless otherwise indicated). In some embodiments, the constant region may comprise L234F/L235E/P331S ("FES"), L234F/L235Q/K322Q ("FQQ"), A330S/P331S, L234A/G237A, L234A/L235A/G237A, L234A/L235A/G237A/P238S/H268A/A330S/P330S, L234A/L235E, G236R/L328R, or L234A/L235A/K322A mutations. The present disclosure contemplates, for instance, an anti-PTK7 antibody herein with any mutation that reduces or eliminates effector functions as described in Wilkinson et al., *PLoS One* (2021) 16 (12):e0260954. Additionally or alternatively, the human $IgG_1$ constant region may comprise, for instance, a human heavy chain constant region with the mutation P329A. In some embodiments, the monospecific or multispecific antibody herein may comprise a human $IgG_4$ constant region with the mutation L235E and/or the mutation S228P. An IgG constant region may comprise mutations that improve the serum half-life of the antibody and/or improve manufacturing and yield of the antibody.

In certain embodiments, the anti-PTK7 antibody may comprise, e.g., L234A, L235A, and/or P329A mutations (Eu numbering), wherein the mutations may appear alone or in any combination. In particular embodiments, the anti-PTK7 antibody may comprise an Fc region with all three mutations.

In some embodiments, the present PTK7 binders, such as anti-PTK7 antibodies, have higher internalization rates on tumor cells as compared to control antibodies such as Hu24. In some embodiments, the binders bind both human PTK7 and cynomolgus PKT7.

II. Making of PTK7-Binding Proteins

The PTK7-binding protein of the present disclosure may be produced recombinantly using isolated nucleic acid molecules such as expression constructs. The coding sequences for each polypeptide chain may be cloned into a single vector or cloned into separate vectors (e.g., a pair or set of vectors). The proteins may be produced in host cells, e.g., mammalian host cells, using appropriate expression constructs. Mammalian cell lines available as hosts for expression include, without limitation, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), and A549 cells. Other cell lines that may be used are insect cell lines, such as Sf9 or Sf21 cells, and yeast cell lines. In certain embodiments, the cell lines are not derived from a human embryo. Cell lines may be selected based on their expression levels.

Host cells used to produce the PTK7-binding proteins are "recombinant host cells." A "recombinant host cell" (or simply "host cell"), as used herein, means a cell into which a recombinant expression construct has been introduced. By definition, a recombinant host cell does not occur in nature. A protein produced from a recombinant host cell is a recombinant protein.

The PTK7-binding protein may be isolated and purified from the host cell culture using well known methods, such as centrifugation; ultracentrifugation; protein A, protein G, protein A/G, or protein L purification; and/or ion exchange chromatography.

III. Pharmaceutical Compositions

Another aspect of the present disclosure is a pharmaceutical composition comprising as an active ingredient (or as the sole active ingredient) the PTK7-binding protein of the present disclosure. The pharmaceutical composition may additionally comprise a pharmaceutically acceptable excipient. A "pharmaceutically acceptable excipient" may include appropriate solvents, dispersion media, antibacterial and antifungal agents, isotonic agents, and the like. Examples of pharmaceutically acceptable excipients are water and saline (e.g., phosphate-buffered saline).

The pharmaceutical compositions may be used to treat PTK7-associated diseases, e.g., diseases where PTK7 is overexpressed. In some embodiments, the pharmaceutical compositions are intended for amelioration, prevention, and/or treatment of a PTK7-related disorder and/or cancer. As used herein, a PTK7-related or -mediated disorder refers to a disorder, disease or condition that improves, or slows down in its progression, by modulation of PTK7 activity. In some embodiments, the compositions are intended for activation of the immune system. In certain embodiments, the compositions are intended for amelioration, prevention, and/or treatment of cancer originating in tissues such as skin, lung, intestine, colon, ovary, brain, prostate, kidney, bones, soft tissues, the hematopoietic system, head and neck, liver, bladder, breast, stomach, cervical, endometrial, uterus, gastric, esophageal, and pancreas. In certain embodiments, the cancer is breast cancer. In certain embodiments, the cancer is triple-negative breast cancer (TNBC). In certain embodiments, the cancer is non-small-cell lung carcinoma (NSCLC). In certain embodiments, the cancer is small-cell lung carcinoma. In certain embodiments, the cancer is bladder cancer. In certain embodiments, the cancer is cervical cancer. In certain embodiments, the cancer is ovarian cancer. In certain embodiments, the cancer is endometrial cancer. In certain embodiments, the cancer is colon cancer. In certain embodiments, the cancer is sarcoma. In certain embodiments, the cancer is gastric cancer. In certain embodiments, the cancer is esophageal cancer. The cancer may be, e.g., at an early, intermediate, late, locally advanced, or metastatic stage, and may be relapsed or refractory to other therapeutics, or there may be no standard therapy available.

"Treat," "treating," and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. In some embodiments, therapeutic use of an antibody or antigen-binding portion thereof described herein will result in delayed tumor growth, elimination of cancer cells, tumor shrinkage/regression, increased survival, slowed or decreased metastasis, or other clinical endpoints desired by healthcare professionals. In certain embodiments, therapeutic use of an antibody or antigen-binding portion thereof described herein inhibits tumor growth by at least 10, 20, 30, 40, 50, 60, 70, 80, 90, or 100%. In certain embodiments, therapeutic use of an antibody or antigen-binding portion thereof described herein provides partial tumor regression of at least 10, 20, 30, 40, 50, 60, 70, 80, or 90%, or complete tumor regression.

The PTK7-binding proteins of the present disclosure may be administered without additional therapeutic treatments, i.e., as a stand-alone therapy (monotherapy). Alternatively, treatment with the PTK7-binding proteins may include at least one additional therapeutic treatment (combination therapy), e.g., an anti-cancer agent (such as a chemotherapeutic agent, an anti-neoplastic agent, or an anti-angiogenic agent), or a vaccine (such as a tumor vaccine).

The PTK7-binding proteins also are useful in diagnostic processes (e.g., in vitro or ex vivo). For example, the PTK7-binding proteins can be used to detect and/or measure the level of PTK7 in a biological sample from a patient (e.g., a tumor biopsy, a tissue sample, or a blood sample). Suitable detection and measurement methods include immunological methods such as flow cytometry, enzyme-linked immunosorbent assays (ELISA), chemiluminescence assays, radioimmunoassays, and immunohistochemistry. The present disclosure further encompasses kits (e.g., diagnostic kits)

comprising the antibodies, antigen-binding portions, or binding proteins described herein.

The pharmaceutical composition may be administered to a patient (e.g., a human) in need thereof in a therapeutically effective amount. A "therapeutically effective amount" is an amount that will relieve to some extent one or more of the symptoms of the disease being treated. A therapeutically effective amount of an anti-cancer therapeutic may, for example, result in delayed cancer growth; elimination of cancer cells; tumor shrinkage; increased survival; prevented, decreased, or slowed metastasis; or other clinical endpoints desired by healthcare professionals.

The pharmaceutical compositions herein may be delivered to the patient through parenteral administration, e.g., selected from subcutaneous, intraperitoneal, intramuscular, intrasternal, intracisternal, intravenous, intraarterial, intrathecal, intraurethral, intracranial, intratumoral, and intrasynovial injection or infusions. Particular embodiments include the intravenous route (e.g., intravenous infusion) and the subcutaneous route (e.g., subcutaneous injection).

Pharmaceutical compositions of the present invention and methods for their preparation will be readily apparent to those skilled in the art. Such compositions and methods for their preparation may be found, for example, in *Remington's Pharmaceutical Sciences,* $19^{th}$ Edition (Mack Publishing Company, 1995). Pharmaceutical compositions are preferably manufactured under GMP (good manufacturing practices) conditions. A pharmaceutical composition of the present disclosure may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety, as if each individual reference were specifically and individually indicated to be incorporated by reference in its entirety. Although a number of documents are cited herein, this citation does not constitute an admission that any of these documents forms part of the common general knowledge in the art. As used herein, the term "approximately" or "about" as applied to one or more values of interest refers to a value that is similar to a stated reference value. In certain embodiments, the term refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context.

As used herein, the percent identity of two amino acid sequences (or of two nucleic acid sequences) may be obtained by, e.g., BLAST® using default parameters (available at the U.S. National Library of Medicine's National Center for Biotechnology Information website). In some embodiments, the length of a query sequence aligned for comparison purposes is at least 30% (e.g., at least 40, 50, 60, 70, 80, or 90%) of the length of the reference sequence.

According to the present disclosure, back-references in the dependent claims are meant as short-hand writing for a direct and unambiguous disclosure of each and every combination of claims that is indicated by the back-reference. Any compound disclosed herein can be used in any of the treatment methods disclosed herein, wherein the individual to be treated is as defined anywhere herein.

In order that this invention may be better understood, the following examples are set forth. These examples are for purposes of illustration only and are not to be construed as limiting the scope of the invention in any manner.

EXAMPLES

Example 1: Antibody Discovery

Immunization

Four hyperimmune mice (DiversimAb™, Abveris) were immunized with 50 µg of recombinant PTK7 extracellular domain (ECD) protein (ACROBiosystems, cat. #PT7-H52H3). Following the initial immunization, mice were boosted every 2-3 days for 7-10 additional injections. Additionally, five humanized transgenic mice (ATX-GK-mix, Alloy) were immunized with 25 ug recombinant PTK7 ECD using Complete Freund's adjuvant. Following the initial immunization, mice received 4-7 weekly boosts with 25 ug recombinant PTK7 ECD using Incomplete Freund's adjuvant.

Titer Check

Mouse serum titers were checked by ELISA assay. A high binding ELISA plate was coated with 1 μg/mL antigen overnight at 4° C. Both human PTK7-Fc tagged (R&D Systems, cat. #9799-TK-050) and cynomolgus PTK7 his-tagged (ACROBiosystems, cat. #PT7-C52h3) antigen were used. The coating material was aspirated and the wells were blocked with 2% BSA in PBS for 1 h at 25° C. The blocking material was removed and 3-fold serial dilutions of sera, beginning at 1:100, in blocking solution were added and incubated at 25° C. for 1 h. The plate was washed four times with PBS containing 0.05% Tween20 (PBST) and HRP-goat anti-mouse IgG, Fcγ-specific antibody diluted 1:20,000 in blocking solution was added and incubated at 25° C. for 45 min. The plate was washed five times with PBST and 3,3',5,5'-tetramethylbenzidine (TMB) substrate was added. The reaction was terminated with stop solution and the plate was read at 450 nm. Normal mouse serum (strain matched) was included as a background control. For comparison, three PTK7 control antibodies were serially diluted 3-fold, beginning at 10 μg/mL.

The serum titers were also checked for binding to cell lines expressing PTK7 (Jurkat, H520, HCC1428) or not expressing PTK7 (Ramos). Briefly, 100,000 cells were seeded per well, and subsequently, were resuspended in 100 μL of titrated serum, starting at 1:100 dilution in 2% BSA in PBS and 3-fold serially diluted for 11 points. The samples were incubated on ice for 2h, washed, were resuspended in 50 μL of secondary antibody (Alexa Fluor® 488 AffiniPure™ goat anti-mouse IgG, Fcγ fragment specific, Jackson cat. #115-545-071) and were incubated for 30 min on ice. The cells were washed and read on an iQue flow cytometer. Normal mouse serum (strain matched) was included as a background control.

Mice with signals about 10-fold above background on antigen (strain-matched normal serum) at 1:8100 dilution were used for B cell isolation. Mice that were not used for B cell isolation due to low titers continued to be immunized and serum titers were re-checked 4-5 weeks later.

Initial Screening

Following immunization, B cells were isolated from plasma, spleen and lymph nodes and single B cell screening was performed using the Beacon® Optofluidic System (Berkeley Lights). Using a multiplex assay, cells were screened for IgG secretion, binding to recombinant human PTK7 (extra-cellular domain), binding to recombinant cynomolgus PTK7 (extra-cellular domain), binding to Jurkat cells (express PTK7), and binding to Ramos cells (no PTK7 expression). Isolated B cell clones with different binding profiles were prioritized for antibody sequencing. All selected clones secreted IgG and were negative for binding to Ramos cells. Priority 1 clones were reactive with recombinant human and cynomolgus PTK7 and bound Jurkat cells. Priority 2 clones were reactive with recombinant human and bound Jurkat cells. Priority 3 clones bound Jurkat cells but were unreactive with recombinant PTK7. Complete $V_H$ and $V_L$ sequences were obtained for 73 antibodies. The antibodies isolated from Beacon® screening are summarized in Table 2. Control anti-huPTK7 antibodies 188B (Miltenyi Biotec cat. #130-091-578; mouse $IgG_{2a}$), OTI2E7 (Invitrogen cat. #MA5-25774; mouse $IgG_1$) and hu24 (U.S. Pat. No. 9,777,070; humanized murine antibody; $V_H$ and $V_L$ sequences shown in the sequence table below) are listed at the bottom of Table 2.

TABLE 2

| Discovery Campaign Antibodies | | | |
|---|---|---|---|
| Hybridoma Clone ID | Ab ID | $V_L$ SEQ ID NO | $V_H$ SEQ ID NO |
| D2D77808-440 | SLX-1001 | 23 | 24 |
| D2D77808-843 | SLX-1002 | 35 | 36 |
| D2D77808-1105 | SLX-1003 | 3 | 4 |
| D2D77808-1244 | SLX-1004 | 9 | 10 |
| D2D77808-3188 | SLX-1005 | 15 | 16 |
| D2D77808-3224 | SLX-1006 | 17 | 18 |
| D2D77808-3707 | SLX-1007 | 19 | 20 |
| D2D77808-3991 | SLX-1008 | 21 | 22 |
| D2D77808-4647 | SLX-1009 | 25 | 26 |
| D2D77808-4992 | SLX-1010 | 27 | 28 |
| D2D77808-5632 | SLX-1011 | 29 | 30 |
| D2D77808-7380 | SLX-1012 | 31 | 32 |
| D2D77808-7683 | SLX-1013 | 33 | 34 |
| D2D77808-9018 | SLX-1014 | 37 | 38 |
| D2D77808-9100 | SLX-1015 | 39 | 40 |
| D2D77808-10892 | SLX-1016 | 1 | 2 |
| D2D77808-11336 | SLX-1017 | 5 | 6 |
| D2D77808-11967 | SLX-1018 | 7 | 8 |
| D2D77808-12633 | SLX-1019 | 11 | 12 |
| D2D77808-13587 | SLX-1020 | 13 | 14 |
| D2D77812-3278 | SLX-1021 | 41 | 42 |
| D2D77812-3529 | SLX-1022 | 43 | 44 |
| D3D88750-2823 | SLX-1023 | 51 | 52 |
| D3D88750-7308 | SLX-1024 | 53 | 54 |
| D3D88750-8482 | SLX-1025 | 55 | 56 |
| D3D88750-10931 | SLX-1026 | 45 | 46 |
| D3D88750-15061 | SLX-1027 | 47 | 48 |
| D3D88750-17170 | SLX-1028 | 49 | 50 |
| D3D88936-762 | SLX-1029 | 81 | 82 |
| D3D88936-6283 | SLX-1030 | 79 | 80 |
| D3D88936-10726 | SLX-1031 | 57 | 58 |
| D3D88936-12014 | SLX-1032 | 59 | 60 |
| D3D88936-13864 | SLX-1033 | 61 | 62 |
| D3D88936-14075 | SLX-1034 | 63 | 64 |
| D3D88936-14742 | SLX-1035 | 65 | 66 |
| D3D88936-14768 | SLX-1036 | 67 | 68 |
| D3D88936-15092 | SLX-1037 | 69 | 70 |
| D3D88936-16478 | SLX-1038 | 71 | 72 |

TABLE 2-continued

| Discovery Campaign Antibodies | | | |
|---|---|---|---|
| Hybridoma Clone ID | Ab ID | $V_L$ SEQ ID NO | $V_H$ SEQ ID NO |
| D3D88936-17701 | SLX-1039 | 73 | 74 |
| D3D88936-18327 | SLX-1040 | 75 | 76 |
| D3D88936-19853 | SLX-1041 | 77 | 78 |
| D4D88750-935 | SLX-1042 | 111 | 112 |
| D4D88750-2830 | SLX-1043 | 101 | 102 |
| D4D88750-4395 | SLX-1044 | 103 | 104 |
| D4D88750-4746 | SLX-1045 | 105 | 106 |
| D4D88750-7698 | SLX-1046 | 107 | 108 |
| D4D88750-9185 | SLX-1047 | 109 | 110 |
| D4D88750-10662 | SLX-1048 | 83 | 84 |
| D4D88750-11630 | SLX-1049 | 85 | 86 |
| D4D88750-13229 | SLX-1050 | 87 | 88 |
| D4D88750-13354 | SLX-1051 | 89 | 90 |
| D4D88750-13531 | SLX-1052 | 91 | 92 |
| D4D88750-16740 | SLX-1053 | 93 | 94 |
| D4D88750-16804 | SLX-1054 | 95 | 96 |
| D4D88750-19223 | SLX-1055 | 97 | 98 |
| D4D88750-19685 | SLX-1056 | 99 | 100 |
| D4D88936-1008 | SLX-1057 | 113 | 114 |
| D4D88936-1474 | SLX-1058 | 119 | 120 |
| D4D88936-3188 | SLX-1059 | 127 | 128 |
| D4D88936-5708 | SLX-1060 | 129 | 130 |
| D4D88936-5760 | SLX-1061 | 131 | 132 |
| D4D88936-5943 | SLX-1062 | 133 | 134 |
| D4D88936-5944 | SLX-1063 | 135 | 136 |
| D4D88936-6018 | SLX-1064 | 137 | 138 |
| D4D88936-6809 | SLX-1065 | 139 | 140 |
| D4D88936-7838 | SLX-1066 | 141 | 142 |
| D4D88936-8951 | SLX-1067 | 143 | 144 |
| D4D88936-9137 | SLX-1068 | 145 | 146 |
| D4D88936-10730 | SLX-1069 | 115 | 116 |
| D4D88936-12394 | SLX-1070 | 117 | 118 |
| D4D88936-14748 | SLX-1071 | 121 | 122 |

TABLE 2-continued

| Discovery Campaign Antibodies | | | |
|---|---|---|---|
| Hybridoma Clone ID | Ab ID | $V_L$ SEQ ID NO | $V_H$ SEQ ID NO |
| D4D88936-15106 | SLX-1072 | 123 | 124 |
| D4D88936-16655 | SLX-1073 | 125 | 126 |
| 188B | | | |
| OTI2E7 | | | |
| Hu24 | SLX-1000 | 147 | 148 |

Example 2: Secondary Screening and Characterization

Initially, 48 clones were selected for further characterization and were expressed as human $IgG_1$ using Expi293 cells. The antibodies were purified in a single step using MabSelect PrismA™ protein A chromatography resin (Cytiva) and the final buffer composition was 65 mM Tris, 10 mM glycine, pH 6.0.

Binding of the antibodies to four tumor cell lines expressing PTK7 (Jurkat, NCI-H520, OVCAR3, HCC1428) and one tumor cell line not expressing PTK7 (Ramos) was assessed by flow cytometry. Jurkat is a human T lymphocyte cell line. NCI-H520 is a human non-small cell lung cancer line. OVCAR3 is a human high-grade serous ovarian adenocarcinoma cell line. HCC1428 is a human epithelial adenocarcinoma cell line. Ramos (RA-1) is a human B lymphocyte cell line.

The binding of all antibodies was tested at a single concentration (10 ug/mL). Briefly, cells were seeded at 100,000 cells per well and were resuspended in 100 μL of purified IgG at 10 μg/mL. The cells were incubated with the antibody for 30 min on ice, washed two times with 100 μL 1% BSA in PBS, washed once with 150 μL 1% BSA and were resuspended in 50 μL of Alexa Fluor® 488 AffiniPure™ goat anti-mouse IgG, Fcγ fragment specific (Jackson cat. #115-545-071) diluted in 1% BSA in PBS, and were incubated on ice for an additional 30 min. Control anti-PTK7 antibodies 188B, OTI2E7 and hu24 were also tested at 10 μg/mL. The MFI values obtained are summarized in Table 3. In general, NCI-H520 cells displayed the highest MFI values with most antibodies tested while HCC1428 cells displayed the lowest MFI values. However, certain antibodies displayed different staining patterns. For example, control antibody OTI2E7 and several discovered antibodies (e.g., D4D88936-3188, D3D88936-15092, D4D88936-1474, and D4D88750-935) displayed higher binding signals with OVCAR3 cells than with NCI-H520 cells. Several antibodies that displayed strong binding to all four tumor cell lines, but not Ramos cells, were identified (e.g., D4D88750-9185, D4D88750-11630, D4D88936-3188, D3D88936-15092, D4D88936-1474, D3D88936-18327, and D4D88750-935). Some antibodies, such as D3D88936-15092, D4D88936-3188, D3D88936-18327 and D4D88750-935, displayed superior binding to tumor cells over control antibody 188B.

TABLE 3

| Flow Cytometry Analysis of Binding to Cell Lines | | | | | |
|---|---|---|---|---|---|
| Clone | Jurkat | NCI-H520 | OVCAR3 | HCC1428 | Ramos (RA-1) |
| Unstained | 4,627 | 10,016 | 18,248 | 17,270 | 6,281 |
| Anti-mouse secondary | 4,679 | 9,408 | 15,723 | 15,344 | 6,113 |
| Anti-human secondary | 3,917 | 10,950 | 19,245 | 20,101 | 6,259 |
| 188B | 56,037 | 99,866 | 89,435 | 31,551 | 6,108 |
| OTI2E7 | 93,975 | 95,330 | 235,937 | 53,768 | 6,368 |
| Hu24 | 116,240 | 421,165 | 174,391 | 59,952 | 6,332 |
| D4D88750-9185 | 102,006 | 200,899 | 194,724 | 55,849 | 6,633 |
| D4D88750-11630 | 90,705 | 155,278 | 146,894 | 52,780 | 6,553 |
| D4D88936-3188 | 86,327 | 176,107 | 218,045 | 51,262 | 6,471 |
| D3D88936-15092 | 100,954 | 180,572 | 201,505 | 50,473 | 6,311 |
| D4D88936-1008 | 67,338 | 95,325 | 97,596 | 49,965 | 6,722 |
| D4D88936-1474 | 94,360 | 117,152 | 136,308 | 47,983 | 6,350 |
| D3D88936-18327 | 97,525 | 105,613 | 87,545 | 44,768 | 6,294 |
| D4D88750-935 | 100,667 | 131,198 | 192,578 | 44,134 | 6,458 |
| D4D88936-5943 | 25,097 | 117,264 | 76,733 | 42,122 | 6,937 |
| D4D88936-5760 | 35,563 | 112,014 | 104,024 | 41,950 | 6,527 |
| D4D88936-14748 | 58,815 | 103,718 | 105,007 | 34,440 | 6,368 |
| D4D88936-12394 | 20,629 | 99,243 | 55,731 | 32,956 | 6,343 |
| D4D88750-10662 | 15,711 | 30,210 | 35,671 | 26,823 | 6,674 |
| D4D88936-6018 | 30,066 | 145,486 | 84,557 | 24,629 | 6,519 |
| D4D88936-15106 | 21,707 | 254,492 | 97,773 | 22,764 | 6,071 |
| D4D88936-5944 | 14,784 | 84,192 | 37,295 | 22,474 | 6,281 |
| D4D88750-13531 | 12,802 | 45,349 | 35,717 | 22,310 | 6,218 |
| D4D88750-4395 | 14,080 | 101,896 | 54,521 | 21,849 | 6,417 |
| D4D88936-16655 | 9,635 | 229,222 | 57,641 | 21,611 | 6,097 |
| D4D88936-6809 | 4,666 | 116,608 | 23,619 | 21,588 | 6,070 |
| D3D88750-17170 | 4,043 | 10,986 | 16,999 | 20,964 | 6,074 |
| D3D88936-6283 | 18,446 | 130,677 | 73,488 | 20,933 | 6,744 |
| D3D88750-7308 | 4,057 | 11,033 | 17,311 | 20,685 | 6,540 |
| D3D88750-8482 | 4,048 | 10,334 | 17,709 | 20,641 | 6,372 |
| D4D88936-8951 | 4,106 | 58,339 | 19,874 | 20,584 | 6,025 |
| D4D88750-19223 | 3,950 | 87,466 | 19,027 | 20,411 | 5,950 |
| D3D88750-10931 | 3,438 | 11,034 | 17,809 | 20,371 | 6,526 |
| D4D88750-4746 | 4,074 | 55,374 | 18,818 | 20,105 | 6,399 |
| D4D88936-9137 | 4,214 | 25,699 | 19,264 | 20,060 | 6,452 |
| D3D88936-14742 | 3,674 | 134,991 | 19,469 | 20,046 | 6,141 |
| D3D88936-762 | 7,406 | 104,315 | 47,536 | 19,957 | 6,529 |
| D3D88750-15061 | 3,683 | 53,168 | 16,223 | 19,946 | 6,382 |
| D4D88936-5708 | 4,212 | 13,989 | 18,966 | 19,830 | 6,433 |
| D3D88750-2823 | 4,063 | 10,810 | 18,845 | 19,782 | 6,505 |
| D4D88750-16740 | 4,120 | 10,803 | 19,044 | 19,729 | 6,559 |
| D4D88750-2830 | 4,811 | 149,182 | 23,584 | 19,654 | 6,180 |
| D3D88936-13864 | 4,408 | 99,753 | 19,064 | 19,253 | 6,351 |
| D4D88750-16804 | 3,659 | 10,602 | 18,673 | 19,196 | 6,211 |
| D4D88750-13354 | 4,562 | 112,579 | 18,490 | 19,137 | 6,508 |
| D3D88936-10726 | 4,378 | 103,715 | 23,064 | 19,045 | 6,291 |
| D3D88936-19853 | 4,241 | 52,533 | 18,280 | 19,044 | 6,525 |
| D4D88750-7698 | 5,701 | 61,075 | 30,230 | 18,874 | 6,363 |
| D3D88936-14768 | 3,912 | 169,905 | 19,585 | 18,824 | 6,163 |
| D3D88936-14075 | 4,476 | 72,284 | 17,322 | 18,812 | 6,536 |
| D4D88750-13229 | 4,633 | 11,149 | 19,405 | 18,519 | 6,411 |
| D3D88936-16478 | 4,302 | 100,382 | 20,398 | 18,167 | 6,139 |
| D3D88936-12014 | 4,528 | 120,647 | 19,804 | 18,145 | 6,447 |
| D3D88936-17701 | 4,279 | 42,369 | 16,208 | 18,023 | 6,687 |

Twelve additional clones were selected for characterization and were expressed as human $IgG_1$ using Expi293 cells. Binding of these antibodies to the four tumor cell lines expressing PTK7 (Jurkat, NCI-H520, OVCAR3, HCC1428) and one tumor cell line not expressing PTK7 (Ramos) was assessed by flow cytometry, as described above. The MFI values obtained are summarized in Table 4. For this set of antibodies, OVCAR3 cells generally displayed the highest MFI values while HCC1428 cells displayed the lowest expression. However, similar to the first panel of antibodies tested, the antibodies displayed different relative binding patterns across the various cell lines tested. Multiple antibodies that displayed strong binding to all four tumor cell lines, but not Ramos, cells were identified (e.g., D2D77808-5632, D2D77808-3707, and D2D77808-7380).

TABLE 4

| Flow Cytometry Analysis of Binding to Cell Lines | | | | | |
|---|---|---|---|---|---|
| Clone | Jurkat | NCI-H520 | Ovcar3 | HCC1428 | Ramos (RA-1) |
| D2D77808-5632 | 136,003 | 282,973 | 504,759 | 75,622 | 8,303 |
| D2D77808-3707 | 120,159 | 336,868 | 454,008 | 75,506 | 8,080 |
| D2D77808-7380 | 118,795 | 201,294 | 415,895 | 70,713 | 8,256 |
| D2D77808-3224 | 109,424 | 214,509 | 278,387 | 58,444 | 8,689 |
| D2D77808-4647 | 106,892 | 168,953 | 346,875 | 67,855 | 8,347 |
| D2D77808-1244 | 88,336 | 244,856 | 345,695 | 65,811 | 8,045 |
| D2D77808-3188 | 69,988 | 176,043 | 222,205 | 45,054 | 8,479 |
| D2D77808-843 | 69,983 | 248,694 | 246,991 | 35,534 | 8,179 |
| D2D77812-3278 | 53,686 | 170,503 | 208,398 | 30,753 | 8,393 |
| D2D77808-9018 | 39,708 | 175,002 | 166,788 | 28,808 | 8,758 |
| D2D77812-3529 | 4,977 | 18,953 | 24,228 | 22,508 | 8,047 |
| D2D77808-440 | 4,189 | 41,187 | 26,296 | 23,764 | 8,230 |

Next, the binding kinetics of the antibodies to human and cynomolgus recombinant PTK7 was characterized using the Octet® bio-layer interferometry (BLI) platform (Sartorius). Individual anti-human biosensors were loaded with purified human IgG samples. Following establishment of the loading baseline, the sensors were exposed to human PTK7 (His-tagged, at 250 nM) and the association rates were measured. The biosensors were moved to a buffer well to measure the dissociation rate of target antigen from the immobilized antibody. The biosensors were regenerated to repeat the assay using cynomolgus PTK7. The antibodies displayed a wide range of affinities for recombinant human PTK7 (Table 5; "PF": poor fit, "NB": no detectable binding). For example, eleven antibodies had $K_D$<10 nM while eleven had $K_D$>25 nM.

TABLE 5

| Recombinant Human and Cynomolgus PTK7 Binding Kinetics | | | | | | |
|---|---|---|---|---|---|---|
| | Human PTK7-His tag | | | Cynomolgus PTK7-His tag | | |
| Clone | $K_D$ (M) | $k_a$ (1/Ms) | $k_{dis}$ (1/s) | $K_D$ (M) | $k_a$ (1/Ms) | $k_{dis}$ (1/s) |
| D3D88750-10931 | PF | N.B. | N.B. | N.B. | N.B. | N.B. |
| D3D88750-15061 | 2.58E−08 | 1.70E+05 | 4.38E−03 | 2.29E−09 | 2.79E+04 | 6.40E−05 |
| D3D88750-17170 | N.B. | N.B. | N.B. | N.B. | N.B. | N.B. |
| D3D88750-2823 | N.B. | N.B. | N.B. | N.B. | N.B. | N.B. |
| D3D88750-7308 | PF | N.B. | N.B. | N.B. | N.B. | N.B. |
| D3D88750-8482 | N.B. | N.B. | N.B. | N.B. | N.B. | N.B. |
| D3D88936-12014 | 1.70E−08 | 1.50E+05 | 2.54E−03 | 9.76E−09 | 6.91E+04 | 6.75E−04 |

TABLE 5-continued

Recombinant Human and Cynomolgus PTK7 Binding Kinetics

| Clone | Human PTK7-His tag | | | Cynomolgus PTK7-His tag | | |
|---|---|---|---|---|---|---|
| | $K_D$ (M) | $k_a$ (1/Ms) | $k_{dis}$ (1/s) | $K_D$ (M) | $k_a$ (1/Ms) | $k_{dis}$ (1/s) |
| D3D88936-13864 | 1.06E−08 | 8.30E+04 | 8.78E−04 | 6.54E−09 | 7.07E+04 | 4.62E−04 |
| D3D88936-14075 | 1.38E−08 | 6.62E+04 | 9.15E−04 | 3.53E−09 | 3.96E+04 | 1.40E−04 |
| D3D88936-14742 | 8.55E−09 | 3.32E+05 | 2.84E−03 | 5.20E−09 | 2.15E+05 | 1.12E−03 |
| D3D88936-14768 | 2.59E−08 | 1.81E+05 | 4.70E−03 | 1.09E−08 | 1.06E+05 | 1.15E−03 |
| D3D88936-15092 | 3.42E−09 | 8.66E+04 | 2.96E−04 | 3.86E−09 | 8.39E+04 | 3.24E−04 |
| D3D88936-10726 | 6.40E−09 | 1.65E+05 | 1.05E−03 | 3.88E−09 | 5.01E+04 | 1.94E−04 |
| D3D88936-16478 | 1.11E−08 | 1.47E+05 | 1.63E−03 | 3.85E−09 | 4.04E+04 | 1.56E−04 |
| D3D88936-18327 | 1.36E−09 | 4.35E+04 | 5.92E−05 | 2.89E−08 | 5.37E+04 | 1.55E−03 |
| D3D88936-19853 | N.B. | N.B. | N.B. | N.B. | N.B. | N.B. |
| D3D88936-6283 | 1.97E−08 | 1.47E+05 | 2.90E−03 | 2.44E−08 | 1.35E+05 | 3.30E−03 |
| D3D88936-762 | 1.74E−08 | 4.09E+04 | 7.13E−04 | 4.15E−09 | 3.93E+04 | 1.63E−04 |
| D4D88750-10662 | N.B. | N.B. | N.B. | N.B. | N.B. | N.B. |
| D4D88750-11630 | 4.28E−09 | 5.50E+04 | 2.36E−04 | 2.82E−09 | 5.50E+04 | 1.55E−04 |
| D4D88750-13229 | 9.67E−09 | 4.67E+04 | 4.52E−04 | 6.46E−09 | 3.21E+05 | 2.07E−03 |
| D4D88750-13531 | 2.50E−08 | 3.26E+05 | 8.15E−03 | 5.25E−08 | 2.80E+05 | 1.47E−02 |
| D4D88750-16740 | N.B. | N.B. | N.B. | N.B. | N.B. | N.B. |
| D4D88750-16804 | N.B. | N.B. | N.B. | N.B. | N.B. | N.B. |
| D4D88750-19223 | 2.73E−08 | 1.85E+05 | 5.06E−03 | N.B. | N.B. | N.B. |
| D4D88750-2830 | 2.42E−08 | 5.04E+04 | 1.22E−03 | 6.38E−09 | 3.60E+04 | 2.30E−04 |
| D4D88750-4395 | 3.45E−08 | 8.71E+04 | 3.01E−03 | 2.66E−08 | 7.65E+04 | 2.03E−03 |
| D4D88750-4746 | N.B. | N.B. | N.B. | N.B. | N.B. | N.B. |
| D4D88750-7698 | N.B. | N.B. | N.B. | N.B. | N.B. | N.B. |
| D4D88750-9185 | 2.79E−09 | 7.92E+04 | 2.21E−04 | 2.68E−09 | 5.43E+04 | 1.45E−04 |
| D4D88750-935 | 9.48E−09 | 5.00E+04 | 4.74E−04 | 5.47E−09 | 4.66E+04 | 2.55E−04 |
| D4D88936-1008 | N.B. | N.B. | N.B. | N.B. | N.B. | N.B. |
| D4D88936-12394 | 2.67E−08 | 8.46E+04 | 2.26E−03 | 1.22E−08 | 7.44E+04 | 9.09E−04 |
| D4D88936-1474 | 3.02E−09 | 5.46E+04 | 1.65E−04 | 5.75E−10 | 5.74E+04 | 3.30E−05 |
| D4D88936-14748 | 1.64E−08 | 6.69E+04 | 1.10E−03 | 8.32E−09 | 6.00E+04 | 4.99E−04 |
| D4D88936-15106 | 9.45E−08 | 4.80E+04 | 4.54E−03 | 1.31E−08 | 3.75E+04 | 4.90E−04 |
| D4D88936-16655 | 4.05E−08 | 7.46E+04 | 3.02E−03 | 2.31E−08 | 6.95E+04 | 1.60E−03 |
| D4D88936-3188 | 2.79E−09 | 9.98E+04 | 2.78E−04 | 1.64E−09 | 9.25E+04 | 1.51E−04 |
| D4D88936-5708 | 1.50E−08 | 3.36E+04 | 5.02E−04 | 1.70E−09 | 3.90E+04 | 6.62E−05 |
| D4D88936-5760 | 3.00E−08 | 7.81E+04 | 2.34E−03 | 1.35E−08 | 7.31E+04 | 9.82E−04 |
| D4D88936-5943 | N.B. | N.B. | N.B. | N.B. | N.B. | N.B. |
| D4D88936-5944 | N.B. | N.B. | N.B. | N.B. | N.B. | N.B. |
| D4D88936-6018 | 2.79E−08 | 1.34E+05 | 3.75E−03 | 1.03E−08 | 3.80E+04 | 3.92E−04 |
| D4D88936-6809 | 4.38E−08 | 7.54E+04 | 3.30E−03 | 2.78E−08 | 7.48E+04 | 2.08E−03 |
| D4D88936-8951 | 1.88E−08 | 1.92E+04 | 3.61E−04 | 1.49E−09 | 1.85E+04 | 2.76E−05 |
| D4D88936-9137 | 8.83E−09 | 2.26E+04 | 1.99E−04 | 2.69E−10 | 1.11E+03 | 2.99E−07 |
| D3D88936-17701 | 1.52E−08 | 3.94E+04 | 5.99E−04 | 4.06E−09 | 3.90E+04 | 1.58E−04 |
| D4D88750-13354 | 1.13E−08 | 3.89E+05 | 4.40E−03 | 1.26E−08 | 7.98E+04 | 1.01E−03 |
| Hu24 | 6.81E−10 | 5.20E+04 | 3.54E−05 | 9.52E−12 | 5.13E+04 | 4.88E−07 |
| 188B | 2.55E−08 | 1.20E+05 | 3.05E−03 | 3.33E−08 | 1.31E+05 | 4.35E−03 |
| OTI2E7 | 1.73E−09 | 1.07E+05 | 1.85E−04 | N.B. | N.B. | N.B. |

The binding kinetics of the second set of antibodies (n=12) to human and cynomolgus recombinant PTK7 was also characterized using the Octet® BLI platform as described above. The data show that this set of antibodies displayed a wide range of affinities for recombinant human PTK7 (Table 6). For example, five antibodies had KD <1 nM, two antibodies had $K_D$<10 nM, and five had $K_D$>10 nM.

TABLE 6

Recombinant Human and Cynomolgus PTK7 Binding Kinetics

| Clone | Human PTK7-His tag | | | Cynomolgus PTK7-His tag | | |
|---|---|---|---|---|---|---|
| | $K_D$ (M) | $k_a$ (1/Ms) | $k_{dis}$ (1/s) | $K_D$ (M) | $k_a$ (1/Ms) | $k_{dis}$ (1/s) |
| D2D77808-3707 | 1.92E−11 | 2.81E+04 | 5.39E−07 | 7.29E−08 | 3.18E+04 | 2.32E−03 |
| D2D77808-440 | 1.64E−08 | 7.68E+04 | 1.26E−03 | 7.60E−09 | 6.44E+04 | 4.90E−04 |
| D2D77808-4647 | 1.19E−09 | 3.99E+04 | 4.75E−05 | 3.07E−08 | 6.77E+04 | 2.08E−03 |
| D2D77808-9018 | 5.62E−08 | 5.52E+04 | 3.10E−03 | 5.79E−08 | 4.68E+04 | 2.71E−03 |
| D2D77812-3278 | 1.27E−08 | 1.97E+05 | 2.50E−03 | 8.18E−08 | 2.78E+04 | 2.28E−03 |
| D2D77812-3529 | 1.13E−08 | 4.42E+04 | 4.98E−04 | 1.67E−11 | 3.47E+04 | 5.78E−07 |
| D2D77808-1244 | 4.18E−10 | 4.18E+04 | 1.75E−05 | 8.40E−12 | 3.91E+04 | 3.29E−07 |
| D2D77808-3188 | 1.50E−08 | 2.62E+04 | 3.92E−04 | 6.97E−09 | 2.62E+04 | 1.83E−04 |
| D2D77808-3224 | 1.46E−11 | 1.86E+04 | 2.71E−07 | 2.17E−11 | 2.13E+04 | 4.61E−07 |
| D2D77808-5632 | 1.45E−11 | 2.55E+04 | 3.68E−07 | 6.54E−08 | 3.08E+04 | 2.01E−03 |
| D2D77808-7380 | 9.99E−12 | 2.93E+04 | 2.93E−07 | 6.43E−08 | 3.35E+04 | 2.15E−03 |
| D2D77808-843 | 5.75E−09 | 4.42E+04 | 2.54E−04 | 4.79E−09 | 3.99E+04 | 1.91E−04 |
| Hu24 | 2.81E−09 | 5.06E+04 | 1.42E−04 | 6.93E−10 | 4.90E+04 | 3.40E−05 |

TABLE 6-continued

| Recombinant Human and Cynomolgus PTK7 Binding Kinetics | | | | | | |
|---|---|---|---|---|---|---|
| | Human PTK7-His tag | | | Cynomolgus PTK7-His tag | | |
| Clone | $K_D$ (M) | $k_a$ (1/Ms) | $k_{dis}$ (1/s) | $K_D$ (M) | $k_a$ (1/Ms) | $k_{dis}$ (1/s) |
| 188B | 2.20E−08 | 1.32E+05 | 2.92E−03 | 3.56E−08 | 1.29E+05 | 4.60E−03 |
| OTI2E7 | 4.09E−10 | 1.04E+05 | 4.26E−05 | N.B | N.B | N.B |

The above data show that unlike control antibody OTI2E7, most of the new antibodies identified herein were able to bind to both human and cynomolgus PTK7. This cross-species binding feature is highly advantageous because it would allow these antibodies to be studied in non-human primates in pre-clinical toxicology studies.

Example 3: Epitope Binning

Based on tumor cell binding characteristics, thirty-nine antibodies were selected for characterization by epitope binning. To do this, all thirty-nine purified antibodies were prepared at 10 μg/mL in 10 mM sodium acetate, pH 4.5 buffer and covalently coupled to a Carterra® HC30M chip at duplicate spots using the standard EDC/NHS surface chemistry. Next, 100 nM of human PTK7-His tag was injected over the covalently coupled antibody surfaces followed by the injection of a second mAb (one of the thirty-nine purified antibodies) at 10 μg/mL. After the end of each cycle, the covalently coupled surfaces were regenerated. The entire cycle was repeated until all PTK7 mAbs were injected as the second mAb over the complex of hu PTK7-His/antibody surfaces. The cross-competition data were analyzed using the Carterra's epitope binning analysis software. The combined dendograms created based on the cross-competition data were utilized to develop community plots. Asymmetries represent mAbs that show different competition profiles based on the order of addition.

The competition is comprised of four major groupings, which are made up of 17 communities as a result of the uniqueness of the antibodies. The results are summarized in FIG. 1 and in Table 7 (SEQ: SEQ ID NO).

TABLE 7

| Epitope Binning of Anti-PTK7 Antibodies | | | |
|---|---|---|---|
| Clone ID | Ab ID | Epitope Binning ID | Epitope Bin |
| D2D77808-1244 | SLX-1004 | mAb-001 | 1 |
| D2D77808-3188 | SLX-1005 | mAb-002 | 2 |
| D2D77808-3224 | SLX-1006 | mAb-003 | 2 |
| D2D77808-3707 | SLX-1007 | mAb-004 | 3 |
| D2D77808-4647 | SLX-1009 | mAb-005 | 3 |
| D2D77808-5632 | SLX-1011 | mAb-006 | 3 |
| D2D77808-7380 | SLX-1012 | mAb-007 | 3 |
| D2D77808-843 | SLX-1002 | mAb-008 | 2 |
| D2D77808-9018 | SLX-1014 | mAb-009 | 4 |
| D2D77812-3278 | SLX-1021 | mAb-010 | 5 |

TABLE 7-continued

| Epitope Binning of Anti-PTK7 Antibodies | | | |
|---|---|---|---|
| Clone ID | Ab ID | Epitope Binning ID | Epitope Bin |
| D3D88750-15061 | SLX-1027 | mAb-011 | 6 |
| D3D88936-10726 | SLX-1031 | mAb-012 | 5 |
| D3D88936-12014 | SLX-1032 | mAb-013 | 7 |
| D3D88936-13864 | SLX-1033 | mAb-014 | 8 |
| D3D88936-14075 | SLX-1034 | mAb-015 | 6 |
| D3D88936-14742 | SLX-1035 | mAb-016 | 9 |
| D3D88936-14768 | SLX-1036 | mAb-017 | 9 |
| D3D88936-15092 | SLX-1037 | mAb-018 | 7 |
| D3D88936-16478 | SLX-1038 | mAb-019 | 6 |
| D3D88936-18327 | SLX-1040 | mAb-020 | 3 |
| D3D88936-6283 | SLX-1030 | mAb-021 | 10 |
| D3D88936-762 | SLX-1029 | mAb-022 | 6 |
| D4D88750-11630 | SLX-1049 | mAb-023 | 11 |
| D4D88750-13354 | SLX-1051 | mAb-024 | 4 |
| D4D88750-19223 | SLX-1055 | mAb-025 | 12 |
| D4D88750-4395 | SLX-1044 | mAb-026 | 1 |
| D4D88750-9185 | SLX-1047 | mAb-027 | 4 |
| D4D88750-935 | SLX-1042 | mAb-028 | 4 |
| D4D88936-12394 | SLX-1070 | mAb-029 | 13 |
| D4D88936-1474 | SLX-1058 | mAb-030 | 14 |
| D4D88936-14748 | SLX-1071 | mAb-031 | 13 |
| D4D88936-15106 | SLX-1072 | mAb-032 | 15 |
| D4D88936-16655 | SLX-1073 | mAb-033 | 13 |
| D4D88936-3188 | SLX-1059 | mAb-034 | 16 |
| D4D88936-5708 | SLX-1060 | mAb-035 | 13 |
| D4D88936-5760 | SLX-1061 | mAb-036 | 8 |
| D4D88936-6018 | SLX-1064 | mAb-037 | 10 |
| D4D88936-6809 | SLX-1065 | mAb-038 | 13 |
| D4D88936-9137 | SLX-1068 | mAb-039 | 17 |

TABLE 7-continued

| Epitope Binning of Anti-PTK7 Antibodies | | | |
|---|---|---|---|
| Clone ID | Ab ID | Epitope Binning ID | Epitope Bin |
| Clone 188b | | mAb-040 | 18 |
| OTI2E7 | | mAb-041 | 3 |
| HU24 | SLX-1000 | mAb-042 | 2 |

Example 4: Tumor Cell Binding

The binding of select antibodies to NCI-H520 and Jurkat cells was characterized. Briefly, 250,000 cells were seeded per well in a 96-well plate and were resuspended in 100 μL of staining buffer (2% FBS in RPMI) containing antibody. Antibodies were serially diluted 4-fold, beginning at 30 g/mL. Samples were incubated on ice for 20 min, washed three times with 250 μL of wash buffer (2% FBS in PBS), resuspended in 100 μL of secondary antibody (goat anti-human Fc PE, Invitrogen cat. #12-4998-82) and were incubated on ice for 20 min. The cells were washed three times with 250 μL of FACS buffer (2% FBS with 2 mM EDTA in PBS). The cells were either analyzed live or alternatively, were fixed by resuspending in 100 μL of 2% paraformaldehyde in PBS and incubating for 10 min at 25° C. Following fixation, the cells were washed once with 250 μL of FACS buffer and were resuspended in 150 μL of FACS buffer. Control samples included unstained cells, secondary alone, or isotype control. Intact, single cells were isolated and the MFI from the control sample was subtracted.

Figure 2:
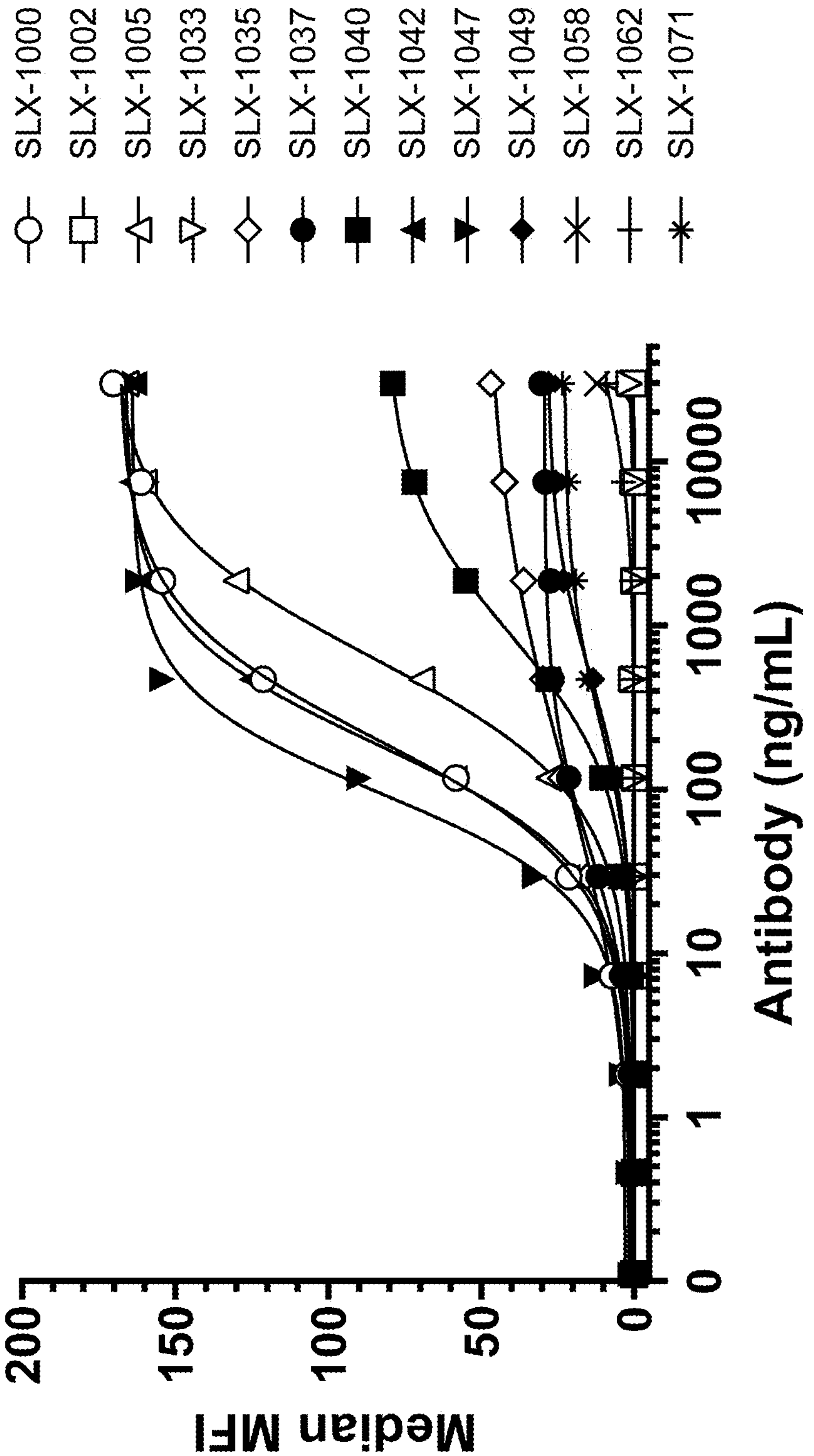
FIG. 2 is a line graph demonstrating the median mean fluorescence intensity (MFI) as a measure of binding of the listed antibodies to NCI-H520 cells.
Figure 3:
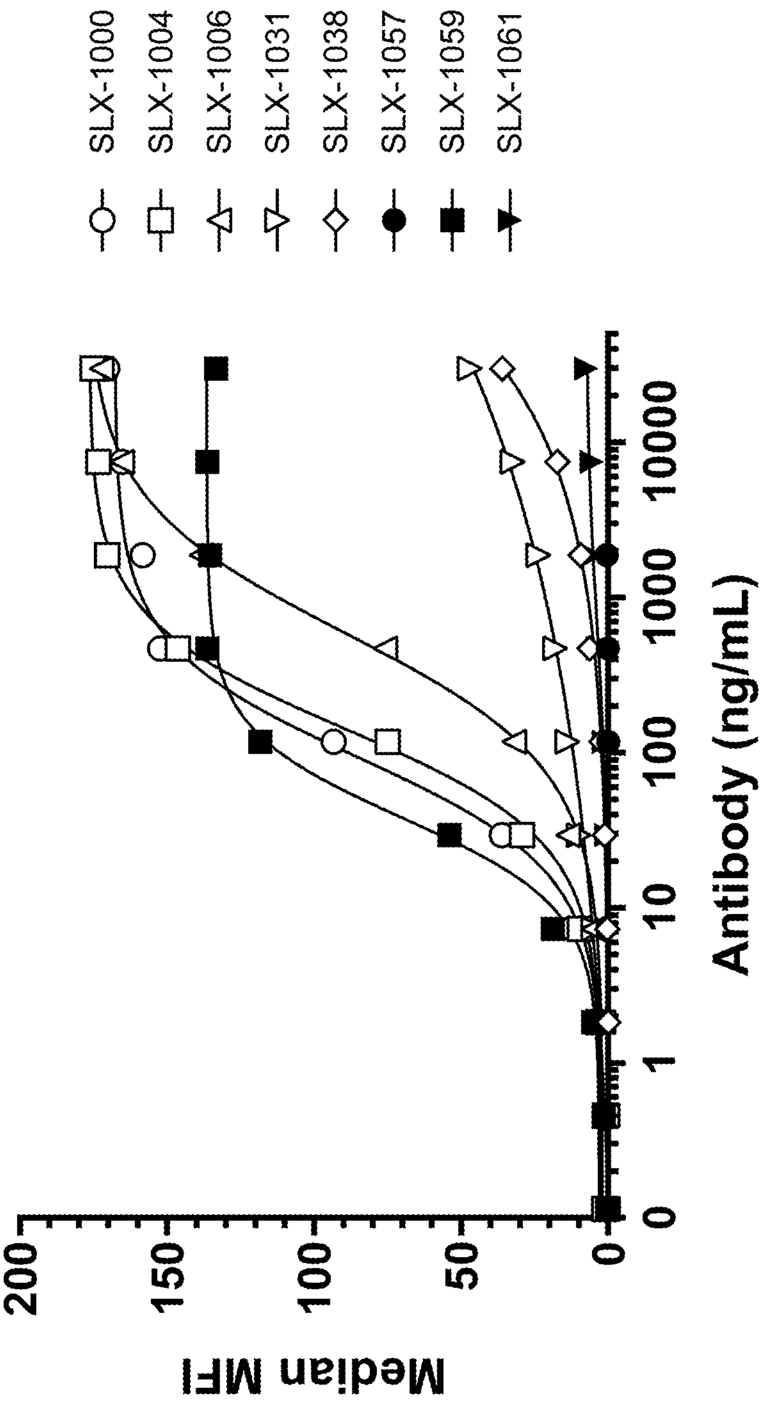
FIG. 3 is a line graph showing binding (median MFI) of the listed antibodies to NCI-H520 cells.
Figure 4:
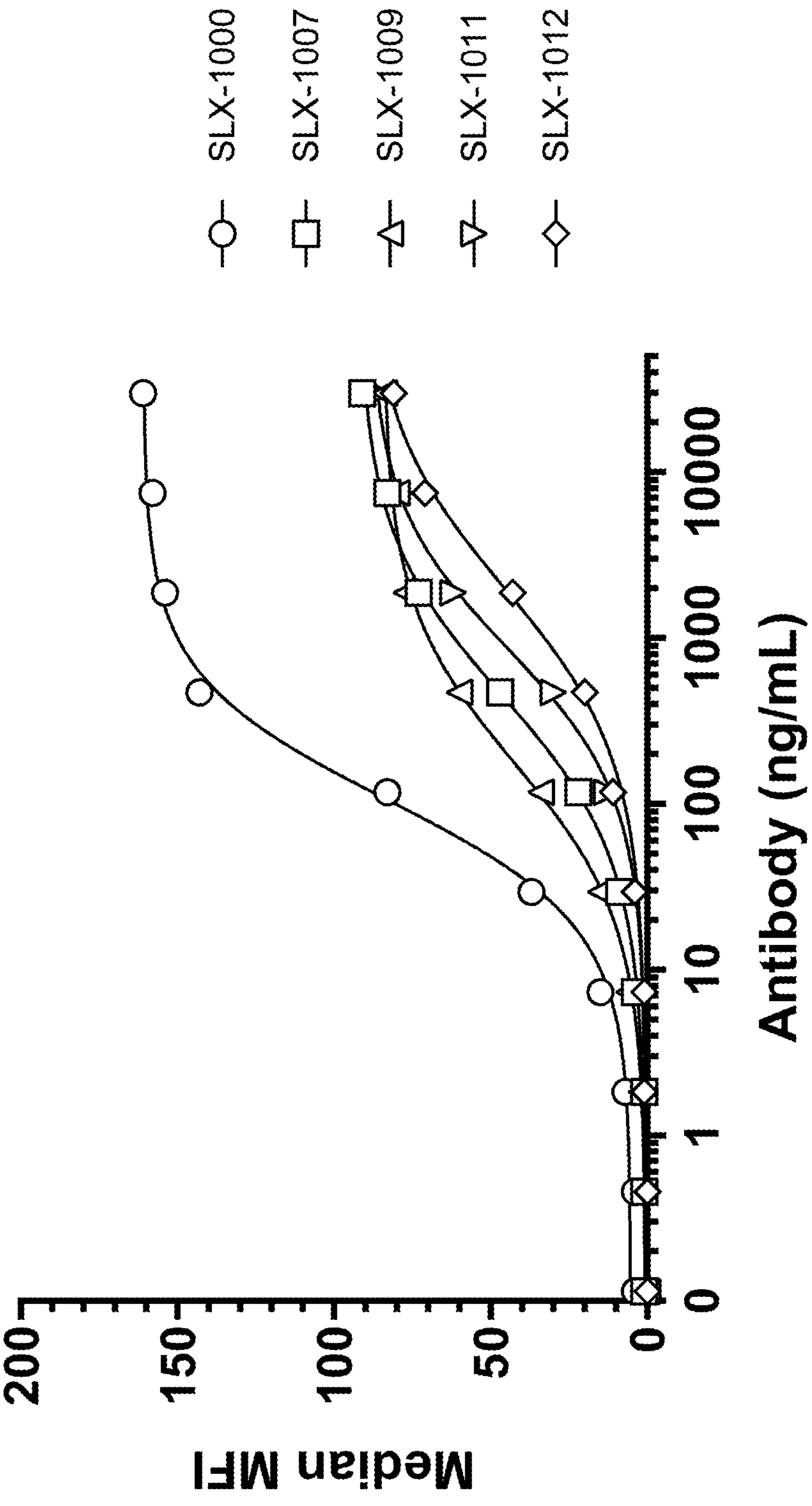
FIG. 4 is a line graph showing binding (median MFI) of the listed antibodies to NCI-H520 cells.
Figure 5:
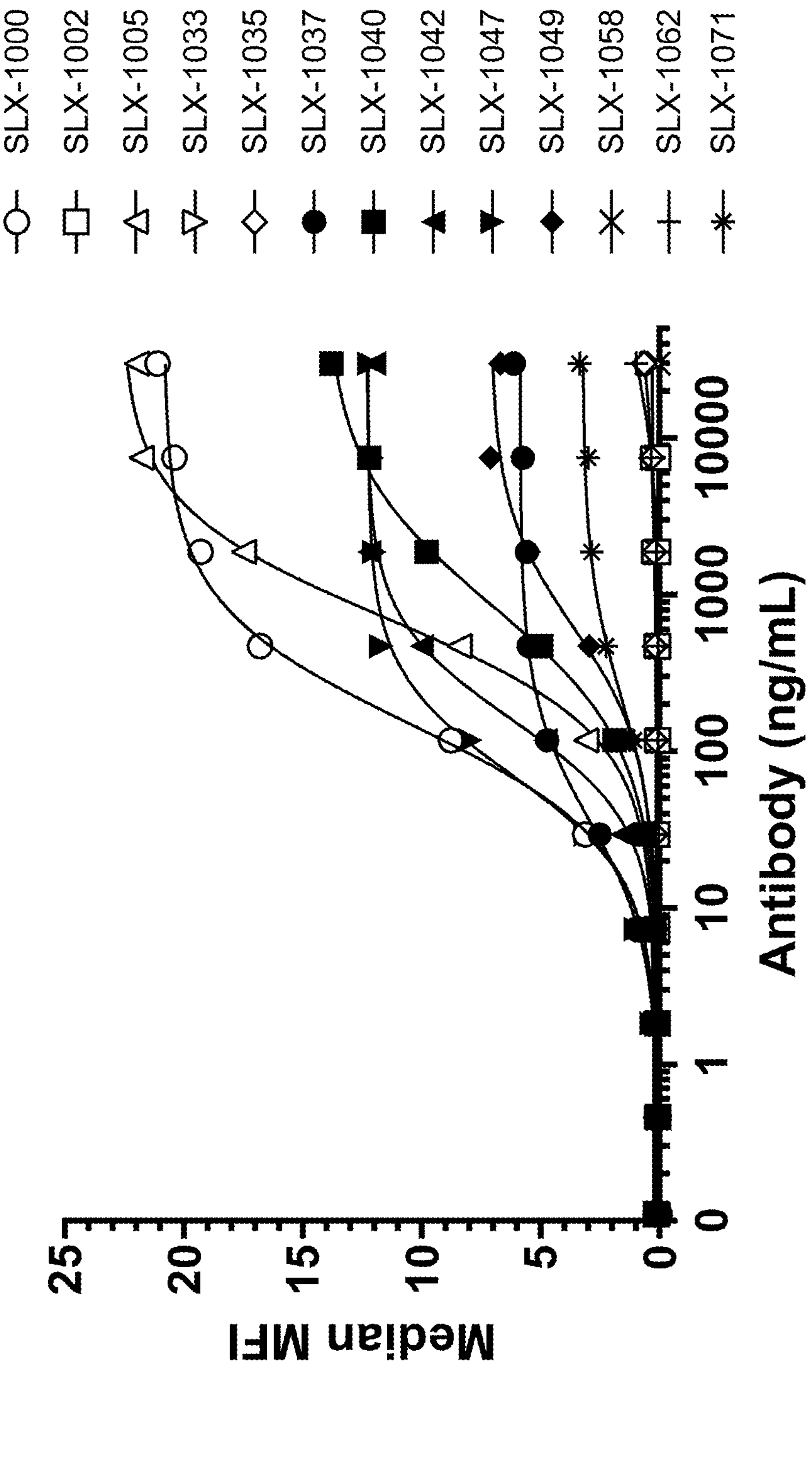
FIG. 5 is a line graph showing the binding (median MFI) of the listed antibodies to Jurkat cells.

The tested antibodies displayed variable binding to tumor cell lines. Specifically, maximal binding to NCI-H520 cells, as indicated by maximum MFI, varied from low (<20 median MFI), to intermediate (20-100 median MFI), to high (>100 median MFI) (FIGS. 2-4). Additionally, the concentration of half-maximal binding ($EC_{50}$) to NCI-H520 cells varied from 0.3 to >13 nM (Table 8). Likewise, maximal binding and the $EC_{50}$ values of the antibodies' binding to Jurkat cells was also variable (FIG. 5 and Table 8).

TABLE 8

| Antibody Binding to Tumor Cell Lines | | | | |
|---|---|---|---|---|
| Clone ID | Epitope Binning ID | Solve ID | H520 Cell Binding $EC_{50}$ (nM) | Jurkat Cell Binding $EC_{50}$ (nM) |
| D2D77808-843 | mAb-008 | SLX-1002 | N.D.* | N.D. |
| D2D77808-1244 | mAb-001 | SLX-1004 | 1.0 | |
| D2D77808-3188 | mAb-002 | SLX-1005 | 4.3 | 4.7 |
| D2D77808-3224 | mAb-003 | SLX-1006 | 3.9 | |
| D2D77808-3707 | mAb-004 | SLX-1007 | 3.0 | |
| D2D77808-4647 | mAb-005 | SLX-1009 | 1.2 | |
| D2D77808-5632 | mAb-006 | SLX-1011 | 5.8 | |
| D2D77808-7380 | mAb-007 | SLX-1012 | 13.2 | |
| D3D88936-10726 | mAb-012 | SLX-1031 | N.D. | |
| D3D88936-13864 | mAb-014 | SLX-1033 | N.D. | N.D. |
| D3D88936-14742 | mAb-016 | SLX-1035 | 1.0 | N.D. |
| D3D88936-15092 | mAb-018 | SLX-1037 | 0.3 | 0.2 |
| D3D88936-16478 | mAb-019 | SLX-1038 | N.D. | |
| D3D88936-18327 | mAb-020 | SLX-1040 | 6.0 | 5.7 |
| D4D88750-935 | mAb-028 | SLX-1042 | 1.3 | 1.1 |
| D4D88750-9185 | mAb-027 | SLX-1047 | 0.6 | 0.5 |
| D4D88750-11630 | mAb-023 | SLX-1049 | 3.3 | 4.2 |
| D4D88936-1008 | | SLX-1057 | N.D. | |
| D4D88936-1474 | mAb-030 | SLX-1058 | N.D. | N.D. |
| D4D88936-3188 | mAb-034 | SLX-1059 | 0.3 | |
| D4D88936-5760 | mAb-036 | SLX-1061 | 4.5 | |

TABLE 8-continued

| Antibody Binding to Tumor Cell Lines | | | | |
|---|---|---|---|---|
| Clone ID | Epitope Binning ID | Solve ID | H520 Cell Binding $EC_{50}$ (nM) | Jurkat Cell Binding $EC_{50}$ (nM) |
| D4D88936-5943 | | SLX-1062 | N.D. | N.D. |
| D4D88936-14748 | mAb-031 | SLX-1071 | 1.8 | 1.5 |
| Hu24 | mAb-042 | SLX-1000 | 1.4, 0.6, 0.7 | 1.0 |

*N.D. indicates low binding or non-saturable binding at the concentrations tested.

The above data show that control antibody Hu24 exhibited nanomolar or sub-nanomolar $EC_{50}$, whereas some of the new antibodies, such as D3D88936-18327 and D2D77808-3188, exhibited $EC_{50}$ values that, while in the nanomolar range, were several-fold higher than that of Hu24. This finding is consistent with data from the soluble PTK7 binding assay, in which these two new antibodies showed $K_D$ values that were one order of magnitude higher than that of Hu24 (Tables 5 and 6). The range of PTK7-binding affinity displayed by these new antibodies would be advantageous over Hu24 in two aspects: (i) lower binding affinity for soluble PTK7 would diminish antigen sink effects, (antibody bound by soluble PTK7 en route to tumor sites reduces the antibody's tumor-targeting efficiency); and (ii) slightly lower antigen-binding affinity on tumor cells would reduce tumor binding-site barrier effects, (peripheral tumor cells bind tightly to high affinity antibody, reducing penetration deep into the tumor tissue by the antibody).

Example 5: Antibody Internalization

The internalization of select antibodies on NCI-H520 cells was characterized. Briefly, 30 μg/mL antibody was incubated with $5\times10^5$ cells per sample on ice for 20 min with occasional gentle mixing. Unbound antibody was removed with three washes using ice-cold assay buffer (2% FBS in RPMI). Following the last wash, the cells were resuspended in ice-cold assay buffer and were transferred to a 37° C. water bath for the indicated time. To terminate internalization, the cells were pelleted at 500 g for 3 min at 4° C., the supernatant was aspirated, and the cells were resuspended in 100 μL of secondary antibody (goat anti-human Fc PE, Invitrogen cat. #12-4998-82) and were incubated on ice for 20 min. Samples were washed three times with 250 μL of ice-cold 2% FBS, 2 mM EDTA in PBS. For analysis of live cells, the cells were resuspended in 150 μL of 2% FBS, 2 mM EDTA in PBS and were analyzed by flow cytometry. Alternatively, after the final wash the cells were fixed in 100 μL of paraformaldehyde in PBS for 10 min at 25° C. The cells were then washed once with 250 μL of 2% FBS, 2 mM EDTA in PBS, resuspended in 150 μL of 2% FBS, 2 mM EDTA in PBS and were analyzed by flow cytometry. The binding signal obtained from cells incubated on ice the entire time (time 0) was designated 100% surface binding and internalization was quantitated by measuring the loss of binding signal over time following incubation at 37° C.

Figure 6:
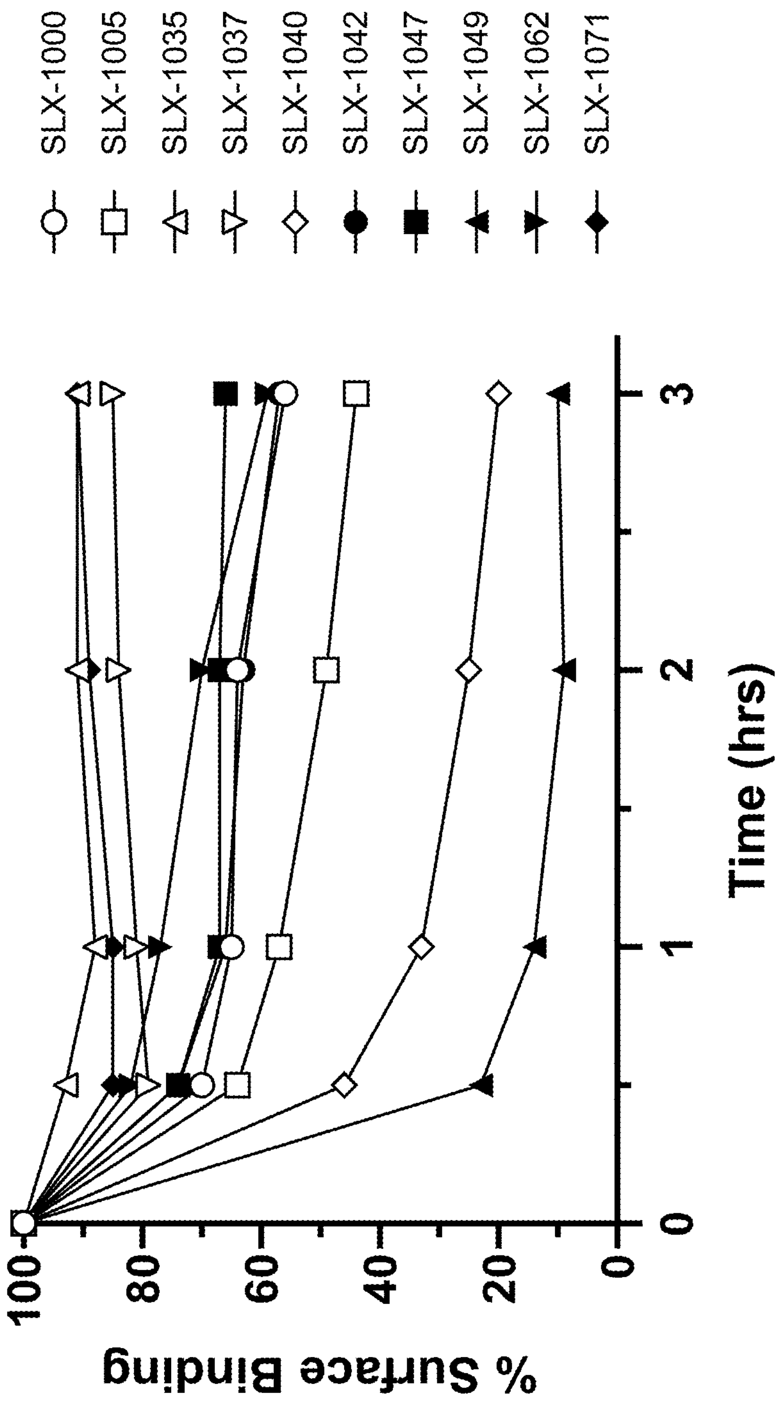
FIG. 6 is a line graph demonstrating the internalization of the listed antibodies in NCI-H520 cells as measured by the loss of surface binding signal over time.
Figure 7:
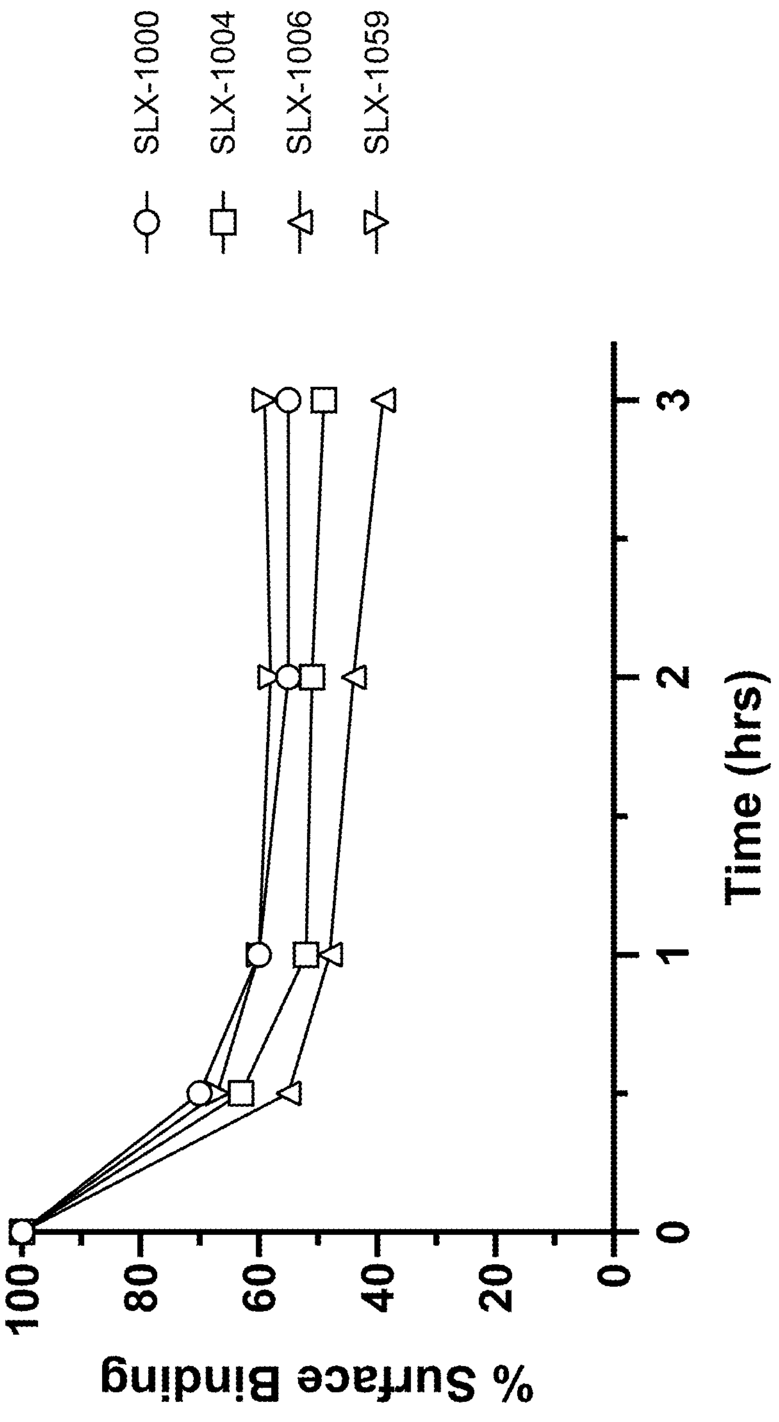
FIG. 7 is a line graph demonstrating the internalization of the listed antibodies in NCI-H520 cells as measured by the loss of surface binding signal over time.
Figure 8:
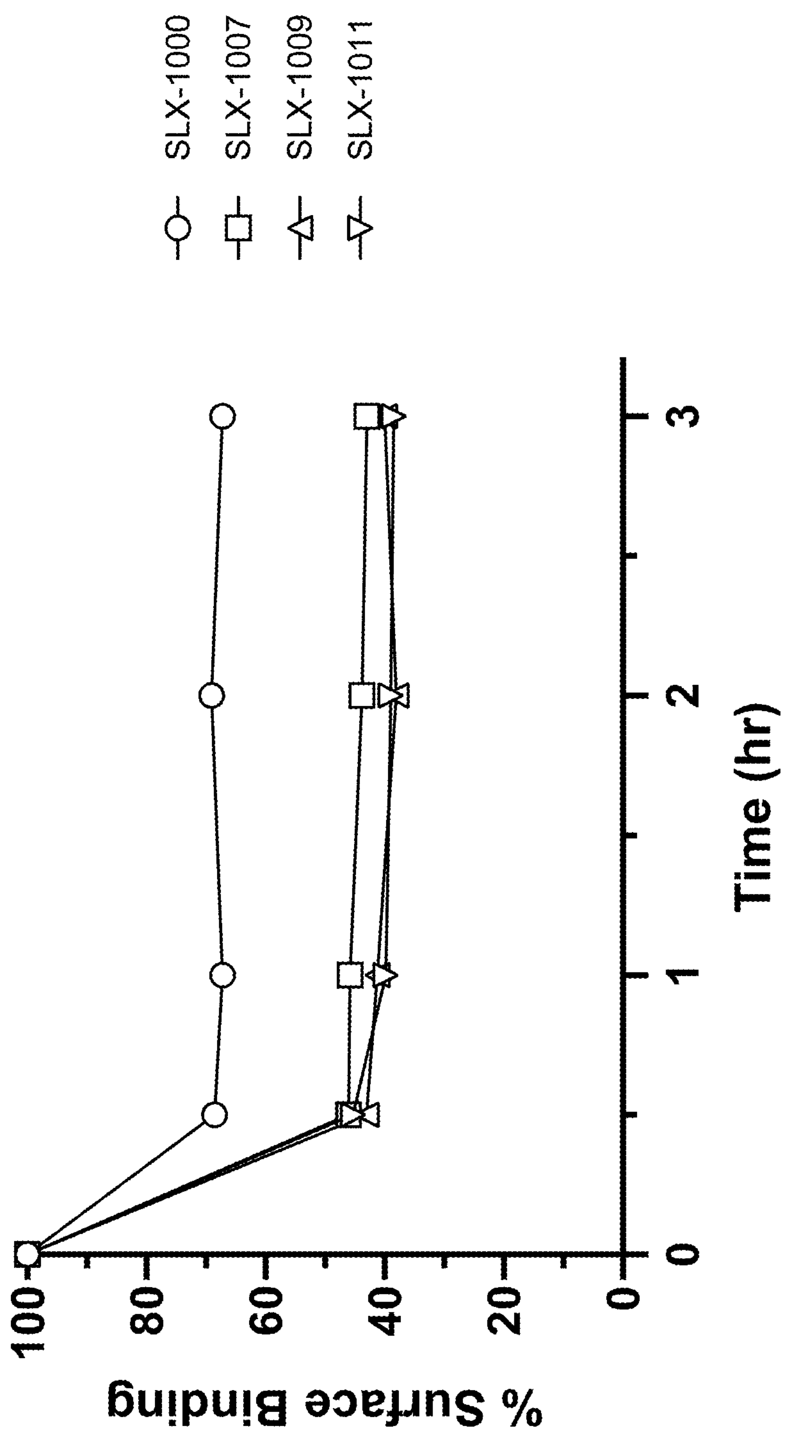
FIG. 8 is a line graph demonstrating the internalization of the listed antibodies in HCI-H520 cells as measured by the loss of surface binding signal over time.

Antibodies displaying a broad range of internalization were identified. The decrease in surface bound antibody was least for SLX-1035 (12%) and SLX-1071 (15%), while SLX-1040 (80%) and SLX-1049 (91%) displayed the greatest decrease in surface bound antibody at 3 hrs (FIG. 6). Multiple antibodies displayed intermediate decreases in surface binding, ranging from 40-62% at 3 hrs (FIGS. 6-8). In general, antibodies from community 3 of the epitope binning experiment (FIG. 1), or the closely-related community 11, displayed the greatest internalization activity. Antibodies from community 2, including the benchmark SLX-1000, also displayed good internalization activity (30-60% decrease in surface binding). Notably, some of the new antibodies, such as SLX-1040 (i.e., D3D88936-18327) and SLX-1049 (i.e., D4D88750-11630), displayed higher levels of internalization as compared to control antibody SLX-1000 (i.e., Hu24) (FIG. 6). Antibodies with high internalization rates would be advantageous for serving as tumor-targeting moieties in antibody-drug conjugates.

Example 6: Sequence Analysis, Template Selection, Framework Mutations

The variable region sequences of murine antibody D3D88936-18327 (SLX-1040) heavy (SEQ ID NO:76) and light chains (SEQ ID NO:75) were analyzed for potential post-translational modification sites and the CDRs were identified. Multiple heavy and light chain CDR definitions were determined, as shown in FIG. 9A. For CDR grafting, the CDRs were defined as the combination of Kabat, Chothia and IMGT definitions. For humanization, the final rows in the tables of FIG. 9A (Grafted Seq) indicate the residues that were grafted into human germline frameworks.

The most homologous human germline framework sequences were identified to be used as acceptor sequences for humanization. The sequence alignment of the heavy and light chains of SLX-1040 with the most homologous human germline heavy chain, IGHV1-46*01, and light chain, IGKVID-16*01, is shown in FIG. 9B. Certain framework residues were identified as being potentially important for preserving the binding activity of SLX-1040 and these residues are marked with an asterisk in FIG. 9B. Multiple variants containing various combinations of back-mutations (human germline framework residues mutated back to corresponding murine framework residue) were synthesized (Z1 through Z22; FIG. 9C) and expressed as $IgG_1$. A chimeric version of SLX-1040 was also made, with the murine $V_H$ and $V_L$, and human $IgG_1$ and K constant regions (ch18327). The framework (FR) back mutations and heavy and light chain combinations of the variants tested are summarized in FIG. 9C. The variants were expressed transiently in Expi293F™ cells and were purified using Protein A chromatography.

Example 7: Characterization of Humanized Variants

The humanized variants were characterized for binding to recombinant human and cynomolgus PTK7, binding to a human tumor cell line expressing PTK7 (NCI-H520), and binding to recombinant CHOK1 cell line transfected with cynomolgus PTK7.

Binding of the purified variants to the extracellular domain (ECD) of recombinant human PTK7 (ACROBiosystems, cat. #PT7-H52H3) was characterized by SPR using a Biacore™ 8K. Antibody was captured using anti-human Fc IgG (Jackson ImmunoResearch) immobilized on a CM5 chip (Cytiva). The antibodies were diluted 100- to 200-fold and the contact time was 60 s at a flow rate of 10 μL/min. Recombinant PTK7 was used at a working concentration of 500 nM, with 180 s association time and a 600 s dissociation time at a flow rate of 30 μL/min. The running buffer was 10 mM HEPES, 150 mM NaCl, 3 mM EDTA, 0.05% Tween 20, pH 7.4. The binding data was evaluated using a 1:1 binding model and Biacore™ evaluation software, using the following formula:

Relative Binding Response (%)=100×[Binding Response (PTK7)×MW (mAb)]/[Capture Level (mAb)×MW (PTK7)×2]

Based on analyzing the dissociation rate, binding response, and relative binding response the most active variants containing the fewest back mutations were Z10-Z15 (Table 9).

TABLE 9

Binding of ch18327 and Humanized Variants to Human PTK7 ECD

| Ligand | $k_d$ (1/s) | Binding Response (RU) | Capture Level (RU) | Relative Binding Response |
|---|---|---|---|---|
| ch18327 | 5.90E−04 | 88.1 | 140 | 59% |
| Z1 | 1.50E−03 | 23.5 | 131.6 | 17% |
| Z2 | 6.15E−04 | 21.2 | 170.6 | 12% |
| Z3 | 1.92E−03 | 28.1 | 148.5 | 18% |
| Z4 | 2.24E−03 | 50.8 | 170.3 | 28% |
| Z5 | 1.95E−03 | 29.2 | 172.1 | 16% |
| Z6 | 2.00E−03 | 32.0 | 173.5 | 17% |
| Z7 | 2.00E−03 | 59.9 | 178.5 | 32% |
| Z8 | 1.37E−03 | 40.8 | 177.6 | 22% |
| Z9 | 1.99E−03 | 53.7 | 170.5 | 30% |
| Z10 | 1.38E−03 | 81.3 | 185.7 | 41% |
| Z11 | 1.31E−03 | 56.7 | 164.6 | 33% |
| Z12 | 1.04E−03 | 65.4 | 170.1 | 36% |
| Z13 | 1.05E−03 | 69.8 | 186.8 | 35% |
| Z14 | 8.83E−04 | 59.3 | 143.2 | 39% |
| Z15 | 9.86E−04 | 69.1 | 181.2 | 36% |
| Z16 | 8.44E−04 | 60.9 | 164.9 | 35% |
| Z17 | 9.61E−04 | 59.1 | 173 | 32% |
| Z18 | 8.70E−04 | 59.6 | 160.5 | 35% |
| Z19 | 1.01E−03 | 47.8 | 160.6 | 28% |
| Z20 | 9.83E−04 | 42.8 | 153.2 | 26% |
| Z21 | 8.61E−04 | 76.9 | 187.5 | 39% |
| Z22 | 6.71E−04 | 75.4 | 163.1 | 44% |

Next, the binding of the purified variants to the extracellular domain (ECD) of recombinant cynomolgus PTK7 (ACROBiosystems, cat. #PT7-C52h3) was characterized by SPR using a Biacore™ 8K. Antibody was captured using anti-human Fc IgG (Jackson ImmunoResearch) immobilized on a CM5 chip (Cytiva). The antibodies were diluted 10- to 50-fold and the contact time was 60 s at a flow rate of 10 μL/min. Recombinant PTK7 was used at a working concentration of 500 nM, with 180 s association time and a 300 s dissociation time at a flow rate of 30 μL/min. The running buffer was 10 mM HEPES, 150 mM NaCl, 3 mM EDTA, 0.05% Tween 20, pH 7.4 (Cytiva, Cat. BR100669). The binding data was evaluated using a 1:1 binding model and Biacore™ evaluation software as described above.

Based on analyzing the dissociation rate, binding response, and relative binding response the most active variants containing the fewest back mutations were Z12-Z14 (Table 10).

TABLE 10

Binding of ch18327 and Humanized Variants to Cynomolgus PTK7 ECD

| Ligand | $k_d$ (1/s) | Binding Response (RU) | Capture Level (RU) | Relative Binding Response |
|---|---|---|---|---|
| ch18327 | 6.38E−03 | 55.8 | 268.6 | 20% |
| Z1 | Weak binding | 4.2 | 396.8 | 1% |
| Z2 | Weak binding | 1.6 | 445.9 | 0% |
| Z3 | Weak binding | 8.0 | 424.1 | 2% |
| Z4 | 8.15E−03 | 17.8 | 452.6 | 4% |
| Z5 | Weak binding | 7.7 | 441.6 | 2% |
| ZE | Weak binding | 7.1 | 355.4 | 2% |
| Z7 | 8.08E−03 | 18.8 | 458.6 | 4% |
| Z8 | Weak binding | 6.7 | 456.5 | 1% |
| | 9.28E−03 | 20.8 | 441 | 4% |
| Z10 | 1.01E−02 | 31.7 | 406.3 | 7% |
| Z11 | 1.02E−02 | 26.7 | 378 | 7% |
| Z12 | 6.36E−03 | 40.6 | 399.8 | 10% |
| Z13 | 6.41E−03 | 37.1 | 408.9 | 9% |
| Z14 | 6.13E−03 | 39.3 | 367.6 | 10% |
| Z15 | 6.22E−03 | 34.6 | 408.3 | 8% |
| Z16 | 6.29E−03 | 23.0 | 431.1 | 5% |
| Z17 | 6.40E−03 | 33.9 | 399 | 8% |
| Z18 | 6.53E−03 | 22.3 | 427.9 | 5% |
| Z19 | 6.63E−03 | 24.8 | 460 | 5% |
| Z20 | 6.43E−03 | 21.6 | 433 | 5% |
| Z21 | 6.76E−03 | 50.1 | 406.6 | 12% |
| Z22 | 6.03E−03 | 44.2 | 309 | 14% |

Figure 10:
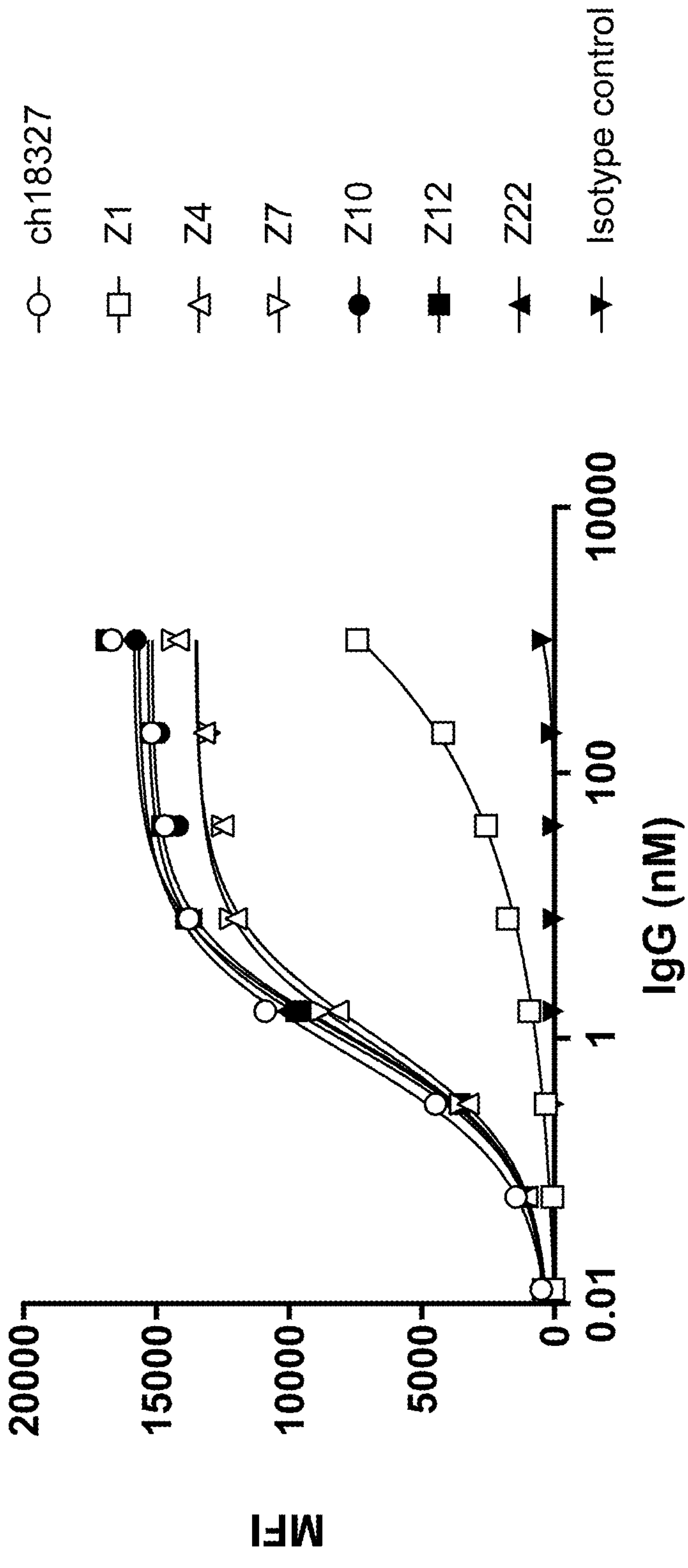
FIG. 10 is a line graph showing binding (MFI) of the listed antibodies to NCI-H520 cells.

The binding of the variants to the human tumor cell line NCI-H520 was characterized using flow cytometry. Briefly, five-fold serial dilutions of antibody were incubated with $1\times10^5$ cells for 1 h at 4° C. Unbound antibody was removed by washing and the cells were incubated with anti-human IgG-Fc-PE diluted 100-fold for 30 min at 4° C. Unbound antibody was removed by washing and the cells were analyzed by flow cytometry. Representative binding of some of the variants is shown in FIG. 10. Variant Z1 (FIG. 10, open squares) displayed significantly diminished binding, while variants ZA (open triangles) and Z7 (open inverted triangles) displayed slightly diminished binding. However, multiple variants display similar maximum MFI and cell binding $EC_{50}$ (FIG. 10, compare Z10, Z12, Z22 with chimeric 18327). No binding was observed with an isotype control antibody (FIG. 10, inverted closed triangles). The maximum MFI and $EC_{50}$ (nM) for binding for all the humanized variants are summarized in Table 11.

TABLE 11

Binding of ch18327 and Humanized Variants to NCI-H520 and CHO cells Expressing Cynomolgus PTK7

| Variant | NCI-H520 Max. MFI | NCI-H520 $EC_{50}$ (nM) | Cynomolgus PTK7 CHO Max. MFI | Cynomolgus PTK7 CHO $EC_{50}$ (nM) |
|---|---|---|---|---|
| ch18327 | 15680 | 0.78 | 2077 | 0.07 |
| Z1 | 7440 | NA | 133 | NA |
| Z2 | 7025 | NA | 93 | NA |
| Z3 | 13177 | 1.94 | 1467 | 0.30 |
| Z4 | 13548 | 1.08 | 1484 | 0.13 |
| Z5 | 13207 | 1.61 | 1274 | 0.17 |
| Z6 | 17802 | 3.31 | 1357 | 0.20 |
| Z7 | 13487 | 0.91 | 1317 | 0.09 |
| Z8 | 13925 | 2.20 | 1467 | 0.20 |

TABLE 11-continued

Binding of ch18327 and Humanized Variants to NCI-H520 and CHO cells Expressing Cynomolgus PTK7

| Variant | NCI-H520 Max. MFI | NCI-H520 $EC_{50}$ (nM) | Cynomolgus PTK7 CHO Max. MFI | Cynomolgus PTK7 CHO $EC_{50}$ (nM) |
|---|---|---|---|---|
| Z9 | 13885 | 1.30 | 1614 | 0.12 |
| Z10 | 15176 | 1.04 | 1781 | 0.08 |
| Z11 | 15323 | 1.31 | 1613 | 0.10 |
| Z12 | 15868 | 1.08 | 1645 | 0.08 |
| Z13 | 15595 | 0.92 | 1653 | 0.07 |
| Z14 | 16304 | 0.94 | 1783 | 0.07 |
| Z15 | 15786 | 0.87 | 1798 | 0.07 |
| Z16 | 15131 | 1.51 | 1836 | 0.08 |
| Z17 | 14925 | 1.28 | 2007 | 0.10 |
| Z18 | 15213 | 1.19 | 1853 | 0.07 |
| Z19 | 15388 | 1.37 | 1890 | 0.09 |
| Z20 | 15673 | 1.22 | 1759 | 0.07 |
| Z21 | 15192 | 1.15 | 1737 | 0.07 |
| Z22 | 15338 | 0.92 | 1961 | 0.07 |

Figure 11:
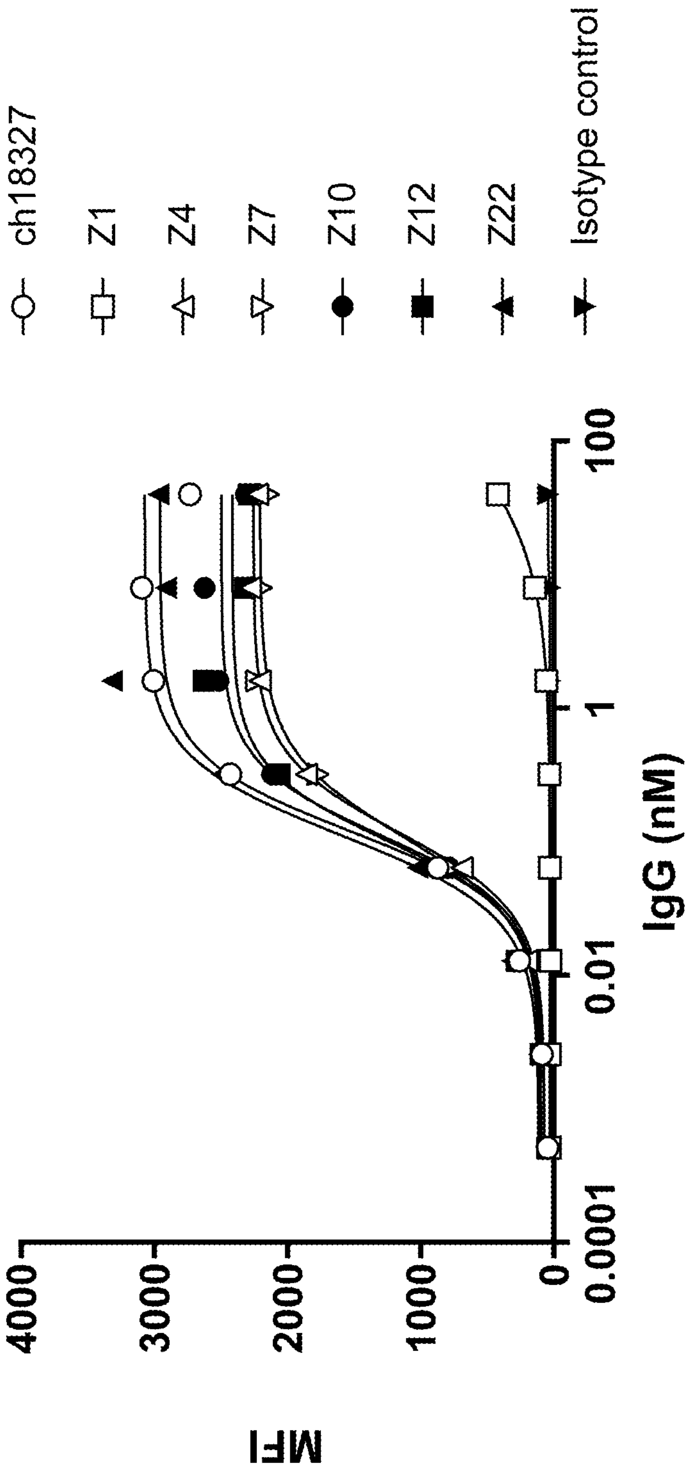
FIG. 11 is a line graph showing binding (MFI) of the listed antibodies to CHO cells expressing cynomolgus PTK7.

Next, the binding of the variants to CHO cells expressing cynomolgus PTK7 was characterized using flow cytometry. Briefly, five-fold serial dilutions of antibody were incubated with $1\times10^5$ cells for 1 h at 4° C. Unbound antibody was removed by washing and the cells were incubated with anti-human IgG-Fc-PE diluted 100-fold for 30 min at 4° C. Unbound antibody was removed by washing and the cells were analyzed by flow cytometry. Representative binding is shown in FIG. 11. Variant Z1 (open squares) displayed minimal binding to CHO cells expressing cynomolgus PTK7. Multiple variants, including variant Z22 (FIG. 11, closed triangles) displayed a similar maximum MFI to chimeric 18327 (FIG. 11, open circles). Similarly, multiple variants bound the transfected CHO cells with cell binding $EC_{50}$ comparable to chimeric 18327 (FIG. 11, compare Z7, Z10, Z12, and Z22 with chimeric 18327). No binding was observed with an isotype control antibody (FIG. 11, inverted closed triangles). The maximum MFI and $EC_{50}$ (nM) for binding to CHO cells transfected with cynomolgus PTK7 are summarized in Table 11.

Based on the binding of humanized variants to recombinant human and cynomolgus PTK7 ECD and on binding to cells expressing human or cynomolgus PTK7 certain murine framework residues were identified as potentially important for preserving the activity of the murine antibody 18327. Specifically, variant Z12 displayed the best overall binding to recombinant human and cynomolgus PTK7 and to cells expressing human and cynomolgus PTK7, while containing the fewest back mutations of the variants expressed in this first panel. Variant Z12 contains Y91F, R71V, V78A back mutations in the VH and Y36L, S46R, G66R, F71Y mutations in the VL.

Example 8: Further Refinement of Humanized Variants

In an attempt to further reduce the total number of back mutations while preserving the binding activity of the antibody, twelve additional variants (Z23-Z34) were synthesized and characterized (FIG. 9D). The variants were expressed transiently in Expi293F™ cells and were purified using Protein A chromatography. The variants all expressed well and were purified to >99% as assessed by analytical SEC, with the exception of variants Z27 and Z32, which expressed well and were purified to >93% as assessed by analytical SEC.

The humanized variants were characterized for binding to recombinant human and cynomolgus PTK7, binding to a human tumor cell line expressing PTK7 (NCI-H520), and binding to recombinant CHOK1 cell line transfected with cynomolgus PTK7.

The binding of the purified variants to the ECD of recombinant human PTK7 and the ECD of recombinant cynomolgus PTK7 was characterized by SPR using a Biacore™ 8K. Antibody was captured using anti-human Fc IgG (Jackson ImmunoResearch) immobilized on a CM5 chip (Cytiva). The antibodies were diluted to 1.5 μg/mL and were captured for 80 s at a flow rate of 10 μL/min. Recombinant human PTK7 was used at a working concentration of 500 nM, with 180 s association time and a 600 s dissociation time at a flow rate of 30 μL/min, while recombinant cynomolgus PTK7 was used at a working concentration of 500 nM, with 180 s association time and a 300 s dissociation time at a flow rate of 30 u L/min. The running buffer was 10 mM HEPES, 150 mM NaCl, 3 mM EDTA, 0.05% Tween 20, pH 7.4. The binding data was evaluated using a 1:1 binding model and Biacore™ evaluation software as described above.

The variants all displayed similar dissociation rates (ka) with human recombinant PTK7, ranging from $1.34\times10^{-3}$ $s^{-1}$ (Z12) to $3.90x^{-3}$ $s^{-1}$ (Z27), as summarized in Table 12. The dissociation rates of the humanized variants were slightly faster than the chimeric 18327 ($6.96\times10^{-4}$ $s^{-1}$). Four variants had ka rates within 2-fold of the chimeric 18327: Z12, Z23, Z29, and Z31. Additionally, the Relative Binding Response of the humanized variants ranged from 33% (Z26) on the low end to 43% (Z32) on the high end (Table 12). The Relative Binding Response of variants Z23 (40%) and Z32 (43%) were closest to chimeric 18327 (50%).

TABLE 12

Binding of ch18327 and Humanized Variants to Human PTK7 ECD

| Ligand | $k_d$ (1/s) | Binding Response (RU) | Capture Level (RU) | Relative Binding Response |
|---|---|---|---|---|
| ch18327 | 6.96E−04 | 86.7 | 162.9 | 50% |
| Z12 | 1.34E−03 | 68.4 | 160.6 | 40% |
| Z23 | 1.39E−03 | 66.4 | 161.4 | 39% |
| Z24 | 2.22E−03 | 66.4 | 163.8 | 38% |
| Z25 | 2.36E−03 | 64 | 169.3 | 36% |
| Z26 | 2.54E−03 | 61.5 | 177.2 | 33% |
| Z27 | 3.90E−03 | 68.8 | 170.2 | 38% |
| Z28 | 2.44E−03 | 67.2 | 185.4 | 34% |
| Z29 | 1.46E−03 | 63.3 | 157.8 | 38% |
| Z30 | 3.77E−03 | 70.5 | 163 | 41% |
| Z31 | 1.54E−03 | 63.7 | 164.5 | 37% |
| Z32 | 2.26E−03 | 81.7 | 177.4 | 43% |

The variants all displayed similar dissociation rates at 300 s with cynomolgus recombinant PTK7, ranging from $3.08\times10^{-3}$ $s^{-1}$ (Z27) to $8.67\times10^{-3}$ $s^{-1}$ (Z29), as summarized in Table 13. The dissociation rates of the humanized variants were similar to chimeric 18327 ($6.97\times10^{-3}$ $s^{-1}$), with chimeric 18327 dissociating approximately ten times faster from cynomolgus PTK7 than from human PTK7. For binding to recombinant cynomolgus PTK7 the antibodies showed heterogeneous binding, with faster off rates observed in the first 120 s followed by very slow dissociation. Consequently, the dissociation rates at 120 s were also characterized. Again, the variants were similar, displaying dissociation rates ranging from $1.30\times10^{-3}$ $s^{-1}$ (Z25) to $9.66\times10^{-3}$ $s^{-1}$ (Z32). Dissociation of the variants at 120 s was equivalent or slightly faster than was observed with chimeric 18327 at 120 s ($8.71\times10^{-3}$ $s^{-1}$), with the exception of Z27 ($7.60\times10^{-3}$ $s^{-1}$). The Relative Binding Response of the humanized variants ranged from 8% (Z26) on the low end to 16% (Z32) on the high end (Table 13). The Relative Binding Response of multiple variants was 12-16%, compared to 24% for chimeric 18327. In general, the binding of chimeric 18327 and humanized variants to recombinant cynomolgus PTK7 was weaker than their binding to recombinant human PTK7.

TABLE 13

Binding of ch18327 and Humanized Variants to Cynomolgus PTK7 ECD

| Ligand | $k_d$ (1/s) 300 s | $k_d$ (1/s) 120 s | Binding Response (RU) | Capture Level (RU) | Relative Binding Response |
|---|---|---|---|---|---|
| ch18327 | 6.79E−03 | 8.71E−03 | 42.9 | 166.3 | 24% |
| Z12 | 6.67E−03 | 1.03E−02 | 25.1 | 163.8 | 14% |
| Z23 | 6.71E−03 | 1.06E−02 | 23 | 164.5 | 13% |
| Z24 | 4.73E−03 | 9.80E−03 | 21.9 | 167.1 | 12% |
| Z25 | 7.19E−03 | 1.30E−02 | 17.4 | 173 | 9% |
| Z26 | 5.02E−03 | 1.08E−02 | 15 | 180.3 | 8% |
| Z27 | 3.08E−03 | 7.60E−03 | 20.1 | 173.5 | 11% |
| Z28 | 5.73E−03 | 1.17E−02 | 16.5 | 188.6 | 8% |
| Z29 | 8.67E−03 | 1.28E−02 | 18.9 | 159.7 | 11% |
| Z30 | 3.93E−03 | 8.66E−03 | 21.2 | 165.1 | 12% |
| Z31 | 7.90E−03 | 1.25E−02 | 19.4 | 166.4 | 11% |
| Z32 | 4.62E−03 | 9.66E−03 | 29.9 | 179.8 | 16% |

Figure 12:
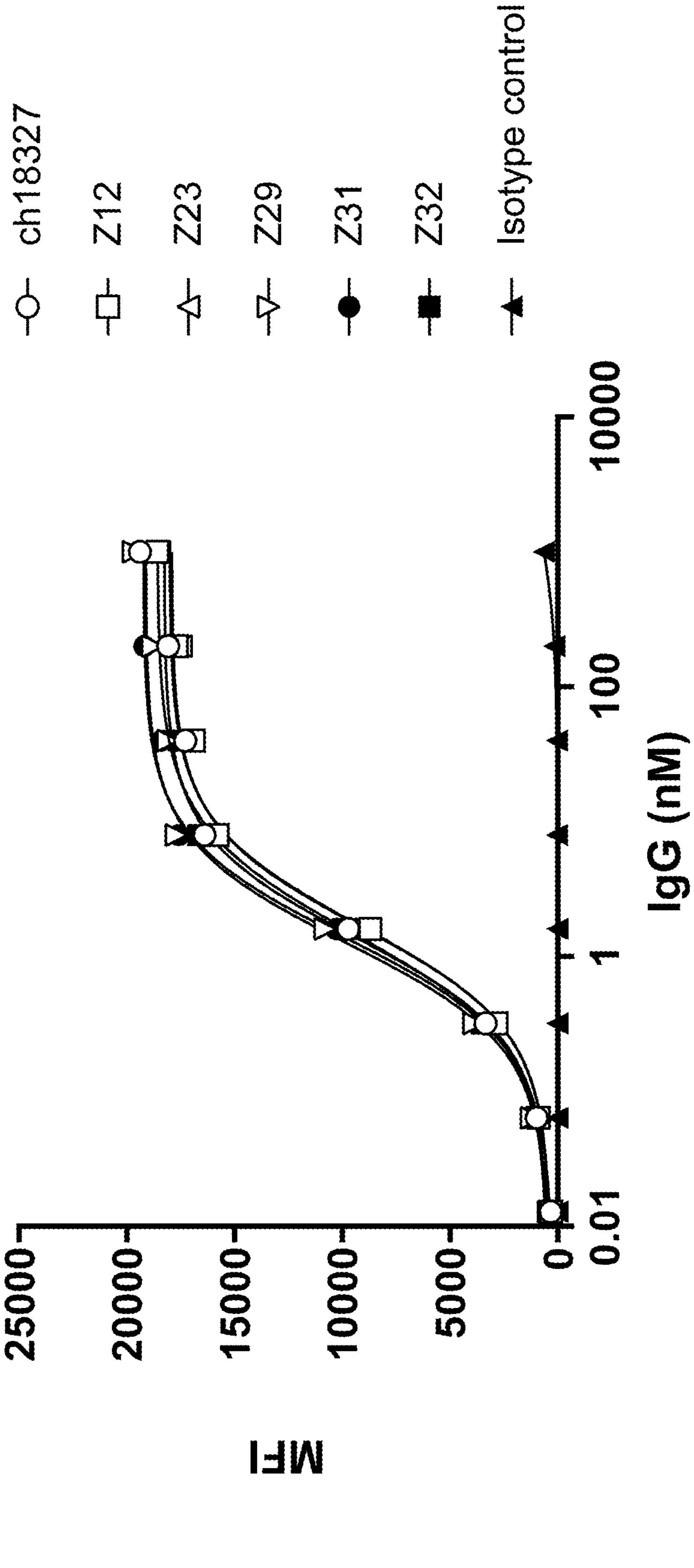
FIG. 12 is a line graph showing binding (MFI) of the listed antibodies to NCI-H520 cells expressing cynomolgus PTK7.
Figure 13:
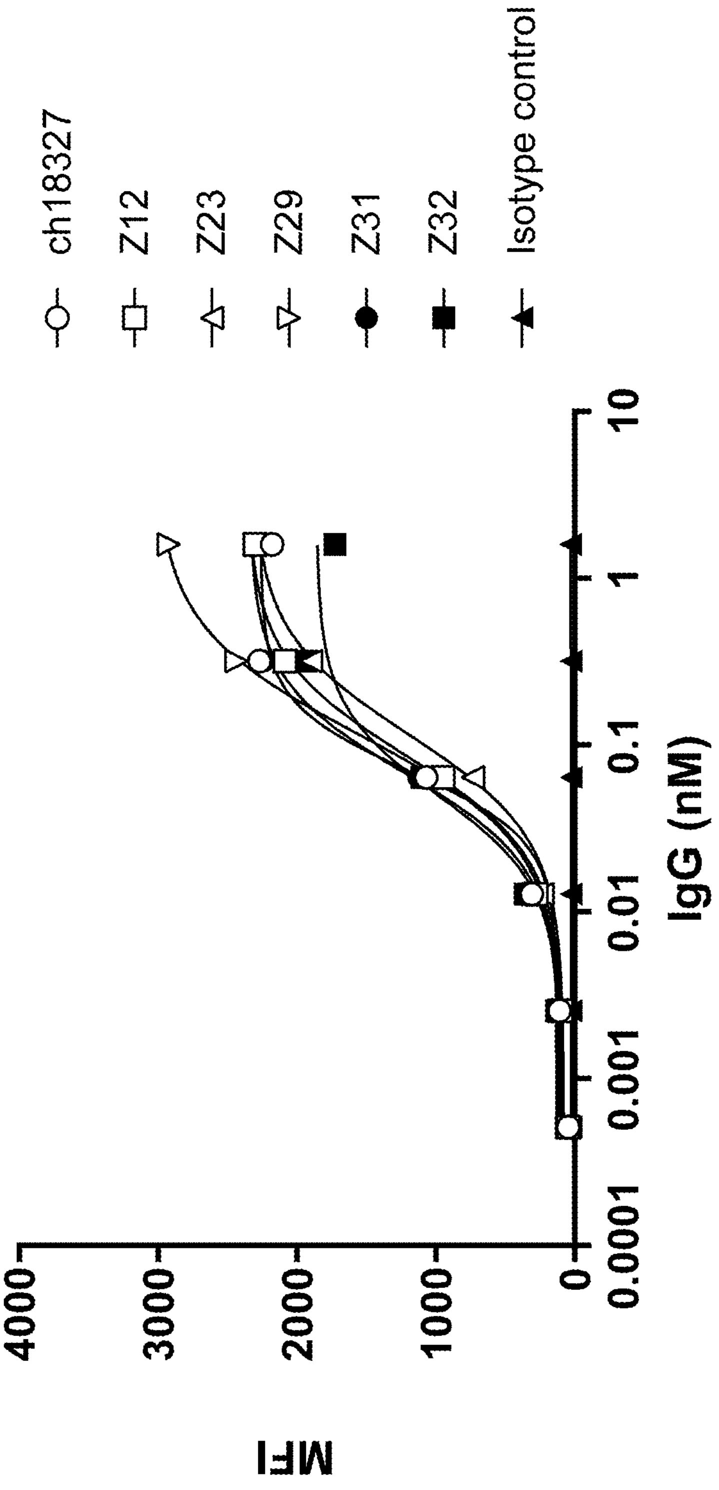
FIG. 13 is a line graph showing binding (MFI) of the listed antibodies to CHO cells expressing cynomolgus PTK7.

The binding of the variants to the human tumor cell line NCI-H520 and CHO cells expressing cynomolgus PTK7 was characterized using flow cytometry, as described in Example 7. Multiple variants bound NCI-H520 with an $EC_{50}$ and maximum MFI similar to chimeric 18327. For example, the binding profiles of humanized clones Z12, Z23, Z29, Z31, and Z32 were all similar to chimeric 18327 (FIG. 12). Likewise, multiple variants bound CHO cells transfected with cynomolgus PTK7 similar to chimeric 18327 (FIG. 13). The maximum MFI and $EC_{50}$ (nM) for binding to both cell lines are summarized in Table 14.

TABLE 14

Binding of ch18327 and Humanized Variants to NCI-H520 and CHO cells Expressing Cynomolgus PTK7

| Variant | NCI-H520 Max. MFI | NCI-H520 $EC_{50}$ (nM) | Cyno PTK7 CHO Max. MFI | Cyno PTK7 CHO $EC_{50}$ (nM) |
|---|---|---|---|---|
| ch18327 | 18,597 | 1.46 | 2,264 | 0.07 |
| Z12 | 18,030 | 1.69 | 2,361 | 0.09 |
| Z23 | 17,933 | 1.66 | 2,321 | 0.12 |
| Z24 | 17,294 | 1.62 | 2,156 | 0.09 |
| Z25 | 17,061 | 1.60 | 2,219 | 0.12 |
| Z26 | 16,991 | 1.40 | 1,862 | 0.07 |
| Z27 | 16,659 | 1.29 | 1,990 | 0.12 |
| Z28 | 18,326 | 1.21 | 2,136 | 0.07 |
| Z29 | 19,138 | 1.26 | 3,024 | 0.12 |
| Z30 | 16,768 | 1.22 | 1,904 | 0.08 |
| Z31 | 19,239 | 1.38 | 2,342 | 0.07 |
| Z32 | 18,282 | 1.39 | 1,861 | 0.05 |
| Isotype control | NA | NA | NA | NA |

Example 9: Thermal Stability of Select Humanized Variants

The thermal stability of select humanized variants was characterized by Differential Scanning Fluorimetry (DSF). Chimeric 18327 and variants Z12, Z23, Z29, and Z31 were suspended in PBS at 1 mg/mL and the $T_{m1}$ (° C.) was measured twice. The variants mean $T_{m1}$ ranged from 68.4° C. (Z29) to 71.2° C. (Z23), all higher than chimeric 18327 $T_{m1}$ (64.5° C.), as summarized in Table 15.

TABLE 15

Thermal Stability of ch18327 and Select Humanized Variants

| Variant | Mean $T_{m1}$ (° C.) |
|---|---|
| Chimeric 18327 | 64.5 |
| Z12 | 68.8 |
| Z23 | 71.2 |
| Z29 | 68.4 |
| Z31 | 70.9 |

Example 10: Binding Kinetics of Select Humanized Variants

The binding of the purified variants to the ECD of recombinant human PTK7 was characterized by SPR using a Biacore™ 8K. Antibody was captured using anti-human Fc IgG (Jackson ImmunoResearch) immobilized on a CM5 chip (Cytiva). The antibodies (ligand) were diluted to 1.5 µg/mL and were captured for 70 s at a flow rate of 10 µl/min. Recombinant human PTK7 (analyte) was used at seven concentrations, beginning at 500 nM and diluted serially, two-fold to 7.813 nM with 180 s association time and a 600 s dissociation time at a flow rate of 30 µL/min. The running buffer was 10 mM HEPES, 150 mM NaCl, 3 mM EDTA, 0.05% Tween 20, pH 7.4. The binding data was evaluated using a 1:1 binding model and Biacore™ evaluation software. The humanized antibodies all displayed binding affinities similar, though slightly less than, chimeric 18327. The results are summarized in Table 16.

TABLE 16

Antibody Binding Kinetics to Human PTK7

| Ligand | $k_a$ (1/Ms) | $k_d$ (1/s) | $K_D$ (M) |
|---|---|---|---|
| Chimeric 18327 | 3.07E+04 | 6.96E−04 | 2.27E−08 |
| Z12 | 2.09E+04 | 1.28E−03 | 6.15E−08 |
| Z23 | 2.02E+04 | 1.37E−03 | 6.80E−08 |
| Z29 | 2.18E+04 | 1.50E−03 | 6.89E−08 |
| Z31 | 2.14E+04 | 1.49E−03 | 6.96E−08 |

Next, the binding of the purified variants to the ECD of recombinant cynomolgus PTK7 was characterized by SPR using a Biacore™ 8K. Antibody was captured using anti-human Fc IgG (Jackson ImmunoResearch) immobilized on a CM5 chip (Cytiva). The antibodies (ligand) were diluted to 2 µg/mL (chimeric 18327) or 3 µg/mL (humanized variants) and were captured for 70 s at a flow rate of 10 µL/min. Recombinant PTK7 (analyte) was used at seven concentrations, beginning at 500 nM and diluted serially, two-fold to 7.813 nM. With 180 s association time and a 300 s dissociation time at a flow rate of 30 µL/min. The running buffer was 10 mM HEPES, 150 mM NaCl, 3 mM EDTA, 0.05% Tween 20, pH 7.4. The binding data was evaluated using a 1:1 binding model and Biacore™ evaluation software. The humanized antibodies all displayed binding affinities similar, though slightly less than, chimeric 18327. The results are summarized in Table 17.

TABLE 17

| Kinetics of Antibody Binding to Cynomolgus PTK7 | | | |
|---|---|---|---|
| Ligand | $k_a$ (1/Ms) | $k_d$ (1/s) | $K_D$ (M) |
| Chimeric 18327 | 2.56E+04 | 6.94E−03 | 2.71E−07 |
| Z12 | 1.97E+04 | 8.72E−03 | 4.44E−07 |
| Z23 | 1.91E+04 | 8.79E−03 | 4.59E−07 |
| Z29 | 1.96E+04 | 9.00E−03 | 4.58E−07 |
| Z31 | 2.13E+04 | 8.22E−03 | 3.86E−07 |

Example 11: Binding of Humanized Variants to NCI-H520 (human) and CMMT (rhesus) Cell Lines The binding of a subset of humanized variants to human (NCI-H520) and rhesus (CMMT) tumor cell lines was investigated using flow cytometry. The protein sequence of the extracellular domain of rhesus and cynomolgus PTK7 is identical. Briefly, log-phase growing cells were detached using Accutase® solution (Millipore Sigma) at 37° C., diluted into culture media and collected by centrifugation at 500×g for 3 min. The cells were resuspended in cold 2% FBS in RPMI (binding buffer) at $2\times10^6$ cells/mL. Next, cells were seeded at 50 μL per well (100,000 cells) in a 96-well v-bottom plate. Antibodies were serially diluted 4-fold in binding, beginning at 100 μg/mL, and 50 μL per well was added to the cells and incubated on ice for 30 min. The samples were washed three times with 200 μL of 2% FBS in PBS (FACS buffer), resuspended in 100 μL of secondary antibody (goat anti-human Fc PE, Invitrogen cat. #12-4998-82) diluted 500-fold in binding buffer and were incubated on ice (in the dark) for 30 min. The secondary antibody solution also contained Fixable Viability Dye eFluor™ 780 (Invitrogen) diluted 200-fold. The cells were washed three times with 200 μL of FACS buffer and were fixed with 100 μL of 2% paraformaldehyde aqueous solution (PFA) (Electron Microscopy Sciences) at 25° C. (in the dark) for 10 min. The cells were washed two times with 200 μL of FACS buffer, resuspended in 200 μL of 2 mM EDTA in PBS, and were stored at 4° C. in the dark until analyzed by flow cytometry. Antibody binding was quantitated by measuring the PE median fluorescence intensity (MFI) from 10,000 events of viable singlet cells. Intact, single cells were isolated and the MFI from the control sample (secondary antibody only) was subtracted.

Figure 14:
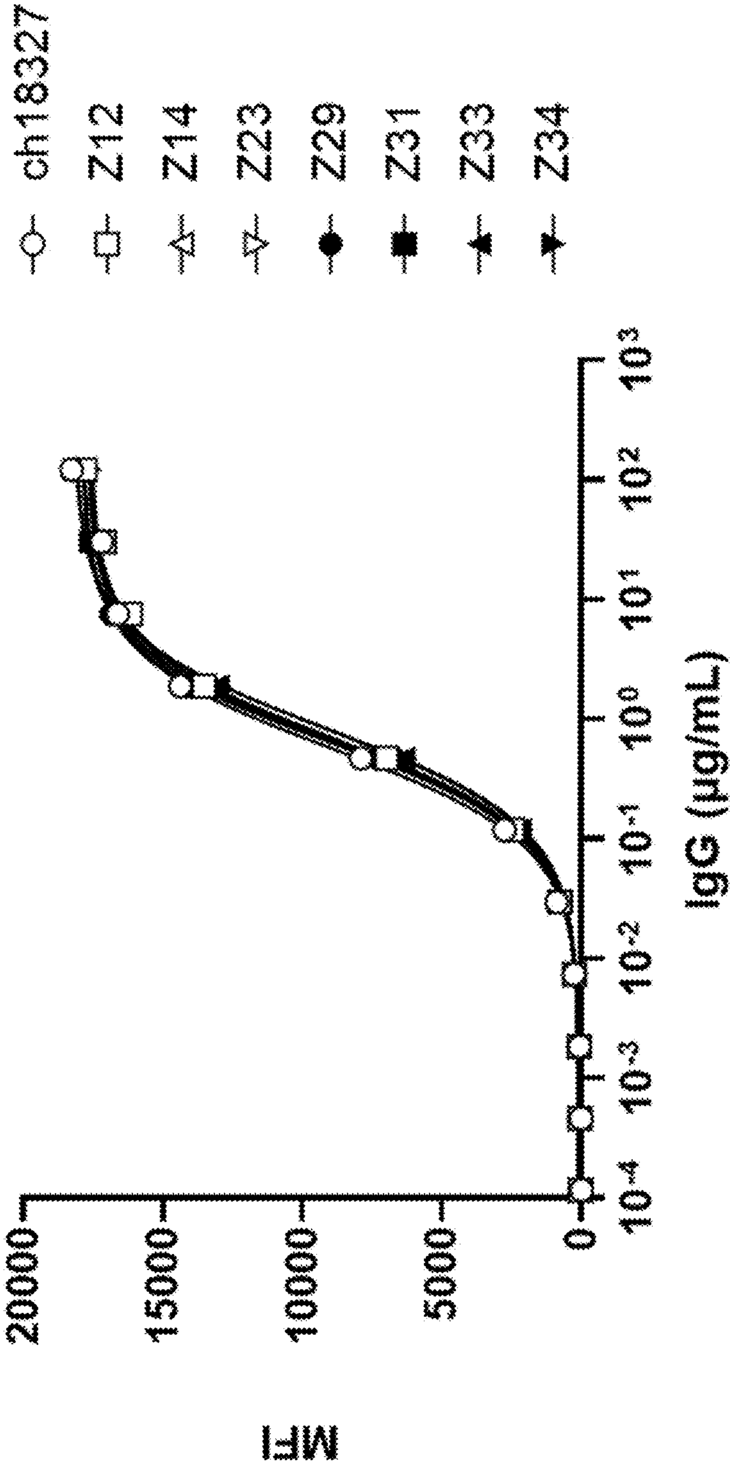
FIG. 14 is a line graph showing binding (MFI) of the listed antibodies to NCI-H520 cells.
Figure 15:
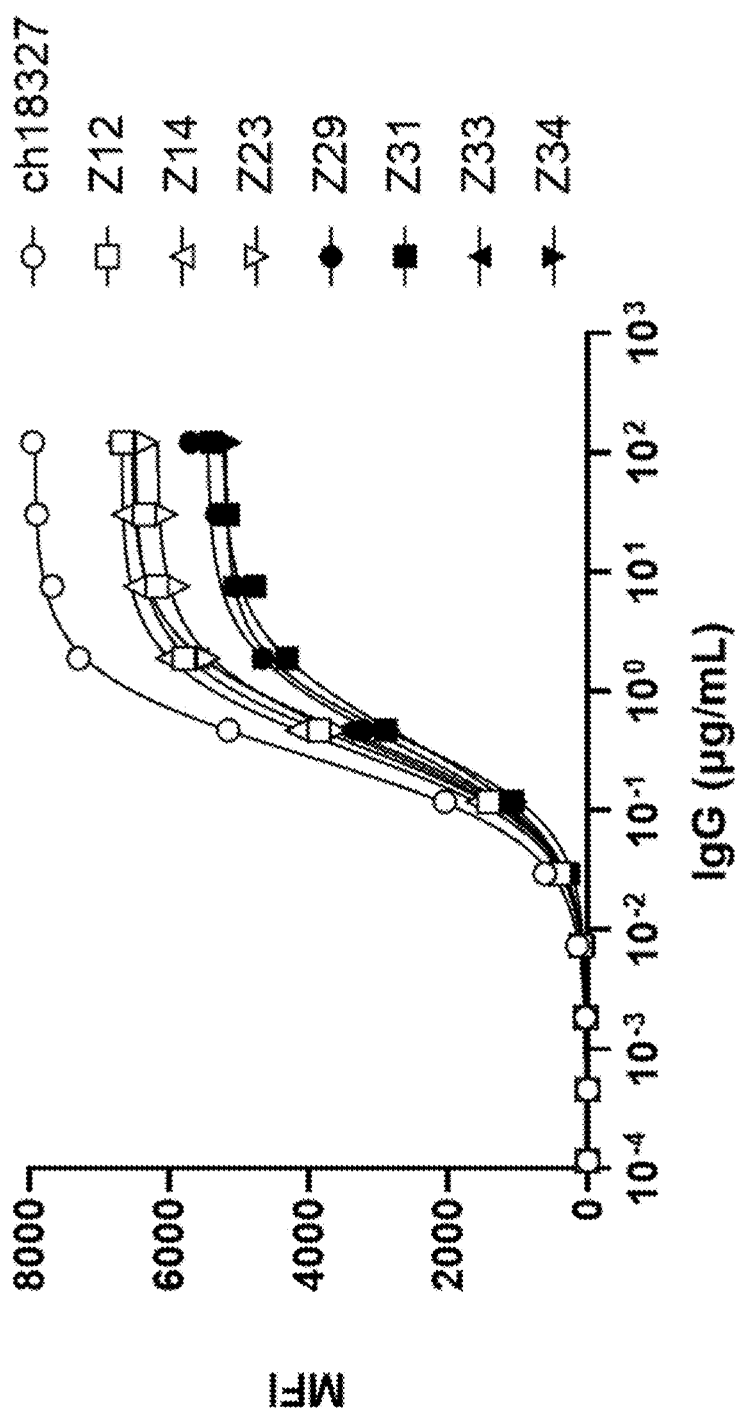
FIG. 15 is a line graph showing binding (MFI) of the listed antibodies to rhesus CMMT cells.

As expected, the binding of the humanized variants to NCI-H520 cells was very similar to the binding of chimeric 18327 (FIG. 14, Table 18). The maximum MFI of the variants was indistinguishable from that of chimeric 18327, while the $EC_{50}$s were all within a 1.5-fold range of one another (3.8 nM-5.5 nM). The binding of the humanized variants to CMMT cells was more variable with some variants displaying a lower maximum MFI than others (FIG. 15, Table 19, compare Z12 versus Z29).

TABLE 18

| $EC_{50}$ Values of Humanized Variants' Binding to NCI-H520 Cells | |
|---|---|
| Ab | $EC_{50}$ (μg/mL) |
| ch18327 | 0.5657 |
| Z12 | 0.6696 |
| Z14 | 0.6351 |
| Z23 | 0.6831 |
| Z29 | 0.6350 |

TABLE 18-continued

| $EC_{50}$ Values of Humanized Variants' Binding to NCI-H520 Cells | |
|---|---|
| Ab | $EC_{50}$ (μg/mL) |
| Z31 | 0.6778 |
| Z33 | 0.8184 |
| Z34 | 0.8246 |

TABLE 19

| $EC_{50}$ Values of Humanized Variants' Binding to CMMT Cells | |
|---|---|
| Ab | $EC_{50}$ (μg/mL) |
| ch18327 | 0.2787 |
| Z12 | 0.3410 |
| Z14 | 0.3101 |
| Z23 | 0.3462 |
| Z29 | 0.3569 |
| Z31 | 0.4057 |
| Z33 | 0.4115 |
| Z34 | 0.3885 |

The $EC_{50}$s for binding to CMMT cells were all within a 1.5-fold range of one another, as was observed with binding to the human tumor cell line NCI-H520. Interestingly, although the binding of the humanized variants to recombinant cynomolgus PTK7 was weaker than their binding to recombinant human PTK7 (see Example 9), binding to the cynomolgus tumor cell line CMMT was approximately 2-fold stronger than binding to the human tumor cell line NCI-H520.

Example 12: Internalization of Humanized Variants on NCI-H520 Cells

The internalization of the chimeric antibody and various humanized constructs on the non-small cell lung carcinoma NCI-H520 tumor cell line was evaluated. Log-phase growing cells were detached using Accutase® (Millipore Sigma) at 37° C., diluted into culture media and collected by centrifugation at 500×g for 3 min. The cells were resuspended in cold 2% FBS in RPMI (binding buffer) at $2\times10^6$ cells/mL. Next, cells were incubated with 30 μg/mL antibody on ice for 30 min. Unbound antibody was removed with three washes using ice-cold 2% FBS in PBS (FACS buffer). Following the last wash, the cells were resuspended in 1 mL ice-cold binding buffer and 100 μL (200,000 cells) was aliquoted for each time point of the internalization time course. The samples were incubated in a water bath at 37° C. for the indicated time. To terminate internalization, the cells were transferred to ice. Subsequently, the cells were collected by centrifugation at 500×g for 3 min at 4° C., the supernatant was aspirated, and the cells were resuspended in 100 μL of secondary antibody (goat anti-human Fc PE, Invitrogen cat. #12-4998-82) diluted 500-fold in binding buffer and were incubated on ice for 30 min. The secondary antibody solution also contained Fixable Viability Dye eFluor™ 780 (Invitrogen) diluted 200-fold. Samples were washed three times with 200 μL of ice-cold FACS buffer and were fixed with 100 μL of 2% paraformaldehyde aqueous solution (PFA) (Electron Microscopy Sciences) at 25° C. (in the dark) for 10 min. The cells were washed two times with 200 μL of FACS buffer, resuspended in 200 u L of 2 mM EDTA in PBS, and were stored at 4° C. in the dark until analyzed by flow cytometry. Antibody binding was quantitated by measuring the PE median fluorescence intensity (MFI) from 10,000 events of viable singlet cells. The binding signal obtained from cells incubated on ice the entire time (time 0) was designated 100% surface binding and internalization was quantitated by measuring the loss of binding signal (MFI) over time following incubation at 37° C.

Figure 16:
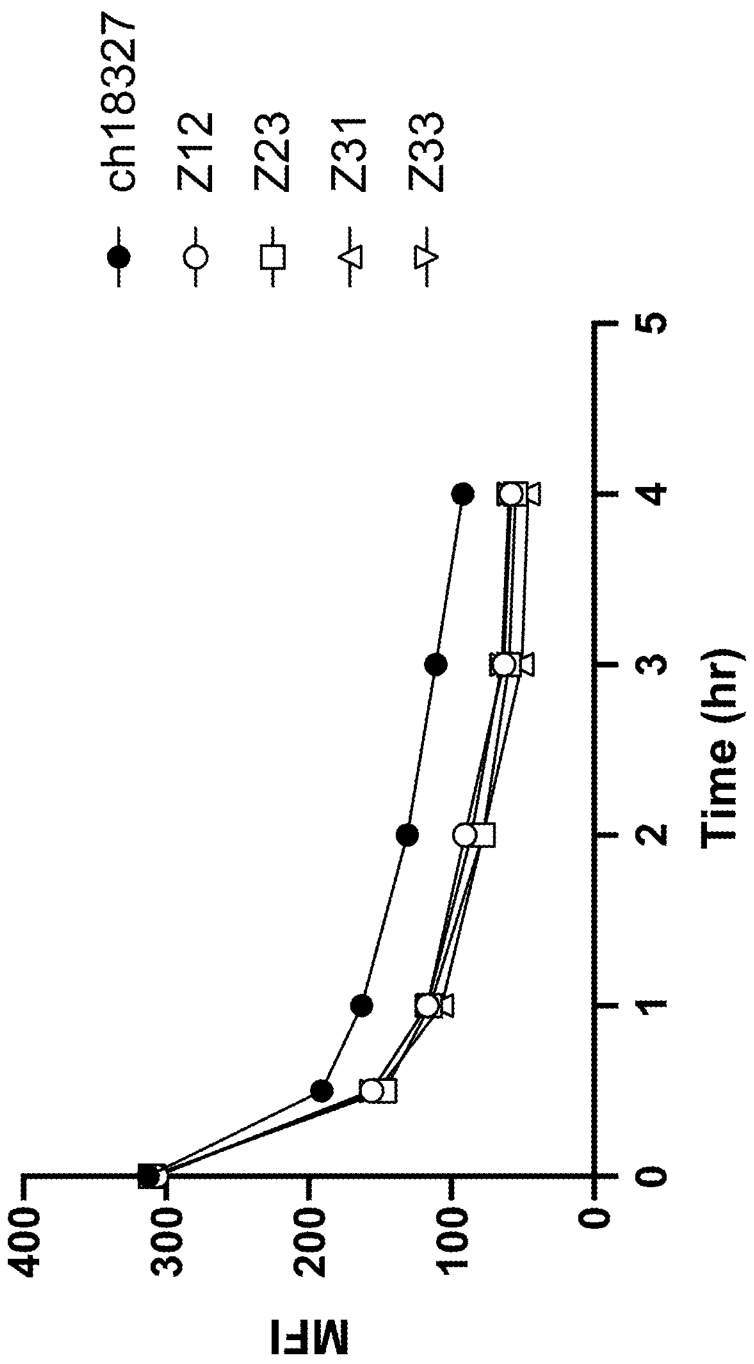
FIG. 16 is a line graph demonstrating the internalization of the listed antibodies in NCI-H520 cells as measured by the loss of surface binding signal over time.

The humanized variants all internalized as well, or better than, chimeric 18327 (FIG. 16), demonstrating that this antibody characteristic was maintained through the humanization process.

Example 13: Developability Studies

The developability of certain humanized variants was characterized by evaluating their serum stability, colloidal stability, stability to freeze/thaw cycles, hydrophobicity, and their response to thermal stress.

In order to assess serum stability, the antibodies were incubated in human serum at 37° C. for 14 days. Subsequently the antibody binding to antigen was characterized by ELISA. Briefly, recombinant human PTK7 was incubated at 1 μg/ml on a microtiter plate at 4° C. overnight. The plate was then blocked with 200 μL/well with 2% BSA in PBS for 1 h at 25° C. Next antibody was diluted serially 5-fold, beginning at 300 nM, and incubated for 2 h at 25° C. Antibody binding was detected with goat anti-human IgG-Fc-HRP diluted 1:5000 and quantitated by incubating with TMB substrate. The reaction was terminated with the addition of 1M HCl and read at $OD_{450}$ on a microtiter plate reader. The maximum $OD_{450}$ and $EC_{50}$ were calculated. No appreciable change in maximum (Max.) $OD_{450}$ nor in $EC_{50}$ was detected over 14 days for Z12, Z23 and Z31, as summarized in Table 20.

TABLE 20

Serum Stability

| | Z12 | | Z23 | | Z31 | |
|---|---|---|---|---|---|---|
| Incubation Time | $EC_{50}$ (nM) | Max. $OD_{450}$ | $EC_{50}$ (nM) | Max. $OD_{450}$ | $EC_{50}$ (nM) | Max. $OD_{450}$ |
| Day 0 | 0.067 | 3.25 | 0.062 | 3.25 | 0.10 | 2.74 |
| Day 1 | 0.068 | 3.25 | 0.062 | 3.23 | 0.086 | 2.76 |
| Day 4 | 0.070 | 3.27 | 0.062 | 3.32 | 0.10 | 2.74 |
| Day 7 | 0.078 | 3.25 | 0.065 | 3.30 | 0.10 | 2.72 |
| Day 14 | 0.077 | 3.26 | 0.074 | 3.31 | 0.086 | 2.76 |
| No treatment | 0.10 | 3.29 | 0.072 | 3.26 | 0.10 | 2.80 |

Next, the propensity of the humanized variants to associate because of weak attractive forces associated with hydrophobic surface residues and/or surface charges was assessed using dynamic light scattering (DLS). DLS was performed using DynaPro® Plate Reader III. Antibodies Z12, Z23 and Z31 were suspended to 2.5, 5, 10, 15 and 20 mg/mL in 45 mM sodium citrate, 135 mM NaCl, 100 mM arginine, 40 mM succinic acid, pH 5.5, transferred into a 1536-well microplate, and five scans of 5 s each were accumulated for each sample. All samples were measured at 25° C. in duplicate wells. The diffusion coefficient was determined using DYNAMICS operation software (v7.8.1.3) and was further plotted against protein concentration to obtain the Diffusion interaction parameter ($k_D$) value. As summarized in Table 21, the $k_D$ of all three humanized variants was ≥−10 (mL/g), consistent with monodisperse size (low propensity to aggregate).

TABLE 21

DLS Characterization

| | Diffusion Interaction Parameter | | Size | Purity (%) at |
|---|---|---|---|---|
| Sample | $k_D$ (mL/g) | $R^2$ | Distribution | 15 mg/mL |
| Z12 | −9.5 | 0.9614 | monodisperse | 98.9 |
| Z23 | −9.7 | 0.9558 | monodisperse | 99.5 |
| Z31 | −9.4 | 0.9879 | monodisperse | 99.2 |

The stability of certain humanized variants subjected to five freeze (−80° C.)/thaw (25° C.) cycles was assessed. Variants Z12, Z23, and Z31 were resuspended at 1 mg/mL in 45 mM sodium citrate, 135 mM NaCl, 100 mM arginine, 40 mM succinic acid, pH 5.5. The protein concentration, purity by SEC-HPLC, and charge distribution by iCIEF were measured before freezing and after five freeze/thaw cycles. No obvious changes in protein concentration, purity and charge distribution were observed for any of the variants, as summarized in FIG. 17.

The relative hydrophobicity of chimeric 18327, Z12, Z23, and Z31 were compared using HIC-HPLC. The variants were resuspended at 1 mg/mL in 45 mM sodium citrate, 135 mM NaCl, 100 mM arginine, 40 mM succinic acid, pH 5.5 and were separated on a Tosoh TSKgel® butyl-NPR (4.6 mm I.D.×10 cm, 2 μm) column using a gradient (flow rate of 0.5 mL/min at 25° C.), as outlined in Table 22. Mobile phase solution A was 25 mM phosphate buffer, pH 7.0 and solution B was 1.5 M $(NH_4)_2SO_4$, 25 mM phosphate buffer, pH 7.0. Z12, Z13 and Z31 all displayed similar retention times (44.6, 44.4, and 44.8 min, respectively), which were longer than chimeric 18327 (36.1 min).

TABLE 22

HIC-HPLC Mobile Phase Gradient Conditions

| Time (min) | % A | % B |
|---|---|---|
| 0 | 0 | 100 |
| 3 | 0 | 100 |
| 53 | 100 | 0 |
| 54 | 0 | 100 |
| 61 | 0 | 100 |

The thermal stability of certain humanized variants incubated for 14 days at either 4° C. or 40° C. was characterized. Variants Z12, Z23, and Z31 were resuspended at 1 mg/mL in 45 mM sodium citrate, 135 mM NaCl, 100 mM arginine, 40 mM succinic acid, pH 5.5. The protein concentration, purity by SEC-HPLC, and charge distribution by iCIEF were measured following the 14-day incubation. No obvious changes in protein concentration were observed following incubation for 14 days at 40° C. versus 4° C. (FIG. 18). There was a small decrease in the monomeric peak and a corresponding small increase in the low molecular weight peak (LMW) in the samples incubated at 40° C., as determined by SEC-HPLC (FIG. 18). With respect to charge variants, Z12, Z23 and Z31 all displayed a decrease in the main peak (with a corresponding increase in the acidic peak content) after the 14-day incubation at 40° C. (FIG. 18).

SEQUENCES

The table below shows sequences described herein (SEQ: SEQ ID NO).

| Description | SEQ | Sequence |
|---|---|---|
| D2D77808-10892 VL | 1 | EIVLTQSPATLSLSPGERAALSCRASQSVSSSYLAWYQQKPGQAPR LLIYGASRRATGIPDRFSGSGSGTDFTLTISRLEPEDFAVYYCQQY GSSPRTFGQGTKVEIR |
| D2D77808-10892 VH | 2 | QVQLQESGPGLVKPSGTLSLTCAVSGGSISSTNWWSWVRQPPGKGL EWIGEIYHSGSTNYNPSLKSRVTISVDKSKNQFSLKLSSVTAADTA VYYCAREDSNYDWFDPWGQGTLVTVSS |
| D2D77808-1105 VL | 3 | DIQMTQSPSSLSASVGDRVTITCQASQDISNYLNWYQQKPGKAPKL LIYDASNLETGVPSRFSGSGSGTDFTFTISSLQPEDIATYYCQQYD NLPFTFGPGTKVDIK |
| D2D77808-1105 VH | 4 | QVQLQESGPGLVKPSETLSLTCTVSGGSVSSGSYYWSWIRQPPGKG LEWIGYIYYSGSTNYNPSLKSRVTISVDTSKNQFSLKLSSVTAADT AVYYCARDRSIAVAGFDYWGQGTLVTVSS |
| D2D77808-11336 VL | 5 | EIVLTQSPATLSLSPGERATLSCRASQSVSNYLAWYQQKPGQAPRL LIYDAYNRATGIPARFSGSGSGTDFTLTISSLEPEDFVVYYCQERS NWPLTFGGGTKVEIK |
| D2D77808-11336 VH | 6 | QVQLVESGGGVVQPGRSLRLSCAASGFTFSSYGMHWVRQAPGKGLE WVAVIWYDGSNKYYADSVKGRFTISRDNSKNTLYLQMNSLRAEDTG VYYCAREFRGYSGYDPDAFDVWGHGTMVTVSS |
| D2D77808-11967 VL | 7 | DIQMTQSPSSLSASVGDRVTITCRASQTISSYLNWYQQKPEKAPKL LIYAASSLQRGVPSRFRGSGSGTDFTLTVSSLQPEDFATYYCQQSY SIPYTFGQGTKLEIK |
| D2D77808-11967 VH | 8 | QVQLQESGPGLVKPSGTLSLTCAVSGGSISSDHWWSWVRQPPGKGL EWIGEIFHSGNTNYNPSLKSRVTISVDKSKNQFSLKLSSVAAADTA VYYCASGYNWNLGYWGQGTLVTVSS |
| D2D77808-1244 VL | 9 | DVVMTQTPLSLPVTLGQPASISCRSSQSLIYSDGNTYLNWFQQRPG QSPRRLIYKVSDRDSGVPDRESGSGSGTDFTLKISRVEAEDVGIYY CMLGTHWPYTFGQGTKLEIK |
| D2D77808-1244 VH | 10 | EVQLVESGGGLVQPGGSLRLSCAASGFTFSSFAMSWVRQAPGKGLE WVSGISGGVGLTYYADSVKGRFTISRDNSKDTLYLQMNSLRAEDTA VFYCAKDQGYSSSSPFDYWGQGTLVTVSS |
| D2D77808-12633 VL | 11 | DIVMTQSPDSLAVSLGERATINCKSSQSVLYSSNNKNYLAWYQQKP GQPPKLLIYWASTRESGVPDRFSGSGSGTDFTLTISSLQAEDVAVY YCQQYYSTPYTFGQGTKLEIK |
| D2D77808-12633 VH | 12 | QVQLVQSGAEVKKPGASVKVSCKASGYTFTSYGISWVRQAPGQGLE WMGWISAYNGNTNYAQKLQGRVTMTTDTSTSTAYMELRSLRSDDTA VYYCAREGWGPFDYWGQGTLVTVSS |
| D2D77808-13587 VL | 13 | EIVLTQSPATLSLSPGERATLSCRASQSVSSSYLAWYQQKPGQAPR LLIYGASSRATGIPDRFSGSGSGTDFTLTISRLEPEDFAVYYCQQY GSSPRTFGQGTKVEIK |
| D2D77808-13587 VH | 14 | EVQLVESGGGLVQPGGSLRLSCAASGFTFSSYAMSWVRQAPGKGLE WVSAISGSGGSTYYADSVKGRFTISRDNSKNTLYLQMNSLRAEDTA VYYCAKDLRYSGSYYLYDAFDIWGQGTMVTVSS |
| D2D77808-3188 VL | 15 | EIVMTQSPATLSVSPGERATLSCRASQSISSNLAWYQQKPGQAPRL LIFGASTRATGIPARFSGSGSGTDFTLTISSLQSEDFAVYYCQQYN NWPYTFGQGTNLEIK |
| D2D77808-3188 VH | 16 | QVQLVQSGAEVKKPGASVKVSCKASGYTFTSYDIIWVRQATGQGLE WMGWMNPNSGNTGYEQKFQGRVTMTRNTSISTAYMELSSLRSEDTA VHYCARGYTNARAEYFQHWGQGTLVTVSS |
| D2D77808-3224 VL | 17 | EIVMTQSPATLSLSPGERATLSCRASQSISNNLAWYQQKPGQAPRL LIYGASTRATGIPARFSDSGSGTEFTLTISSLQSEDFAVYFCQQYH NWPYTFGQGTKLEIK |
| D2D77808-3224 VH | 18 | QVQLQQSGAEVKKPGASVKVSCKASGYIFTSYDINWVRQATGQGLE WMGWMNPNSGNTGYAQKFQGRVTMTMDPSISTAYMELSSLRSEDTA VYFCARGYNNARAEYFQHWGQGTLVTVSS |

-continued

| Description | SEQ | Sequence |
|---|---|---|
| D2D77808-3707 VL | 19 | DIQMTQSPSSLSASVGDRVSITCRASQSISSWLAWYQQKPGKAPKL LIYKASSLESGVPSRFSGSGSGTEFTLTISTLQPDDFATYYCQQYN SYSRTFGQGTKVEIK |
| D2D77808-3707 VH | 20 | EVQLVESGGGVVRPGGSLRLSCAASGFTFDDYGMSWVRQAPGKGLE WVSGINWNGGSTGYVEYVKGRFTISRDNAKNSLYLQMKSVRAEDTA LYYCARDRLGYSYGWGYFDYWGQGTLVTVSS |
| D2D77808-3991 VL | 21 | DIQMTQSPSSLSASVGDRVTITCRASQSISSYLNWYQKKSGKAPKL LIYAASSLQSGVPSRFSGSGSGTDFTLTISSLQPEDFATYYCQQSY SNPWTFGQGTKVEIK |
| D2D77808-3991 VH | 22 | EVQLVESGGGLVQPGGSLRLSCAASGFTFSSYSMNWVRQAPGKGLE WVSYISSSSTTIYYADSVKGRFTISRDNAKNSLYLQMSSLRDEDTA VYYCARVDSRNWNYFFDYWGQGTLVTVSS |
| D2D77808-440 VL | 23 | EIVLTQSPATLSLSPGERAALSCRASQSVSSSYLAWYQQKPGQAPR LLIYGASRRATGIPDRFSGSGSGTDFTLTISRLEPEDFAVYYCQQY GSSPRTFGQGTKVEIK |
| D2D77808-440 VH | 24 | QVQLQESGPGLVKPSGTLSLTCAVSGGSISSTNWWSWVRQPPGKGL EWIGEIYHSGSTNYNPSLKSRVTISVDKSKNQFSLKLSSVTAADTA VYYCAREDSNYDWFDPWGQGTLVTVSS |
| D2D77808-4647 VL | 25 | DIQMTQSPSSLSASVGDRVTITCRASQTISSWLAWYQQKPGKAPKL LIYKASTLEGGVPSRFSGSGSGTEFTLTISSLQPDDFATYYCQQYN IYSRTFGQGTKVEIK |
| D2D77808-4647 VH | 26 | EVQLVESGGGVVRPGGSLRLSCAASGFTFDDYGMSWVRQAPGKGLE WVSGINWNGGSTGYVDSVKGRFTFSRDNAKNSLYLQMNSLRAEDTA LYYCARDRLGYSYGWGYFDYWGQGTLVTVSS |
| D2D77808-4992 VL | 27 | DIQMTQSPSSLSASVGDRVTITCRASQDISNYLAWYQQKPGKVPNL LIYAASTLQSGVPSRFSGSGSGTDFTLTISSLQPEDVATYYCQKYN SAPLTFGGGTKVEIK |
| D2D77808-4992 VH | 28 | EVQLVESGGGLVKPGGSLRLSCAASGFTFSNAWMNWVRQAPGKGLE WVGRIKSKTDAGTTDYAAPVKGRFTISRDDSKNTLYLQMNSLKTED TAVYYCPTGWNYHAFDIWGQGTMVTVSS |
| D2D77808-5632 VL | 29 | DIQMTQSPSSLSASVGDRVTITCRASQSISSWLAWYQQKPGKAPKL LIYKASSLESGVPSRFSGSGSGTEFTLTISSLQPDDFETYYCQQYN SYSRTFGQGTKVEIK |
| D2D77808-5632 VH | 30 | EVQLVESGGGVVRPGGSLRLSCAASGFTFDDYGMSWVRQAPGKGLE WVSGINWNGGSTGYVDSVKGRFIFSRDNAKNSLYLQMNSLRAEDTA LYYCARDRLGYSYGWGYFDYWGQGTLVTVSS |
| D2D77808-7380 VL | 31 | DIQMTQSPSSLSASVGDRVTITCRASQSISSWLAWYQQKPGKAPKL LIYKASSLESGVPSRFSGSGSGTEFTLTISSLQPDDFATYYCQQYN SYSRTFGQGTKVEIK |
| D2D77808-7380 VH | 32 | EVQLVESGGGVVRPGGSLRLSCEASGFTFDDYGMSWVRQAPGKGLE WVSGINWNGGSTGYVEYVKGRFTISRDNAKNSLYLQMKSVRAEDTA LYYCARDRLGYSYGWGYFDYWGQGTLVTVSS |
| D2D77808-7683 VL | 33 | DIQMTQSPSSLSASVGDRVSITCRASQSISSWLAWYQQKPGKAPKL LIYKASSLESGVPSRFSGSGSGTEFTLTISTLQPDDFATYYCQQYN SYSRTFGQGTKVEIK |
| D2D77808-7683 VH | 34 | EVQLVESGGGVVRPGGSLRLSCAASGFTFDDYGMSWVRQAPGKGLE WVSGINWNGGSTGYVEYVKGRFTISRDNAKNSLYLQMKSVRAEDTA LYYCARDRLGYSYGWGYFDYWGQGTLVTVSS |
| D2D77808-843 VL | 35 | EIVMTQSPATLSVSPGERATLSCRASQSVSSNLAWYQQKPGQAPRL LIYGASTRATGIPARFSGSGSGTEFTLTFSSLQSEDFAVYSCQHYN DWPYTFGQGTNLEIK |
| D2D77808-843 VH | 36 | QVQLVQSGAEVKKPGASVKVSCKASGYTFISYDINWVRQATGQGLE WMGWMNPNSGNTGYAQKFQGRVTMTRKTSISTAYMELSSLRSEDTA VYYCARGYTYARAEYFHPWGQGTLVTVSS |
| D2D77808-9018 VL | 37 | DIQMTQSPSSLSASVGDRVTITCRASQSIAIYLNWYQQRPGKPPKL LIFTASSLQSGVPSRFTGSGSGTDFTLSISSLQPEDFATYYCQQSY STPPTFGQGTKVEIK |

-continued

| Description | SEQ | Sequence |
|---|---|---|
| D2D77808-9018 VH | 38 | QVQLVQSGAEVKKPGASVKVSCRASGYTFTDYFIHWVRQAPGQGLEWMGWISPNSGGTNYAQKFQGRVTMTRDTSITTAYMELSSLTSDDTAVYYCARYDYDGYSGWFDPWGQGTLVTVSS |
| D2D77808-9100 VL | 39 | DIQMTQSPSSLSASVGDRVTITCRASQGISNYLAWYQQKPGKVPKLLIYAASTLQSGVPSRFSGSGSGTDFTLTISSLQPEDVATYYCQKYNSAPRTFGQGTKVEIK |
| D2D77808-9100 VH | 40 | QVQLVQSGAEVKKPGASVKVSCKASGYTFTGYYMHWVRQAPGQGLEWMGWINPNSGGTNYAQKFQGRVTMTRDTSISTVYMEVSRLRSDDAAVYYCAREGQMTHASDIWGQGTMVTVSS |
| D2D77812-3278 VL | 41 | DIQMTQSPSSLSASVGDRVTITCQASQDISNYLHWYQQKPGKAPELLIYDASNLETGVPSRFSGSGSGTDFTFTIGSLQAEDIATYYCQQYDHLPTFGGGTKVEIK |
| D2D77812-3278 VH | 42 | EVQLVESGGGVVRPGGSLRLSCAASGFTFDDYDMSWVRQAPGKGLEWVSGINWNGGSTGYADSVKGRCTISRDNAKNSLYLQMNSLRAEDTALYHCAREKYSSSSWAFDIWGQGTMVTVSS |
| D2D77812-3529 VL | 43 | DIQMTQSPSSLSASVGDRVIITCQASQDITNYLNWYQQRPGKAPKLLIYDASNLETGVPSRFSGSGSGTDFTFIISSLQPEDIATYYCQQYDNLPITFGQGTRLEIK |
| D2D77812-3529 VH | 44 | EVQLVESGGGLVQPGGSLKLSCAASGFTFSGFAMHWVRQASGKGLEWIGRIRSKANNYATAYAASAKGRFTISRDDSKNTAYLQMNSLKTEDTAVYYCTSSGYSYGYLFFDYWGQGTLVTVSS |
| D3D88750-10931 VL | 45 | DIVLTQSPASLAVSLGQRATISCRASESVDNYGISFMNWFQQKPGQPPKLLIYAASIQGSGVPARFSGSGSGTDFSLNIHPMEEDDTAMYFCQQSKEVPRTFGGGTKLEIK |
| D3D88750-10931 VH | 46 | QVQLQQSGAELAKPGASVKLSCRASGYTFIRYWMHWVKQRPGQGLEWIGYINPSTDYTEYNQKFKDKATLTADKSSSTAYMQLSSLTYEDSAVYYCARSYLDYWGQGTTLTVSS |
| D3D88750-15061 VL | 47 | QAVVTQESALTTSPGETVTLTCRSSTGAVTTSNYANWVQEKPDHLFTGLIGGTNNRAPGVPARFSGSLIGDKAALTITGAQTEDEAIYFCALWYSNHWVFGGGTKLTVL |
| D3D88750-15061 VH | 48 | QVQLQQPGAELVRPGSSVKLSCKASGYTFTSYWMHWVKQRPIQGLEWIGNIDPSDSETHYNQKFKDKATLTVDKSSSTAYMQLSSLTSEDSAVYYCASYDGYTDWYFDVWGTGTTVTVSS |
| D3D88750-17170 VL | 49 | QAVVTQESALTTSPGETVTLTCRSSTGAVTTSNYANWVQEKPDHLFTGLIGGTNNRAPGVPARFSGSLIGDKAALTITGAQTEDEAIYFCALWYSNHWVFGGGTKLTVL |
| D3D88750-17170 VH | 50 | QVQLQQPGAELVKPGASVKLSCRASGYSFTSYWMLWVKQRPGQGLEWIGMIHPNSGSTNFNEQFRSKATLTVDKSSSTAYIQLSSLTSEDSAVYYCARLDYYGSIEHFDYWGQGTTLTVSS |
| D3D88750-2823 VL | 51 | DIQMTQSSSYLSVSLGGRVTITCKASDHINNWLVWYQQKPGNAPRLLISGATSLETGVPSRFSGSGSGKDYTLSITSLQTEDVATYYCQQYWSTPYTFGGGTKLEIK |
| D3D88750-2823 VH | 52 | QVQLQQPGAELVRPGSSVKLSCKASGYTFTSYWMHWVKQRPIQGLEWIGNIDPSDNKSHYNKKFKDKATLTVDKSSSTAYMQLSSLTSEDSAVYYCARGGLTGTPRFGYWGQGTLVTVSA |
| D3D88750-7308 VL | 53 | DIQMTQTPSSLSASLGDRVTISCRASQDIRNYLNWYQQKPDGTVKLLIYYTSRLHSGVPSRFSGSGSGTDYSLTISNLEQEDIATYFCQQGNTLPPTFGGGTKLEIK |
| D3D88750-7308 VL | 54 | QVQLQESGPGLVKPSQSLSLTCSVTGYSITSGYYWNWIRQFPGNRLEWMGYISYDGNNNYNPSLKNRISITRDTSKNQFFLKLNSVTTEDTATYYCAKDFYRRWGAMDYWGQGTSVTVSS |
| D3D88750-8482 VL | 55 | DIVLTQSPASLAVSLGQRATISCRASQSVSTSSYSYMHWYQQKPGQPPKLLIKYASNLESGVPARFSGSGSGTDFTLNIHPVEEVDTAAYYCQHSWEIPYTFGGGTKLEIK |
| D3D88750-8482 VH | 56 | QVQLQQSGAGLARPGTSVKLSCKASGYTFTSFGISWVKQRPGQGLEWIGEIYPRRGNTLYNEQFKGKATLTADKSSSTAHMELRSLTSEDSAVYFCAREGAYSNHYAFDYWGQGTSVTVSS |

-continued

| Description | SEQ | Sequence |
|---|---|---|
| D3D88936-10726 VL | 57 | DIVLTQSPSSLSASLGERVSLTCRASQEISGYLSWLQQKPDGTIKR LIYAASTLDSGVPKRFSGSRSGSDYSLTISSLESEDFADYYCLQYA SYPYTFGGGTKLEIK |
| D3D88936-10726 VH | 58 | QVQLQQSGAELVRPGASVKLSCTASGFNIKDDYMHWVKQRPEQGLE WIGWIDPENGDTEYASKFQGKATITADTSSNTAYLQLSSLTSEDTA VYYCTTDYGNNWYFDVWGTGTTVTVSS |
| D3D88936-12014 VL | 59 | DIQMTQSPSSLSASLGDTITITCHASQNINVWLSWYQQKPGNIPKL LIYKASNLHTGVPSRFSGSGSGTGFTLTISSLQPEDIATYYCQQGQ SYPFTFGSGTKLEIK |
| D3D88936-12014 VH | 60 | QVQLQQSGAELAKPGASVKLSCKASGYTFTSYWMHWVKQRPGQGLE WIGYINPSSGYTKYNQKFKDKATLTADKSSSTAYMQLSSLTYEDSA VYYCARSYFDYWGQGTTLTVSS |
| D3D88936-13864 VL | 61 | DIVLTQSPASLAVSLGQRATISCRASESVDNYGISFMNWFQQKPGQ PPKLLIYAASNQGSGVPARFSGSGSGTDFSLNIHPMEEDDTAMYFC QQSKEVPFTFGSGTKLEIK |
| D3D88936-13864 VH | 62 | QVQLQQPGAELVKPGASVKLSCRASGYTFTTYWMHWVKQRPGRGLE WIGWIDPNSGTTKYNEKFKSKTTLTVDKPSSTAYMQLNSLTSEDSA VYYCARGDSNYDYFDYWGQGTTLTVSS |
| D3D88936-14075 VL | 63 | QAVVTQESALTTSPGETVTLTCRSSTGAVTTSNYANWVQEKPDHLF TGLIGGTNNRAPGVPARFSGSLIGDKAALTITGAQTEDEAIYFCAL WYSNHWVFGGGTKLTVL |
| D3D88936-14075 VH | 64 | QVQLQQSGAELVRPGASVKLSCTASGFNIKDDYMHWVKQRPEQGLE WIGWIDPENGDTEYASKFQGKATITADTSSNTAYLQLSSLTSEDTA VYYCTTDYGSSFSWFAYWGQGTLVTVSA |
| D3D88936-14742 VL | 65 | DIVLTQSPASLAVSLGQRATISCRASESVDNYGISFMNWFQQKPGQ PPKLLIYAASNQGSGVPARFSGSGSGTDFSLNIHPMEEDDTAMYFC QQSKEVPWTFGGGTKLEIK |
| D3D88936-14742 VH | 66 | QVQLQQSGAELMRPGASVRLSCTASGFDIKDYYLHWVKQRPDQGLE WIGRIDPEDGDTEYAPNFQGAATMTADTSSNTAYLHLNSLTSGDTA VYYCSRTGTRWIAYWGQGTLVTVSA |
| D3D88936-14768 VL | 67 | DIVLTQSPASLAVSLGQRATISCRASESVDNYGISFMNWFQQKPGQ PPKLLIYAASNQGSGVPARFSGSGSGTDFRLNIHPMEEDDTAMYFC QQSKEIPWTFGGGTKLEIK |
| D3D88936-14768 VH | 68 | QVQLQQSGAELVKPGASVKLSCTASDFNIKDFYIHWVKLRTEQGLE WIGRIDPEDGETKYAPKFQGKATITADTSSNTAYLQLSSLTSEDTA VYYCARASSGPWFAYWGQGTLVTVSA |
| D3D88936-15092 VL | 69 | DIVMTQSPSSLSASLGDTITITCHASQNINLWLSWYQQKPGNIPKL LISKASNLHTGVPSRFSGSGSGSGFTLTISSLQPEDIATYYCQQGQ SYPFTFGSGTKLEIK |
| D3D88936-15092 VH | 70 | QVQLQQSGAELAKPGASVRLSCKASGYTFTRYWMHWLKQRPGQGLE WIGYINPSSGYTEYNQNFKDKATLTADKSSSTAYMQLSSLTYEDSA VYYCARSYFDVWGTGTTVTVSS |
| D3D88936-16478 VL | 71 | QAVVTQESALTTSPGETVTLTCRSSTGAVTTSNYANWVQEKPDHLF TGLIGGTNNRAPGVPARFSGSLIGDKAALTITGAQTEDEAIYFCAL WYSNHWVFGGGTKLTVL |
| D3D88936-16478 VH | 72 | QVQLQQSGAELVRPGASVKLSCTASGFNIKDDYMHWVKQRPEQGLE WIGWIDPENGDTEYASKFQGKATITADTSSNTAYLQLSSLTSEDTA VYYCTTSKNYYGSSFFFDYWGQGTTLTVSS |
| D3D88936-17701 VL | 73 | DIVMTQSPATLSVTPGDRVSLSCRASQSISDYLHWYQQKSHESPRL LIKYASQSISGIPSRFSGSGSGSDFTLSINSVEPEDVGVYYCQNGH SFPWTFGGGTKLEIK |
| D3D88936-17701 VH | 74 | QVQLQQSGPELVKPGASVKISCKASGYAFSSSWMNWVKQRPGKGLE WIGRIYPGDGDTNYNGKFKGKATLTADKSSSTAYMQLSSLTSEDSA VYFCARGGGTWFAYWGQGTLVTVSA |
| D3D88936-18327 VL | 75 | DIQMTQSPSSLSASLGERVSLTCRASQEISGYLSWLQQKPDGTIKR LIYAASTLDSGVPKRFSGSRSGSDYSLTISSLESEDFANYYCLQYA TYPFTFGSGTKLEIK |

-continued

| Description | SEQ | Sequence |
|---|---|---|
| D3D88936-18327 VH | 76 | QVQLQQPGAELVKPGASVKLSCKASGYTFTTYWMHWVKQRPGQGLE WIGEIDPSDSYTTYNQKFTGKATLTVDTSSSTAYMQLSSLTSEDSA VYFCLLPAWFGYWGQGTLVTVSA |
| D3D88936-19853 VL | 77 | DILLTQSPAILSVSPGERVSFSCRASQSIGTSIHWYQQRTNGSPRL LIKYASESISGIPSRFSGSGSGTDFTLSINSVESEDIADYYCQQSN SWPTTFGGGTKLEIK |
| D3D88936-19853 VH | 78 | EVQLQQSDAELVKPGASVKISCKVSGYTFTDHTIHWMKQRPEQGLE WIGYIYPRDGSTKYNEKFKGKATLTADKSSSTAYMQLNSLTSEDSA VYFCAIYRRGFAYWGQGTLVTVSA |
| D3D88936-6283 VL | 79 | DIVMTQSPSSLTVTAGEKVTMSCKSSQSLLNSGNQKNYLTWYQQKP GQPPKLLIYWASTRESGVPDRFTGSGSGTDFTLTISSVQAEDLAVY YCQNDYSYPLTFGAGTKLELK |
| D3D88936-6283 VH | 80 | EVQLQQSDAELVKPGASVKISCKVSGYTFTDHTIHWMKQRPEQGLE WIGYIYPRDGSTKYNEKFKGKATLTADKSSSTAYMQLNSLTSEDSA VYFCAFYYYGFAYWGQGTLVTVSA |
| D3D88936-762 VL | 81 | QAVVTQESALTTSPGETVTLTCRSSTGAVTTSNYANWVQEKPDHLF TGLIGGTNNRAPGVPARFSGSLIGDKAALTITGAQTEDEAIYFCAL WYSNHWVFGGGTKLTVL |
| D3D88936-762 VH | 82 | QVQLQQSGAELVRPGASVKLSCTASGFNIKDDYMHWVKQRPEQGLE WIGWIDPENGDTEYASKFQGKATITADTSSNTAYLQLSSLTSEDTA VYYCTTYYYGSSDFAYWGQGTLVTVSA |
| D4D88750-10662 VL | 83 | DIVMTQTPLSLPVTPGEPASISCRSSQSLLHSNEYNYLDWYLQKPG QSPQLLIYLGSNRASGVPDRFSGSGSVTDFTLKISRVEADDLGVYY CMQALQTPYTFGQGTKLEIK |
| D4D88750-10662 VH | 84 | EVQLVESGGGVVQPGGSLRLSCATSGFTFSSYTMNWVRQAPGKGLE WVSCISSSGSAIYFADSVKGRFAISRDNVKNSLYLQMNSLRDEDTA VYYCARGGYSSSSRYHDAFDIWGQGTMVTVSS |
| D4D88750-11630 VL | 85 | EIVVTQSPATLSLSPGERATLSCRASQSVSSSYLAWYQQKPGQAPR LLIYGTSSRATGIPDRFSGSGSGTDFTLIITRLEPEDFVVYYCQQY GTSPRTFGQGTKVEIK |
| D4D88750-11630 VH | 86 | QVQLQESGPGLVKPSGTLSLTCAVSGGSISSINWWSWVRQPPGKGL EWIGEIYHSGSTNYNPSLKSRVTISVDKSKNQFSLKLSSMTAADTA VYYCARDESGYDYFDYWGQGTLVTVSS |
| D4D88750-13229 VL | 87 | DIVMTQSPDSLAVSLGERATINCKSSQNVLYSSNNENYLAWYQQKP GQPPNLLIYWASTRESGVPDRFSGSGSGTDFTLTISSLQAEDVAVY YCQQYYSTPPTFGGGTKVEIK |
| D4D88750-13229 VH | 88 | QVQLVESGGGVVQPGRSLRLSCAASGFTFSSYGMHWVRQAPGKGLE WVAVIWYDGGNKYYADSVKGRFIISRDNSRDTLYLQMNSLRAEDTA VYYCARDWGSSWYLFDHWGQGTLVTVSS |
| D4D88750-13354 VL | 89 | DIQMTQSPSSLSASVGDRVTITCRASQSISNFLNWYQQRPGKVPKL LINAASSLQSGVPSRFSGRGSGTDFTLTIGSLQPEDFATYYCQQSY ITPLTFGGGTKVEIK |
| D4D88750-13354 VH | 90 | EVQLVESGGGLVQPGGSLRLSCAASGFTFSSYDMHWVRQPTGKGLE WVSSIGTAGNTNYPGSVKGRFTISRENAKNSLYLQMNSLRAGDTAV YYCARWVNWYFGLWGRGTLVTVSS |
| D4D88750-13531 VL | 91 | DIVMTQSPDSLAVSLGERATIDCKSSQNVLYSSNNKNYLAWYQQKP GQPPKLIIYWASTRESGVPDRFSGSGSGTDFTLTITSLQAEDVAIY YCQQYYSTPLTFGGGTKVEIK |
| D4D88750-13531 VH | 92 | QVQLQESGPGLVKPSQTLSLTCTVSGGSFSSGGYYWSWIRQHPGKG LEWIGYIYYSGTTYYTPSLKSRITISVDTSENQFSLKLNSVTAADT AVYYCARAGFGYYYMDVWGKGTTVTVSS |
| D4D88750-16740 VL | 93 | EIVLTQSPATLSLSPGERATLSCRASQSVSSSYLAWYQQKPGQAPR LLIYGASSRATGIPDRFSGSGSGTDFTLTISRLEPEDFAVYYCQQY GSSPRTFGQGTKVEIK |
| D4D88750-16740 VH | 94 | EVQLVESGGGLVQPGGSLRLSCAASGFTFSSYAMSWVRQVSGKGLE WVSAISGTGGNIYYTDSVQDRFTISRDNFKKTLYLHMNSLRAEDTA VYYCAKSSYSGNFHVEDFWGQGTLVTVSS |

-continued

| Description | SEQ | Sequence |
|---|---|---|
| D4D88750-16804 VL | 95 | EIVLTQSPATLSLSPGERATLSCRASQSVSSSYLAWYQQKPGQAPR LLIYGASSRATGIPDRFSGSGSGTDFTLTISRLEPEDFAVYYCQQY GSSYTFGQGTKLEIK |
| D4D88750-16804 VH | 96 | QVQLVQSGAEVKKPGASVKVSCKASGYTFTSYDINWVRQATGQGLE WMGWMNPNSGNTGYAQKFQGRVTMTRNTSISTAYMEMSSLRYEDTA VYYCARRRLYNWNWGWFDPWGQGTLVTVSS |
| D4D88750-19223 VL | 97 | DIVMTQSPDSLAVSLGERATINCKSSQSVLYSSNNKNYLAWYQQKP GQPPKLLIFWASTRESGVPDRFSGSGSGTDFTLTISSLQAEDVAVY YCQQYYSTPPTFGGGTKVEIK |
| D4D88750-19223 VH | 98 | EVQLVESGGGLVQPGRSLRLSCAASGFTFDDYAMHWVRQAPGKGLE WVSGISWNRGSIDYADSVKGRFTISRDNAKNSLYLQMNSLRAEDTA LYYCAKDIGITGTTEAFDIWGQGTMVTVSS |
| D4D88750-19685 VL | 99 | DIQMTQSPSSLSASVGDRVTITCRASQGINIWLAWYQQKPGKAPKL LIYAASSLQSGVPSRFSGSGSGTDFTLTISSLQPEDFATYYCQQAN SFPITFGQGTRLEIK |
| D4D88750-19685 VH | 100 | QVQLQESGPGLVKPSQTLSLTCTVSGGSISSGGYYWSWIRQHPGKG LEWIGYIYYSGNTYYNPSLKSRVAISVGTSKNQFSLKLSSVTAADT AVYYCARGGYYYGPGSYGDNSSGYYYFDYWGQGTLVTVSS |
| D4D88750-2830 VL | 101 | EIVLTQSPATLSLSPGERAILSCRASQSVSIYLAWYQQKPGQAPRL LIYDASDRATGIPARFSGSGSETDFTLTISSLEPEDFAVYYCQQRN NWPLTFGGGTKVEIK |
| D4D88750-2830 VH | 102 | EVQLVESGGGLVQPGGSLRLSCAASGFTFSSYAMSWVRQVSGKGLE WVSAISGTGGNIYYTDSVQDRFTISRDNFKKTLYLHMNSLRAEDTA VYYCAKSSYSGNFHVFDFWGQGTLVTVSS |
| D4D88750-4395 VL | 103 | EIVLTQSPATLSLSPGERATLSCRASQSVSSSYLAWYQQKTGQAPRL LIYDASDRATGIPARFSGSGSGTDFTLTISSLEPEDFAVYYCQQRG NWPLTFGGGTKVEIK |
| D4D88750-4395 VH | 104 | EVQLVESGGDLVQPGGSLRLSCAASGFSFSGYAMSWVRQVPGKGLE WVSAISGSGGNTYYADSVKGRFTISRDNSKNTLYLQMNSLRAEDTA VYYCAKSSLSGNFHVFDFWGQGTLVTVSS |
| D4D88750-4746 VL | 105 | EIVMTQSPATLSVSPGERATLSCRASQSVSSNLAWYQQKPGQAPRL LIYGASTRATGIPARFSGSGSGTEFTLTISSLQSEDFAVYYCQQYN NWPLTFGGGTKVEIK |
| D4D88750-4746 VH | 106 | QVQLQESGPGLVKPSQTLSLTCAISGDSVSTNSAAWNWIRQSPSRG LEWLGRTYYRSKWYNDYAVSVTSRITINPDTSKNQFSLQLNSVTPE DTAVYYCARDWWELIFFDYWGQGTLVTVSS |
| D4D88750-7698 VL | 107 | EIVLTQSPATLSLSPGERATLSCRASQSVSSYLAWYQQKPGQAPRL LIYDASNRATGIPARFSGSGSGTDFTLTISSLEPEDFAVYYCQQRS NSITFGQGTRLEIK |
| D4D88750-7698 VH | 108 | EVQLVESGGGLVKPGGSLRLSCAASGFTFSSYSMNWVRQAPGKGLE WVSSISSSTSYRYYADSVKGRFTISRDNAKNSLYLQMNSLRAEDTA VYYCARESGGVTNNWFDPWGQGTLVTVSS |
| D4D88750-9185 VL | 109 | DIVMTQSPDSLAVSLGERATITCKSSQNVLYNSNNKNYLAWYQQKP GQPPKLLIYWASTRESGVPDRFSGSGSGTDFTLTISSLQAEDVAVY CCQQYYSIPYTFGQGTKVEIK |
| D4D88750-9185 VH | 110 | EVQLVESGGGLVKPGGSLRLSCVVSGFTFSRFTMNWVRQAPGKGLE WVSSISTSSSYIYYGDSVKGRFTISRDNAKNSLHLQMNSLRAEDTA VYYCAREGGDWNHDYNYYYMDVWGKGTTVTVSS |
| D4D88750-935 VL | 111 | DIVMTQSPDSLAVSLGERATVTCKSSQNVLYNSNNKNYLAWYQQKP GQPPNLLIYWASTRESGVPDRFSGSGSGTDFTLTISSLQAEDVAIY YCQQYYSTPYTFGQGTKLEIK |
| D4D88750-935 VH | 112 | EVQLVESGGGLVKPGGSLRISCVVSGFTFSRFTMNWVRQAPGKGLE WVSSISSTSSYVYYGDSVKGRFTISRDNAKNSLYLQMNSLRAEDTA VYYCAREGGDWNYDYNYYYMDVWGKGTTVTVSS |
| D4D88936-1008 VL | 113 | DIQMTQSPSSVSASVGDRVTITCRASQGISSWLAWYQQKPGKAPKL LIYEASSLQSGVPSRFSGSGSGTDFTLTISSLQPEDFATYYCQQDN SFPFTFGPGTKVDIK |

-continued

| Description | SEQ | Sequence |
|---|---|---|
| D4D88936-1008 VH | 114 | QVQLVQSGSELKKPGASVKVSCKASGYTFTSYAMNWVRQAPGQGLE WMGWINTNTGNPTYAQGFTGRFVFSLDTSVSTAYLQISSLKAEDTA VYYCARSLYWYFDLWGRGTLVTVSS |
| D4D88936-10730 VL | 115 | DIQMTQSPSSLSASVGDRVTITCQANQDITNYLNWYQQKPGKAPKL LIYDASNLETGVPSRFSGSGSGTDFTFTISSLQPEDIATYYCQQYD NLPLTFGGGTKVEIK |
| D4D88936-10730 VH | 116 | EVQLVESGGGLVQPGGSLKLSCAASGFTFSGSAMDWVRQASGKGLE WVGRIRSKANNYATAYAASVKGRFTISRDDSKNTAYLQMNSLKTED TAVYYCTSRGYSGYDLFDYWGQGTLVTVSS |
| D4D88936-12394 VL | 117 | DIQMTQSPSSLSASVGDRVTITCQASQDISNYLNWYQQKPGKAPKV LIYDASNLETGVPSRFSGSGSGTDFTFTISSLQPEDIATYYCQQYD NLPLTFGGGTKVEIK |
| D4D88936-12394 VH | 118 | EVQLVESGGGLVQPGGSLKLSCAASGFTFSGSAMHWVRQASGKGLE WVGRIRSKANSYATAYAASVKGRFTISRDDSKNTAYLQMNSLKTED TAVYYCTSRGYSGYDYSSYFDYWGQGTLVTVSS |
| D4D88936-1474 VL | 119 | EIVLTQSPATLSLSPGERATLSCRASQSFSSSYLAWYQQKPGQVPR LLIYGASSRATGIPDRFSGSGSGTDFTLTISRLEPEDFAVYYCQQY GSSPYTFGQGTKLEIK |
| D4D88936-1474 VH | 120 | QVQLQESGPGLVKPSGTLSLTCAVSGGSISSSDWWSWVRQPPGKGL EWLGEIHHSGNTNYNPSLKSRVTISVDKSKNHFSLKLRSVTAADTA VYYCARLYSDGYNYYYYMDVWGKGTTVTVSS |
| D4D88936-14748 VL | 121 | DIQMTQSPSSLSASVGDRVTITCQASQDISNYLNWYQQKPGKAPKV LIYDASNLEKGVPSRFSGSGSGTDFTFTISSLQPEDIGTYYCQQYD NLPITFGGGTKVEIK |
| D4D88936-14748 VH | 122 | EVQLVESGGGLVQPGGSLKLSCAASGFTFSGSAMHWVRQASGKGLE WIGRIRSKANNDATSYDASVKGRFTISRNDSKNTAYLQMNSLKTED TAVYYCTSRGYSGYDYSSYFDYWGQGTLVTVSS |
| D4D88936-15106 VL | 123 | EIVLTQSPATLSLSPGERATLSCRASQSVSSNFLAWYQQKPGQAPR LLIYGASSRATGIPDRFSGSGSGTDFTLTISRLEPEDFAVYYCQQY GNSPWTFGQGTKVEIK |
| D4D88936-15106 VH | 124 | QVQLQESGPGLVKPSQTLSLTCAISGDSVSSNSAAWNWIRQSPSRG LEWLGRTYYRSKWYNDYAVSVKGRIAINPDTSKNHFSLQLTSVTPE DTAVYYCARDPRFTWNYGAFDIWGQGTMVTVSS |
| D4D88936-16655 VL | 125 | DIQMTQSPSSLSASVGDRVTITCQASQDISNYLNWYQQKPGKAPKV LIYDASNLETGVPSRFSGSGSGTDFTFTISSLQPEDIATYYCQQYD NVPLTFGGGTKVEIK |
| D4D88936-16655 VH | 126 | EVQLVESGGGLVQPGGSLKLSCAASGFTFSGSAMHWVRQASGKGLE WVGRIRSKANNYATAYAASVKVRFTISRDDSMTTAYLHMNSLKTED TAVYYCTSRGFSGYDYSSYFDYWGQGTLVTVSS |
| D4D88936-3188 VL | 127 | DIQMTQSPSSLSASVGDRVTITCQASQDIRNYLNWYQQKPGKAPKL LIYDASNLETGVPSRFSGSGSGTDFTFTISSLQPEDIATYYCQPYD NLMYTFGGGTKVEIK |
| D4D88936-3188 VH | 128 | EVQLVESGGGLVQPGGSLRLSCAASGFTFSSYDMHWVRQATGKGLE WVSGINTDGDTFYPGSVKGRFTISRENAKNSLYLQMNSLRAGDTAV YYCARRGWNYGFDYWGQGTLVTVSS |
| D4D88936-5708 VL | 129 | DIQMTQSPSSLSASVGDRVTITCQANQDITNYLNWYQQKPGKAPKL LIYDASNLETGVPSRFSGSGSGTDFTFTISSLQPEDIATYYCQQYD NLPLTFGGGTKVEIK |
| D4D88936-5708 VH | 130 | EVQLVESGGGLVQPGGSLKLSCAASGFTFSGSAMDWVRQASGKGLE WVGRIRSKANNYATAYAASVKGRFTISRDDSKNTAYLQMNSLKTED TAVYYCTSRGYSGYDLFDYWGQGTLVTVSS |
| D4D88936-5760 VL | 131 | DIQMTQSPSSLSASVGDRVTITCQASQDISNYLNWYQQKPGKAPKV LIYDASNLETGVPSRFSGSGSGTDFTFTISSLQPEDIATYYCQQYD NLPLTFGGGTKVEIK |
| D4D88936-5760 VH | 132 | EVQLVESGGGLVQPGGSLKLSCAASGFTFSGSAMHWVRQASGKGLE WVGRIRSKANNYATAYAASVKGRFTISRDDSKNTAYLQMNSLKTED TAVYYCTSRGYSGYDYSSYFDYWGQGTLVTVSS |

-continued

| Description | SEQ | Sequence |
|---|---|---|
| D4D88936-5943 VL | 133 | DIQMTQSPSSLSASVGDRVTITCRASQGISNYLAWYQQKPGKVPKL LIYAASTLQSGVPSRFSGSGSGTDFTLTISSLQPEDVATYYCQKYN SAPLTFGGGTKVEIK |
| D4D88936-5943 VH | 134 | QVQLQESGPGLVKPSGTLSLTCAVSAGSISSSNWWSWVRQPPGKGL EWIGEISHSGSTNYNPSLKSRVTISVDKSKNQFSLKLSSVTAADTA VYYCARYNSGDDVDWFDPWGQGTLVSVSS |
| D4D88936-5944 VL | 135 | EIVMTQSPATLSLSPGERATLSCRASQSVNNNLAWYQQKPGQAPRL LIYGASTRATGIPARFSGSGSGTEFTLTISSLQSEDFAVYYCQQYN NWPLTFGGGTKVEIK |
| D4D88936-5944 VH | 136 | QVQLVQSGAEVKKPGASVKVSCKASGYTFTGYDMHWVRQAPGQGLE WMGWINPNSGGTNYAQKFQGRVTMTRDTSITTVYMELSRLRYDDTA VYYCARDGSLAARPHNWFDPWGQGTLVTVSS |
| D4D88936-6018 VL | 137 | DIQMTQSPSSLSASVGDRVTITCRASQSISSYLNWYQQKPGKAPKL LIYAASSLQSGVPSRFSGSGSGTDFTLTISSLQPEDFATYYCQQSY IIPFTFGPGTKLDIK |
| D4D88936-6018 VH | 138 | QVQLQESGPGLVKPSQTLSLTCAISGDSVSSNSAAWNWIRQSPSRG LEWLGRTYYRSKWYNDYAVSVKSRITINPDTSKNQFSLQLNSVTPE DTAVYYCARAPNWGSFDYWGQGTLVTVSS |
| D4D88936-6809 VL | 139 | DIQMTQSPSSLSASVGDRVTITCQASQDIRNYLNWYQQKPGKAPKV LIYDASNLETGVPSRFSGSGSGTDFTFTISSLQPEDIATYYCQQYD NLPITFGQGTRLEIK |
| D4D88936-6809 VH | 140 | EVQLVESGGGLVQPGGSLKLSCAASGFTFSGSAMHWVRQASGKGLE WVGRIRSKANNYATVYAASVKGRFTISRDDSKSTAYLQMNSLKTED TAVYYCASRGYSAYDYFDYWGQGTLVTVSS |
| D4D88936-7838 VL | 141 | DIQMTQSPSSLSASVGDRVTITCRASQSISSYLNWYQQKPGKAPKL LIYAASSLQSGVPSRFSGSGSGTDFTLTISSLQPEDFATYYCQQSY IIPFTFGPGTKLDIK |
| D4D88936-7838 VH | 142 | QVQLQESGPGLVKPSQTLSLTCAISGDSVSSNSAAWNWIRQSPSRG LEWLGRTYYRSKWYNDYAVSVKSRITINPDTSKNQFSLQLNSVTPE DTAVYYCARAPNWGSFDYWGQGTLVTVSS |
| D4D88936-8951 VL | 143 | DIQMTQSPSSLSASVGDRVTITCRASQDISNYLNWYQQKPGKAPKL LIYDASNLDKGVPSGFSGSGSGTDFTFTISSLQPEHIATYYCQQYD NLPITFGQGTRLEIK |
| D4D88936-8951 VH | 144 | EVQLVESGGGLVQPGGSLKLSCAASGFTFSGCAMHWVRQASGKGLE WVGRIRSKANNYATTYAASVKGRFTISRDDSKNTAYLQMNSLKTED TAVYYCTSRGYSGFDWFDYWGQGTLVSVSS |
| D4D88936-9137 VL | 145 | DIQMTQSPSSLSASVGDRVSITCRASQSISSYLNWYQQKPGKAPKL LIYAASSLQSGVPSRFSGSGSGTDFTLTISSLQPEDFATYYCQQSY STPLTFGGGTKVEIK |
| D4D88936-9137 VH | 146 | QVQLVQSGAEVKKPGASVKVSCKASGYTFTSYDINWVRQATGQGLE WMGWMNPNSGNTGYAQKFQGRVTMTRNTSISTAYMELSSLRSEDTA VYYCARRVWIAARPANWFDPWGQGTLVTVSS |
| hu24 VL | 147 | EIVLTQSPATLSLSPGERATLSCRASESVDSYGKSFMHWYQQKPGQ APRLLIYRASNLESGIPARFSGSGSGTDFTLTISSLEPEDFAVYYC QQSNEDPWTFGGGTKLEIK |
| hu24 VH | 148 | QVQLVQSGPEVKKPGASVKVSCKASGYTFTDYAVHWVRQAPGKRLE WIGVISTYNDYTYNNQDFKGRVTMTRDTSASTAYMELSRLRSEDTA VYYCARGNSYFYALDYWGQGTSVTVSS |

| | | | SLX-1040 Sequence |
|---|---|---|---|
| HCDR1 | Kabat | 149 | TYWMH |
| | Chothia | 150 | GYTFTTY |
| | IMGT | 151 | GYTFTTYW |
| | North/Aho | 152 | KASGYTFTTYWMH |
| | Contact | 153 | TTYWMH |
| | Grafted | 154 | GYTFTTYWMH |

-continued

| Description | | SEQ | Sequence |
|---|---|---|---|
| HCDR2 | Kabat Grafted | 155 | EIDPSDSYTTYNQKFTG |
| | Chothia | 156 | DPSDSY |
| | IMGT | 157 | IDPSDSYT |
| | North/Aho | 158 | EIDPSDSYTT |
| | Contact | 159 | WIGEIDPSDSYTT |
| HCDR3 | Kabat Chothia | 160 | PAWFGY |
| | IMGT North/Aho Grafted | 161 | LLPAWFGY |
| | Contact | 162 | LLPAWFG |
| LCDR1 | Kabat Chothia North/Aho Grafted | 163 | RASQEISGYLS |
| | IMGT | 164 | QEISGY |
| | Contact | 165 | SGYLSWL |
| LCDR2 | Kabat Chothia Grafted | 166 | AASTLDS |
| | IMGT | 167 | AAS |
| | North/Aho | 168 | YAASTLDS |
| | Contact | 169 | RLIYAASTLD |
| LCDR3 | Kabat Chothia IMGT North/Aho Grafted | 170 | LQYATYPFT |
| | Contact | 171 | LQYATYPF |

Humanized $V_H$ and $V_L$

| Description | SEQ | Sequence |
|---|---|---|
| GH (Z1-Z3) [None (CDR graft)] | 172 | QVQLVQSGAEVKKPGASVKVSCKAS**GYTFTTYWMH**WVRQAPGQGLE WMG**EIDPSDSYTTYNQKFTG**RVTMTRDTSTSTVYMELSSLRSEDTA VYYC**LLPAWFGY**WGQGTLVTVSS |
| GH + R71V (Z4) | 173 | QVQLVQSGAEVKKPGASVKVSCKAS**GYTFTTYWMH**WVRQAPGQGLE WMG**EIDPSDSYTTYNQKFTG**RVTMTVDTSTSTVYMELSSLRSEDTA VYYC**LLPAWFGY**WGQGTLVTVSS |
| GH + V78A | 174 | QVQLVQSGAEVKKPGASVKVSCKAS**GYTFTTYWMH**WVRQAPGQGLE WMG**EIDPSDSYTTYNQKFTG**RVTMTRDTSTSTAYMELSSLRSEDTA VYYC**LLPAWFGY**WGQGTLVTVSS |
| GH + Y91F | 175 | QVQLVQSGAEVKKPGASVKVSCKAS**GYTFTTYWMH**WVRQAPGQGLE WMG**EIDPSDSYTTYNQKFTG**RVTMTRDTSTSTVYMELSSLRSEDTA VYFC**LLPAWFGY**WGQGTLVTVSS |
| GH + Y91F + R71V | 176 | QVQLVQSGAEVKKPGASVKVSCKAS**GYTFTTYWM**HWVRQAPGQGLE WMG**EIDPSDSYTTYNQKFTG**RVTMTVDTSTSTVYMELSSLRSEDTA VYFC**LLPAWFGY**WGQGTLVTVSS |
| GH + Y91F + V78A | 177 | QVQLVQSGAEVKKPGASVKVSCKAS**GYTFTTYWMH**WVRQAPGQGLE WMG**EIDPSDSYTTYNQKFTG**RVTMTRDTSTSTAYMELSSLRSEDTA VYFC**LLPAWFGY**WGQGTLVTVSS |
| GH + Y91F + R71V + V78A | 178 | QVQLVQSGAEVKKPGASVKVSCKAS**GYTFTTYWMH**WVRQAPGQGLE WMG**EIDPSDSYTTYNQKFTG**RVTMTVDTSTSTAYMELSSLRSEDTA VYFC**LLPAWFGY**WGQGTLVTVSS |
| GH + Y91F + R71V + V78A + M48I | 179 | QVQLVQSGAEVKKPGASVKVSCKAS**GYTFTTYWMH**WVRQAPGQGLE WIG**EIDPSDSYTTYNQKFTG**RVTMTVDTSTSTAYMELSSLRSEDTA VYFC**LLPAWFGY**WGQGTLVTVSS |
| GH + Y91F + R71V + V78A + M69L | 180 | QVQLVQSGAEVKKPGASVKVSCKAS**GYTFTTYWMH**WVRQAPGQGLE WMG**EIDPSDSYTTYNQKFTG**RVTLTVDTSTSTAYMELSSLRSEDTA VYFC**LLPAWFGY**WGQGTLVTVSS |
| GH + Y91F + R71V + V78A + M48I + M69L | 181 | QVQLVQSGAEVKKPGASVKVSCKAS**GYTFTTYWMH**WVRQAPGQGLE WIG**EIDPSDSYTTYNQKFTG**RVTLTVDTSTSTAYMELSSLRSEDTA VYFC**LLPAWFGY**WGQGTLVTVSS |

-continued

| Description | SEQ | Sequence |
|---|---|---|
| GH + Y91F + R71V + V78A + M48I + M69L + V20L | 182 | QVQLVQSGAEVKKPGASVKLSCKAS**GYTFTTYWMH**WVRQAPGQGLE WIG**EIDPSDSYTTYNQKFTG**RVTLTVDTSTSTAYMELSSLRSEDTA VYFC**LLPAWFGY**WGQGTLVTVSS |
| GL | 183 | DIQMTQSPSSLSASVGDRVTITC**RASQEISGYLS**WYQQKPEKAPKS LIY**AASTLDS**GVPSRFSGSGSGTDFTLTISSLQPEDFATYYC**LQYA TYPFT**FGQGTKLEIK |
| GL + S46R | 184 | DIQMTQSPSSLSASVGDRVTITC**RASQEISGYLS**WYQQKPEKAPKR LIY**AASTLDS**GVPSRFSGSGSGTDFTLTISSLQPEDFATYYC**LQYA TYPFT**FGQGTKLEIK |
| GL + S46R + Y36L | 185 | DIQMTQSPSSLSASVGDRVTITC**RASQEISGYLS**WLQQKPEKAPKR LIY**AASTLDS**GVPSRFSGSGSGTDFTLTISSLQPEDFATYYC**LQYA TYPFT**FGQGTKLEIK |
| GL + S46R + Y36L + G66R | 186 | DIQMTQSPSSLSASVGDRVTITC**RASQEISGYLS**WLQQKPEKAPKR LIY**AASTLDS**GVPSRFSGSRSGTDFTLTISSLQPEDFATYYC**LQYA TYPFT**FGQGTKLEIK |
| GL + S46R + Y36L + F71Y | 187 | DIQMTQSPSSLSASVGDRVTITC**RASQEISGYLS**WLQQKPEKAPKR LIY**AASTLDS**GVPSRFSGSGSGTDYTLTISSLQPEDFATYYC**LQYA TYPFT**FGQGTKLEIK |
| GL + S46R + Y36L + G66R + F71Y | 188 | DIQMTQSPSSLSASVGDRVTITC**RASQEISGYLS**WLQQKPEKAPKR LIY**AASTLDS**GVPSRFSGSRSGTDYTLTISSLQPEDFATYYC**LQYA TYPFT**FGQGTKLEIK |
| GL + S46R + Y36L + G66R + F71Y + A43T | 189 | DIQMTQSPSSLSASVGDRVTITC**RASQEISGYLS**WLQQKPEKTPKR LIY**AASTLDS**GVPSRFSGSRSGTDYTLTISSLQPEDFATYYC**LQYA TYPFT**FGQGTKLEIK |
| GL + S46R + Y36L + G66R + F71Y + T69S | 190 | DIQMTQSPSSLSASVGDRVTITC**RASQEISGYLS**WLQQKPEKAPKR LIY**AASTLDS**GVPSRFSGSRSGSDYTLTISSLQPEDFATYYC**LQYA TYPFT**FGQGTKLEIK |
| GL + S46R + Y36L + G66R + F71Y + A43T + T69S | 191 | DIQMTQSPSSLSASVGDRVTITC**RASQEISGYLS**WLQQKPEKTPKR LIY**AASTLDS**GVPSRFSGSRSGSDYTLTISSLQPEDFATYYC**LQYA TYPFT**FGQGTKLEIK |
| GL + S46R + Y36L + G66R + F71Y + A43T + T69S + 121L | 192 | DIQMTQSPSSLSASVGDRVTLTC**RASQEISGYLS**WLQQKPEKTPKR LIY**AASTLDS**GVPSRFSGSRSGSDYTLTISSLQPEDFATYYC**LQYA TYPFT**FGQGTKLEIK |
| GH + R71V + V78A | 193 | QVQLVQSGAEVKKPGASVKVSCKAS**GYTFTTYWMH**WVRQAPGQGLE WMG**EIDPSDSYTTYNQKFTG**RVTMTVDTSTSTAYMELSSLRSEDTA VYYC**LLPAWFGY**WGQGTLVTVSS |
| GL + Y36L + G66R | 194 | DIQMTQSPSSLSASVGDRVTITC**RASQEISGYLS**WLQQKPEKAPKS LIY**AASTLDS**GVPSRFSGSRSGTDFTLTISSLQPEDFATYYC**LQYA TYPFT**FGQGTKLEIK |
| GL + Y36L + G66R + F71Y | 195 | DIQMTQSPSSLSASVGDRVTITC**RASQEISGYLS**WLQQKPEKAPKS LIY**AASTLDS**GVPSRFSGSRSGTDYTLTISSLQPEDFATYYC**LQYA TYPFT**FGQGTKLEIK |
| GH + R71V + V78A + M69L | 196 | QVQLVQSGAEVKKPGASVKVSCKAS**GYTFTTYWMH**WVRQAPGQGLE WMG**EIDPSDSYTTYNQKFTG**RVTLTVDTSTSTAYMELSSLRSEDTA VYYC**LLPAWFGY**WGQGTLVTVSS |
| GH + R71V + M69L | 197 | QVQLVQSGAEVKKPGASVKVSCKAS**GYTFTTYWMH**WVRQAPGQGLE WMG**EIDPSDSYTTYNQKFTG**RVTLTVDTSTSTVYMELSSLRSEDTA VYYC**LLPAWFGY**WGQGTLVTVSS |
| | | Other Sequences |
| Human PTK7 | 198 | MGAARGSPARPRRLPLLSVLLLPLLGGTQTAIVFIKQPSSQDALQG RRALLRCEVEAPGPVHVYWLLDGAPVQDTERRFAQGSSLSFAAVDR LQDSGTFQCVARDDVTGEEARSANASFNIKWIEAGPVVLKHPASEA EIQPQTQVTLRCHIDGHPRPTYQWFRDGTPLSDGQSNHTVSSKERN LTLRPAGPEHSGLYSCCAHSAFGQACSSQNFTLSIADESFARVVLA PQDVVVARYEEAMFHCQFSAQPPPSLQWLFEDETPITNRSRPPHLR RATVFANGSLLLTQVRPRNAGIYRCIGQGQRGPPIILEATLHLAEI EDMPLFEPRVFTAGSEERVTCLPPKGLPEPSVWWEHAGVRLPTHGR VYQKGHELVLANIAESDAGVYTCHAANLAGQRRQDVNITVATVPSW LKKPQDSQLEEGKPGYLDCLTQATPKPTVVWYRNQMLISEDSRFEV |

-continued

| Description | SEQ | Sequence |
|---|---|---|
| | | FKNGTLRINSVEVYDGTWYRCMSSTPAGSIEAQARVQVLEKLKFTP PPQPQQCMEFDKEATVPCSATGREKPTIKWERADGSSLPEWVTDNA GTLHFARVTRDDAGNYTCIASNGPQGQIRAHVQLTVAVFITFKVEP ERTTVYQGHTALLQCEAQGDPKPLIQWKGKDRILDPTKLGPRMHIF QNGSLVIHDVAPEDSGRYTCIAGNSCNIKHTEAPLYVVDKPVPEES EGPGSPPPYKMIQTIGLSVGAAVAYIIAVLGLMFYCKKRCKAKRLQ KQPEGEEPEMECLNGGPLQNGQPSAEIQEEVALTSLGSGPAATNKR HSTSDKMHFPRSSLQPITTLGKSEFGEVELAKAQGLEEGVAETLVL VKSLQSKDEQQQLDFRRELEMFGKLNHANVVRLLGLCREAEPHYMV LEYVDLGDLKQFLRISKSKDEKLKSQPLSTKQKVALCTQVALGMEH LSNNRFVHKDLAARNCLVSAQRQVKVSALGLSKDVYNSEYYHFRQA WVPLRWMSPEAILEGDFSTKSDVWAFGVLMWEVFTHGEMPHGGQAD DEVLADLQAGKARLPQPEGCPSKLYRLMQRCWALSPKDRPSFSEIA SALGDSTVDSKP |
| Human Light Chain Constant Region | 199 | RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC |
| Human Heavy Chain Constant Region | 200 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| Human Effectorless Heavy Chain Constant Region | 201 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALAAPIEKTISKAKGQPREPQ VYTLPPSRDELTKNQVSLTCLVKGFYPSDIAVEWESNGQPENNYKT TPPVLDSDGSFFLYSKLTVDKSRWQQGNVESCSVMHEALHNHYTQK SLSLSPGK |

D4D88750-935 Sequence

| | | | |
|---|---|---|---|
| HCDR1 | Kabat | 202 | RFTMN |
| | Chothia | 203 | GFTFSRF |
| | IMGT | 204 | GFTFSRFT |
| | North/Aho | 205 | VVSGFTFSRFTMN |
| | Contact | 206 | SRFTMN |
| HCDR2 | Kabat | 207 | SISSTSSYVYYGDSVKG |
| | Chothia | 208 | SSTSSY |
| | IMGT | 209 | ISSTSSYV |
| | North/Aho | 210 | SISSTSSYVY |
| | Contact | 211 | WVSSISSTSSYVY |
| HCDR3 | Kabat<br>Chothia | 212 | EGGDWNYDYNYYYMDV |
| | IMGT<br>North/Aho | 213 | AREGGDWNYDYNYYYMDV |
| | Contact | 214 | AREGGDWNYDYNYYYMD |
| LCDR1 | Kabat<br>Chothia<br>North/Aho | 215 | KSSQNVLYNSNNKNYLA |
| | IMGT | 216 | QNVLYNSNNKNY |
| | Contact | 217 | KNYLAWY |
| LCDR2 | Kabat<br>Chothia | 218 | WASTRES |
| | IMGT | 219 | WAS |
| | North/Aho | 220 | YWASTRES |
| | Contact | 221 | LLIYWASTRE |
| LCDR3 | Kabat<br>Chothia<br>IMGT<br>North/Aho<br>Grafted | 222 | QQYYSTPYT |
| | Contact | 223 | QQYYSTPY |

-continued

| Description | | SEQ | Sequence |
|---|---|---|---|
| | | | D4D88936-3188 Sequence |
| HCDR1 | Kabat | 224 | SYDMH |
| | Chothia | 225 | GFTFSSY |
| | IMGT | 226 | GFTFSSYD |
| | North/Aho | 227 | AASGFTFSSYDMH |
| | Contact | 228 | SSYDMH |
| HCDR2 | Kabat | 229 | GINTDGDTFYPGSVKG |
| | Chothia | 230 | NTDGD |
| | IMGT | 231 | INTDGDT |
| | North/Aho | 232 | GINTDGDTF |
| | Contact | 233 | WVSGINTDGDTF |
| HCDR3 | Kabat | 234 | RGWNYGFDY |
| | Chothia | | |
| | IMGT | 235 | ARRGWNYGFDY |
| | North/Aho | | |
| | Contact | 236 | ARRGWNYGFD |
| LCDR1 | Kabat | 237 | QASQDIRNYLN |
| | Chothia | | |
| | North/Aho | | |
| | IMGT | 238 | QDIRNY |
| | Contact | 239 | RNYLNWY |
| LCDR2 | Kabat | 240 | DASNLET |
| | Chothia | | |
| | IMGT | 241 | DAS |
| | North/Aho | 242 | YDASNLET |
| | Contact | 243 | LLIYDASNLE |
| LCDR3 | Kabat | 244 | QPYDNLMYT |
| | Chothia | | |
| | IMGT | | |
| | North/Aho | | |
| | Contact | 245 | QPYDNLMY |

SEQUENCE LISTING

```
Sequence total quantity: 245
SEQ ID NO: 1            moltype = AA  length = 108
FEATURE                 Location/Qualifiers
REGION                  1..108
                        note = Synthetic
source                  1..108
                        mol_type = protein
                        organism = synthetic construct
SEQUENCE: 1
EIVLTQSPAT LSLSPGERAA LSCRASQSVS SSYLAWYQQK PGQAPRLLIY GASRRATGIP  60
DRFSGSGSGT DFTLTISRLE PEDFAVYYCQ QYGSSPRTFG QGTKVEIR              108

SEQ ID NO: 2            moltype = AA  length = 119
FEATURE                 Location/Qualifiers
REGION                  1..119
                        note = Synthetic
source                  1..119
                        mol_type = protein
                        organism = synthetic construct
SEQUENCE: 2
QVQLQESGPG LVKPSGTLSL TCAVSGGSIS STNWWSWVRQ PPGKGLEWIG EIYHSGSTNY  60
NPSLKSRVTI SVDKSKNQFS LKLSSVTAAD TAVYYCARED SNYDWFDPWG QGTLVTVSS   119

SEQ ID NO: 3            moltype = AA  length = 107
FEATURE                 Location/Qualifiers
REGION                  1..107
                        note = Synthetic
source                  1..107
                        mol_type = protein
                        organism = synthetic construct
SEQUENCE: 3
DIQMTQSPSS LSASVGDRVT ITCQASQDIS NYLNWYQQKP GKAPKLLIYD ASNLETGVPS  60
```

```
RFSGSGSGTD FTFTISSLQP EDIATYYCQQ YDNLPFTFGP GTKVDIK              107

SEQ ID NO: 4            moltype = AA  length = 121
FEATURE                 Location/Qualifiers
REGION                  1..121
                        note = Synthetic
source                  1..121
                        mol_type = protein
                        organism = synthetic construct
SEQUENCE: 4
QVQLQESGPG LVKPSETLSL TCTVSGGSVS SGSYYWSWIR QPPGKGLEWI GYIYYSGSTN  60
YNPSLKSRVT ISVDTSKNQF SLKLSSVTAA DTAVYYCARD RSIAVAGFDY WGQGTLVTVS  120
S                                                                 121

SEQ ID NO: 5            moltype = AA  length = 107
FEATURE                 Location/Qualifiers
REGION                  1..107
                        note = Synthetic
source                  1..107
                        mol_type = protein
                        organism = synthetic construct
SEQUENCE: 5
EIVLTQSPAT LSLSPGERAT LSCRASQSVS NYLAWYQQKP GQAPRLLIYD AYNRATGIPA  60
RFSGSGSGTD FTLTISSLEP EDFVVYYCQE RSNWPLTFGG GTKVEIK              107

SEQ ID NO: 6            moltype = AA  length = 124
FEATURE                 Location/Qualifiers
REGION                  1..124
                        note = Synthetic
source                  1..124
                        mol_type = protein
                        organism = synthetic construct
SEQUENCE: 6
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TGVYYCAREF RGYSGYDPDA FDVWGHGTMV  120
TVSS                                                              124

SEQ ID NO: 7            moltype = AA  length = 107
FEATURE                 Location/Qualifiers
REGION                  1..107
                        note = Synthetic
source                  1..107
                        mol_type = protein
                        organism = synthetic construct
SEQUENCE: 7
DIQMTQSPSS LSASVGDRVT ITCRASQTIS SYLNWYQQKP EKAPKLLIYA ASSLQRGVPS  60
RFRGSGSGTD FTLTVSSLQP EDFATYYCQQ SYSIPYTFGQ GTKLEIK              107

SEQ ID NO: 8            moltype = AA  length = 117
FEATURE                 Location/Qualifiers
REGION                  1..117
                        note = Synthetic
source                  1..117
                        mol_type = protein
                        organism = synthetic construct
SEQUENCE: 8
QVQLQESGPG LVKPSGTLSL TCAVSGGSIS SDHWWSWVRQ PPGKGLEWIG EIFHSGNTNY  60
NPSLKSRVTI SVDKSKNQFS LKLSSVAAAD TAVYYCASGY NWNLGYWGQG TLVTVSS     117

SEQ ID NO: 9            moltype = AA  length = 112
FEATURE                 Location/Qualifiers
REGION                  1..112
                        note = Synthetic
source                  1..112
                        mol_type = protein
                        organism = synthetic construct
SEQUENCE: 9
DVVMTQTPLS LPVTLGQPAS ISCRSSQSLI YSDGNTYLNW FQQRPGQSPR RLIYKVSDRD  60
SGVPDRFSGS GSGTDFTLKI SRVEAEDVGI YYCMLGTHWP YTFGQGTKLE IK         112

SEQ ID NO: 10           moltype = AA  length = 121
FEATURE                 Location/Qualifiers
REGION                  1..121
                        note = Synthetic
source                  1..121
                        mol_type = protein
                        organism = synthetic construct
SEQUENCE: 10
EVQLVESGGG LVQPGGSLRL SCAASGFTFS SFAMSWVRQA PGKGLEWVSG ISGGVGLTYY  60
```

```
ADSVKGRFTI SRDNSKDTLY LQMNSLRAED TAVFYCAKDQ GYSSSSPFDY WGQGTLVTVS  120
S                                                                  121

SEQ ID NO: 11          moltype = AA  length = 113
FEATURE                Location/Qualifiers
REGION                 1..113
                       note = Synthetic
source                 1..113
                       mol_type = protein
                       organism = synthetic construct
SEQUENCE: 11
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PYTFGQGTKL EIK         113

SEQ ID NO: 12          moltype = AA  length = 117
FEATURE                Location/Qualifiers
REGION                 1..117
                       note = Synthetic
source                 1..117
                       mol_type = protein
                       organism = synthetic construct
SEQUENCE: 12
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCAREG WGPFDYWGQG TLVTVSS     117

SEQ ID NO: 13          moltype = AA  length = 108
FEATURE                Location/Qualifiers
REGION                 1..108
                       note = Synthetic
source                 1..108
                       mol_type = protein
                       organism = synthetic construct
SEQUENCE: 13
EIVLTQSPAT LSLSPGERAT LSCRASQSVS SSYLAWYQQK PGQAPRLLIY GASSRATGIP  60
DRFSGSGSGT DFTLTISRLE PEDFAVYYCQ QYGSSPRTFG QGTKVEIK               108

SEQ ID NO: 14          moltype = AA  length = 125
FEATURE                Location/Qualifiers
REGION                 1..125
                       note = Synthetic
source                 1..125
                       mol_type = protein
                       organism = synthetic construct
SEQUENCE: 14
EVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKDL RYSGSYYLYD AFDIWGQGTM  120
VTVSS                                                              125

SEQ ID NO: 15          moltype = AA  length = 107
FEATURE                Location/Qualifiers
REGION                 1..107
                       note = Synthetic
source                 1..107
                       mol_type = protein
                       organism = synthetic construct
SEQUENCE: 15
EIVMTQSPAT LSVSPGERAT LSCRASQSIS SNLAWYQQKP GQAPRLLIFG ASTRATGIPA  60
RFSGSGSGTD FTLTISSLQS EDFAVYYCQQ YNNWPYTFGQ GTNLEIK                107

SEQ ID NO: 16          moltype = AA  length = 121
FEATURE                Location/Qualifiers
REGION                 1..121
                       note = Synthetic
source                 1..121
                       mol_type = protein
                       organism = synthetic construct
SEQUENCE: 16
QVQLVQSGAE VKKPGASVKV SCKASGYTFT SYDIIWVRQA TGQGLEWMGW MNPNSGNTGY  60
EQKFQGRVTM TRNTSISTAY MELSSLRSED TAVHYCARGY TNARAEYFQH WGQGTLVTVS  120
S                                                                  121

SEQ ID NO: 17          moltype = AA  length = 107
FEATURE                Location/Qualifiers
REGION                 1..107
                       note = Synthetic
source                 1..107
                       mol_type = protein
                       organism = synthetic construct
SEQUENCE: 17
```

-continued

```
EIVMTQSPAT LSLSPGERAT LSCRASQSIS NNLAWYQQKP GQAPRLLIYG ASTRATGIPA  60
RFSDSGSGTE FTLTISSLQS EDFAVYFCQQ YHNWPYTFGQ GTKLEIK                107

SEQ ID NO: 18          moltype = AA  length = 121
FEATURE                Location/Qualifiers
REGION                 1..121
                       note = Synthetic
source                 1..121
                       mol_type = protein
                       organism = synthetic construct
SEQUENCE: 18
QVQLQQSGAE VKKPGASVKV SCKASGYIFT SYDINWVRQA TGQGLEWMGW MNPNSGNTGY  60
AQKFQGRVTM TMDPSISTAY MELSSLRSED TAVYFCARGY NNARAEYFQH WGQGTLVTVS  120
S                                                                  121

SEQ ID NO: 19          moltype = AA  length = 107
FEATURE                Location/Qualifiers
REGION                 1..107
                       note = Synthetic
source                 1..107
                       mol_type = protein
                       organism = synthetic construct
SEQUENCE: 19
DIQMTQSPSS LSASVGDRVS ITCRASQSIS SWLAWYQQKP GKAPKLLIYK ASSLESGVPS  60
RFSGSGSGTE FTLTISTLQP DDFATYYCQQ YNSYSRTFGQ GTKVEIK                107

SEQ ID NO: 20          moltype = AA  length = 123
FEATURE                Location/Qualifiers
REGION                 1..123
                       note = Synthetic
source                 1..123
                       mol_type = protein
                       organism = synthetic construct
SEQUENCE: 20
EVQLVESGGG VVRPGGSLRL SCAASGFTFD DYGMSWVRQA PGKGLEWVSG INWNGGSTGY  60
VEYVKGRFTI SRDNAKNSLY LQMKSVRAED TALYYCARDR LGYSYGWGYF DYWGQGTLVT  120
VSS                                                                123

SEQ ID NO: 21          moltype = AA  length = 107
FEATURE                Location/Qualifiers
REGION                 1..107
                       note = Synthetic
source                 1..107
                       mol_type = protein
                       organism = synthetic construct
SEQUENCE: 21
DIQMTQSPSS LSASVGDRVT ITCRASQSIS SYLNWYQKKS GKAPKLLIYA ASSLQSGVPS  60
RFSGSGSGTD FTLTISSLQP EDFATYYCQQ SYSNPWTFGQ GTKVEIK                107

SEQ ID NO: 22          moltype = AA  length = 121
FEATURE                Location/Qualifiers
REGION                 1..121
                       note = Synthetic
source                 1..121
                       mol_type = protein
                       organism = synthetic construct
SEQUENCE: 22
EVQLVESGGG LVQPGGSLRL SCAASGFTFS SYSMNWVRQA PGKGLEWVSY ISSSSTTIYY  60
ADSVKGRFTI SRDNAKNSLY LQMSSLRDED TAVYYCARVD SRNWNYFFDY WGQGTLVTVS  120
S                                                                  121

SEQ ID NO: 23          moltype = AA  length = 108
FEATURE                Location/Qualifiers
REGION                 1..108
                       note = Synthetic
source                 1..108
                       mol_type = protein
                       organism = synthetic construct
SEQUENCE: 23
EIVLTQSPAT LSLSPGERAA LSCRASQSVS SSYLAWYQQK PGQAPRLLIY GASRRATGIP  60
DRFSGSGSGT DFTLTISRLE PEDFAVYYCQ QYGSSPRTFG QGTKVEIK               108

SEQ ID NO: 24          moltype = AA  length = 119
FEATURE                Location/Qualifiers
REGION                 1..119
                       note = Synthetic
source                 1..119
                       mol_type = protein
                       organism = synthetic construct
```

-continued

```
SEQUENCE: 24
QVQLQESGPG LVKPSGTLSL TCAVSGGSIS STNWWSWVRQ PPGKGLEWIG EIYHSGSTNY  60
NPSLKSRVTI SVDKSKNQFS LKLSSVTAAD TAVYYCARED SNYDWFDPWG QGTLVTVSS   119

SEQ ID NO: 25          moltype = AA  length = 107
FEATURE                Location/Qualifiers
REGION                 1..107
                       note = Synthetic
source                 1..107
                       mol_type = protein
                       organism = synthetic construct
SEQUENCE: 25
DIQMTQSPSS LSASVGDRVT ITCRASQTIS SWLAWYQQKP GKAPKLLIYK ASTLEGGVPS  60
RFSGSGSGTE FTLTISSLQP DDFATYYCQQ YNIYSRTFGQ GTKVEIK               107

SEQ ID NO: 26          moltype = AA  length = 123
FEATURE                Location/Qualifiers
REGION                 1..123
                       note = Synthetic
source                 1..123
                       mol_type = protein
                       organism = synthetic construct
SEQUENCE: 26
EVQLVESGGG VVRPGGSLRL SCAASGFTFD DYGMSWVRQA PGKGLEWVSG INWNGGSTGY  60
VDSVKGRFTF SRDNAKNSLY LQMNSLRAED TALYYCARDR LGYSYGWGYF DYWGQGTLVT  120
VSS                                                               123

SEQ ID NO: 27          moltype = AA  length = 107
FEATURE                Location/Qualifiers
REGION                 1..107
                       note = Synthetic
source                 1..107
                       mol_type = protein
                       organism = synthetic construct
SEQUENCE: 27
DIQMTQSPSS LSASVGDRVT ITCRASQDIS NYLAWYQQKP GKVPNLLIYA ASTLQSGVPS  60
RFSGSGSGTD FTLTISSLQP EDVATYYCQK YNSAPLTFGG GTKVEIK               107

SEQ ID NO: 28          moltype = AA  length = 120
FEATURE                Location/Qualifiers
REGION                 1..120
                       note = Synthetic
source                 1..120
                       mol_type = protein
                       organism = synthetic construct
SEQUENCE: 28
EVQLVESGGG LVKPGGSLRL SCAASGFTFS NAWMNWVRQA PGKGLEWVGR IKSKTDAGTT  60
DYAAPVKGRF TISRDDSKNT LYLQMNSLKT EDTAVYYCPT GWNYHAFDIW GQGTMVTVSS  120

SEQ ID NO: 29          moltype = AA  length = 107
FEATURE                Location/Qualifiers
REGION                 1..107
                       note = Synthetic
source                 1..107
                       mol_type = protein
                       organism = synthetic construct
SEQUENCE: 29
DIQMTQSPSS LSASVGDRVT ITCRASQSIS SWLAWYQQKP GKAPKLLIYK ASSLESGVPS  60
RFSGSGSGTE FTLTISSLQP DDFETYYCQQ YNSYSRTFGQ GTKVEIK               107

SEQ ID NO: 30          moltype = AA  length = 123
FEATURE                Location/Qualifiers
REGION                 1..123
                       note = Synthetic
source                 1..123
                       mol_type = protein
                       organism = synthetic construct
SEQUENCE: 30
EVQLVESGGG VVRPGGSLRL SCAASGFTFD DYGMSWVRQA PGKGLEWVSG INWNGGSTGY  60
VDSVKGRFIF SRDNAKNSLY LQMNSLRAED TALYYCARDR LGYSYGWGYF DYWGQGTLVT  120
VSS                                                               123

SEQ ID NO: 31          moltype = AA  length = 107
FEATURE                Location/Qualifiers
REGION                 1..107
                       note = Synthetic
source                 1..107
                       mol_type = protein
                       organism = synthetic construct
```

-continued

```
SEQUENCE: 31
DIQMTQSPSS LSASVGDRVT ITCRASQSIS SWLAWYQQKP GKAPKLLIYK ASSLESGVPS  60
RFSGSGSGTE FTLTISSLQP DDFATYYCQQ YNSYSRTFGQ GTKVEIK               107

SEQ ID NO: 32          moltype = AA  length = 123
FEATURE                Location/Qualifiers
REGION                 1..123
                       note = Synthetic
source                 1..123
                       mol_type = protein
                       organism = synthetic construct
SEQUENCE: 32
EVQLVESGGG VVRPGGSLRL SCEASGFTFD DYGMSWVRQA PGKGLEWVSG INWNGGSTGY  60
VEYVKGRFTI SRDNAKNSLY LQMKSVRAED TALYYCARDR LGYSYGWGYF DYWGQGTLVT  120
VSS                                                               123

SEQ ID NO: 33          moltype = AA  length = 107
FEATURE                Location/Qualifiers
REGION                 1..107
                       note = Synthetic
source                 1..107
                       mol_type = protein
                       organism = synthetic construct
SEQUENCE: 33
DIQMTQSPSS LSASVGDRVS ITCRASQSIS SWLAWYQQKP GKAPKLLIYK ASSLESGVPS  60
RFSGSGSGTE FTLTISTLQP DDFATYYCQQ YNSYSRTFGQ GTKVEIK               107

SEQ ID NO: 34          moltype = AA  length = 123
FEATURE                Location/Qualifiers
REGION                 1..123
                       note = Synthetic
source                 1..123
                       mol_type = protein
                       organism = synthetic construct
SEQUENCE: 34
EVQLVESGGG VVRPGGSLRL SCAASGFTFD DYGMSWVRQA PGKGLEWVSG INWNGGSTGY  60
VEYVKGRFTI SRDNAKNSLY LQMKSVRAED TALYYCARDR LGYSYGWGYF DYWGQGTLVT  120
VSS                                                               123

SEQ ID NO: 35          moltype = AA  length = 107
FEATURE                Location/Qualifiers
REGION                 1..107
                       note = Synthetic
source                 1..107
                       mol_type = protein
                       organism = synthetic construct
SEQUENCE: 35
EIVMTQSPAT LSVSPGERAT LSCRASQSVS SNLAWYQQKP GQAPRLLIYG ASTRATGIPA  60
RFSGSGSGTE FTLTFSSLQS EDFAVYSCQH YNDWPYTFGQ GTNLEIK               107

SEQ ID NO: 36          moltype = AA  length = 121
FEATURE                Location/Qualifiers
REGION                 1..121
                       note = Synthetic
source                 1..121
                       mol_type = protein
                       organism = synthetic construct
SEQUENCE: 36
QVQLVQSGAE VKKPGASVKV SCKASGYTFI SYDINWVRQA TGQGLEWMGW MNPNSGNTGY  60
AQKFQGRVTM TRKTSISTAY MELSSLRSED TAVYYCARGY TYARAEYFHP WGQGTLVTVS  120
S                                                                 121

SEQ ID NO: 37          moltype = AA  length = 107
FEATURE                Location/Qualifiers
REGION                 1..107
                       note = Synthetic
source                 1..107
                       mol_type = protein
                       organism = synthetic construct
SEQUENCE: 37
DIQMTQSPSS LSASVGDRVT ITCRASQSIA IYLNWYQQRP GKPPKLLIFT ASSLQSGVPS  60
RFTGSGSGTD FTLSISSLQP EDFATYYCQQ SYSTPPTFGQ GTKVEIK               107

SEQ ID NO: 38          moltype = AA  length = 121
FEATURE                Location/Qualifiers
REGION                 1..121
                       note = Synthetic
source                 1..121
                       mol_type = protein
```

```
                        organism = synthetic construct
SEQUENCE: 38
QVQLVQSGAE VKKPGASVKV SCRASGYTFT DYFIHWVRQA PGQGLEWMGW ISPNSGGTNY  60
AQKFQGRVTM TRDTSITTAY MELSSLTSDD TAVYYCARYD YDGYSGWFDP WGQGTLVTVS  120
S                                                                 121

SEQ ID NO: 39           moltype = AA  length = 107
FEATURE                 Location/Qualifiers
REGION                  1..107
                        note = Synthetic
source                  1..107
                        mol_type = protein
                        organism = synthetic construct
SEQUENCE: 39
DIQMTQSPSS LSASVGDRVT ITCRASQGIS NYLAWYQQKP GKVPKLLIYA ASTLQSGVPS  60
RFSGSGSGTD FTLTISSLQP EDVATYYCQK YNSAPRTFGQ GTKVEIK               107

SEQ ID NO: 40           moltype = AA  length = 119
FEATURE                 Location/Qualifiers
REGION                  1..119
                        note = Synthetic
source                  1..119
                        mol_type = protein
                        organism = synthetic construct
SEQUENCE: 40
QVQLVQSGAE VKKPGASVKV SCKASGYTFT GYYMHWVRQA PGQGLEWMGW INPNSGGTNY  60
AQKFQGRVTM TRDTSISTVY MEVSRLRSDD AAVYYCAREG QMTHASDIWG QGTMVTVSS   119

SEQ ID NO: 41           moltype = AA  length = 106
FEATURE                 Location/Qualifiers
REGION                  1..106
                        note = Synthetic
source                  1..106
                        mol_type = protein
                        organism = synthetic construct
SEQUENCE: 41
DIQMTQSPSS LSASVGDRVT ITCQASQDIS NYLHWYQQKP GKAPELLIYD ASNLETGVPS  60
RFSGSGSGTD FTFTIGSLQA EDIATYYCQQ YDHLPTFGGG TKVEIK                106

SEQ ID NO: 42           moltype = AA  length = 121
FEATURE                 Location/Qualifiers
REGION                  1..121
                        note = Synthetic
source                  1..121
                        mol_type = protein
                        organism = synthetic construct
SEQUENCE: 42
EVQLVESGGG VVRPGGSLRL SCAASGFTFD DYDMSWVRQA PGKGLEWVSG INWNGGSTGY  60
ADSVKGRCTI SRDNAKNSLY LQMNSLRAED TALYHCAREK YSSSSWAFDI WGQGTMVTVS  120
S                                                                 121

SEQ ID NO: 43           moltype = AA  length = 107
FEATURE                 Location/Qualifiers
REGION                  1..107
                        note = Synthetic
source                  1..107
                        mol_type = protein
                        organism = synthetic construct
SEQUENCE: 43
DIQMTQSPSS LSASVGDRVI ITCQASQDIT NYLNWYQQRP GKAPKLLIYD ASNLETGVPS  60
RFSGSGSGTD FTFIISSLQP EDIATYYCQQ YDNLPITFGQ GTRLEIK               107

SEQ ID NO: 44           moltype = AA  length = 123
FEATURE                 Location/Qualifiers
REGION                  1..123
                        note = Synthetic
source                  1..123
                        mol_type = protein
                        organism = synthetic construct
SEQUENCE: 44
EVQLVESGGG LVQPGGSLKL SCAASGFTFS GFAMHWVRQA SGKGLEWIGR IRSKANNYAT  60
AYAASAKGRF TISRDDSKNT AYLQMNSLKT EDTAVYYCTS SGYSYGYLFF DYWGQGTLVT  120
VSS                                                               123

SEQ ID NO: 45           moltype = AA  length = 111
FEATURE                 Location/Qualifiers
REGION                  1..111
                        note = Synthetic
source                  1..111
```

```
                         mol_type = protein
                         organism = synthetic construct
SEQUENCE: 45
DIVLTQSPAS LAVSLGQRAT ISCRASESVD NYGISFMNWF QQKPGQPPKL LIYAASIQGS  60
GVPARFSGSG SGTDFSLNIH PMEEDDTAMY FCQQSKEVPR TFGGGTKLEI K           111

SEQ ID NO: 46            moltype = AA  length = 114
FEATURE                  Location/Qualifiers
REGION                   1..114
                         note = Synthetic
source                   1..114
                         mol_type = protein
                         organism = synthetic construct
SEQUENCE: 46
QVQLQQSGAE LAKPGASVKL SCRASGYTFI RYWMHWVKQR PGQGLEWIGY INPSTDYTEY  60
NQKFKDKATL TADKSSSTAY MQLSSLTYED SAVYYCARSY LDYWGQGTTL TVSS        114

SEQ ID NO: 47            moltype = AA  length = 109
FEATURE                  Location/Qualifiers
REGION                   1..109
                         note = Synthetic
source                   1..109
                         mol_type = protein
                         organism = synthetic construct
SEQUENCE: 47
QAVVTQESAL TTSPGETVTL TCRSSTGAVT TSNYANWVQE KPDHLFTGLI GGTNNRAPGV  60
PARFSGSLIG DKAALTITGA QTEDEAIYFC ALWYSNHWVF GGGTKLTVL              109

SEQ ID NO: 48            moltype = AA  length = 120
FEATURE                  Location/Qualifiers
REGION                   1..120
                         note = Synthetic
source                   1..120
                         mol_type = protein
                         organism = synthetic construct
SEQUENCE: 48
QVQLQQPGAE LVRPGSSVKL SCKASGYTFT SYWMHWVKQR PIQGLEWIGN IDPSDSETHY  60
NQKFKDKATL TVDKSSSTAY MQLSSLTSED SAVYYCASYD GYTDWYFDVW GTGTTVTVSS  120

SEQ ID NO: 49            moltype = AA  length = 109
FEATURE                  Location/Qualifiers
REGION                   1..109
                         note = Synthetic
source                   1..109
                         mol_type = protein
                         organism = synthetic construct
SEQUENCE: 49
QAVVTQESAL TTSPGETVTL TCRSSTGAVT TSNYANWVQE KPDHLFTGLI GGTNNRAPGV  60
PARFSGSLIG DKAALTITGA QTEDEAIYFC ALWYSNHWVF GGGTKLTVL              109

SEQ ID NO: 50            moltype = AA  length = 121
FEATURE                  Location/Qualifiers
REGION                   1..121
                         note = Synthetic
source                   1..121
                         mol_type = protein
                         organism = synthetic construct
SEQUENCE: 50
QVQLQQPGAE LVKPGASVKL SCRASGYSFT SYWMLWVKQR PGQGLEWIGM IHPNSGSTNF  60
NEQFRSKATL TVDKSSSTAY IQLSSLTSED SAVYYCARLD YYGSIEHFDY WGQGTTLTVS  120
S                                                                  121

SEQ ID NO: 51            moltype = AA  length = 107
FEATURE                  Location/Qualifiers
REGION                   1..107
                         note = Synthetic
source                   1..107
                         mol_type = protein
                         organism = synthetic construct
SEQUENCE: 51
DIQMTQSSSY LSVSLGGRVT ITCKASDHIN NWLVWYQQKP GNAPRLLISG ATSLETGVPS  60
RFSGSGSGKD YTLSITSLQT EDVATYYCQQ YWSTPYTFGG GTKLEIK                107

SEQ ID NO: 52            moltype = AA  length = 120
FEATURE                  Location/Qualifiers
REGION                   1..120
                         note = Synthetic
source                   1..120
                         mol_type = protein
```

```
                        organism = synthetic construct
SEQUENCE: 52
QVQLQQPGAE LVRPGSSVKL SCKASGYTFT SYWMHWVKQR PIQGLEWIGN IDPSDNKSHY  60
NKKFKDKATL TVDKSSSTAY MQLSSLTSED SAVYYCARGG LTGTPRFGYW GQGTLVTVSA  120

SEQ ID NO: 53           moltype = AA  length = 107
FEATURE                 Location/Qualifiers
REGION                  1..107
                        note = Synthetic
source                  1..107
                        mol_type = protein
                        organism = synthetic construct
SEQUENCE: 53
DIQMTQTPSS LSASLGDRVT ISCRASQDIR NYLNWYQQKP DGTVKLLIYY TSRLHSGVPS  60
RFSGSGSGTD YSLTISNLEQ EDIATYFCQQ GNTLPPTFGG GTKLEIK              107

SEQ ID NO: 54           moltype = AA  length = 120
FEATURE                 Location/Qualifiers
REGION                  1..120
                        note = Synthetic
source                  1..120
                        mol_type = protein
                        organism = synthetic construct
SEQUENCE: 54
QVQLQESGPG LVKPSQSLSL TCSVTGYSIT SGYYWNWIRQ FPGNRLEWMG YISYDGNNNY  60
NPSLKNRISI TRDTSKNQFF LKLNSVTTED TATYYCAKDF YRRWGAMDYW GQGTSVTVSS  120

SEQ ID NO: 55           moltype = AA  length = 111
FEATURE                 Location/Qualifiers
REGION                  1..111
                        note = Synthetic
source                  1..111
                        mol_type = protein
                        organism = synthetic construct
SEQUENCE: 55
DIVLTQSPAS LAVSLGQRAT ISCRASQSVS TSSYSYMHWY QQKPGQPPKL LIKYASNLES  60
GVPARFSGSG SGTDFTLNIH PVEEVDTAAY YCQHSWEIPY TFGGGTKLEI K          111

SEQ ID NO: 56           moltype = AA  length = 121
FEATURE                 Location/Qualifiers
REGION                  1..121
                        note = Synthetic
source                  1..121
                        mol_type = protein
                        organism = synthetic construct
SEQUENCE: 56
QVQLQQSGAG LARPGTSVKL SCKASGYTFT SFGISWVKQR PGQGLEWIGE IYPRRGNTLY  60
NEQFKGKATL TADKSSSTAH MELRSLTSED SAVYFCAREG AYSNHYAFDY WGQGTSVTVS  120
S                                                                 121

SEQ ID NO: 57           moltype = AA  length = 107
FEATURE                 Location/Qualifiers
REGION                  1..107
                        note = Synthetic
source                  1..107
                        mol_type = protein
                        organism = synthetic construct
SEQUENCE: 57
DIVLTQSPSS LSASLGERVS LTCRASQEIS GYLSWLQQKP DGTIKRLIYA ASTLDSGVPK  60
RFSGSRSGSD YSLTISSLES EDFADYYCLQ YASYPYTFGG GTKLEIK              107

SEQ ID NO: 58           moltype = AA  length = 119
FEATURE                 Location/Qualifiers
REGION                  1..119
                        note = Synthetic
source                  1..119
                        mol_type = protein
                        organism = synthetic construct
SEQUENCE: 58
QVQLQQSGAE LVRPGASVKL SCTASGFNIK DDYMHWVKQR PEQGLEWIGW IDPENGDTEY  60
ASKFQGKATI TADTSSNTAY LQLSSLTSED TAVYYCTTDY GNNWYFDVWG TGTTVTVSS   119

SEQ ID NO: 59           moltype = AA  length = 107
FEATURE                 Location/Qualifiers
REGION                  1..107
                        note = Synthetic
source                  1..107
                        mol_type = protein
                        organism = synthetic construct
```

```
SEQUENCE: 59
DIQMTQSPSS LSASLGDTIT ITCHASQNIN VWLSWYQQKP GNIPKLLIYK ASNLHTGVPS  60
RFSGSGSGTG FTLTISSLQP EDIATYYCQQ GQSYPFTFGS GTKLEIK               107

SEQ ID NO: 60          moltype = AA  length = 114
FEATURE                Location/Qualifiers
REGION                 1..114
                       note = Synthetic
source                 1..114
                       mol_type = protein
                       organism = synthetic construct
SEQUENCE: 60
QVQLQQSGAE LAKPGASVKL SCKASGYTFT SYWMHWVKQR PGQGLEWIGY INPSSGYTKY  60
NQKFKDKATL TADKSSSTAY MQLSSLTYED SAVYYCARSY FDYWGQGTTL TVSS        114

SEQ ID NO: 61          moltype = AA  length = 111
FEATURE                Location/Qualifiers
REGION                 1..111
                       note = Synthetic
source                 1..111
                       mol_type = protein
                       organism = synthetic construct
SEQUENCE: 61
DIVLTQSPAS LAVSLGQRAT ISCRASESVD NYGISFMNWF QQKPGQPPKL LIYAASNQGS  60
GVPARFSGSG SGTDFSLNIH PMEEDDTAMY FCQQSKEVPF TFGSGTKLEI K           111

SEQ ID NO: 62          moltype = AA  length = 119
FEATURE                Location/Qualifiers
REGION                 1..119
                       note = Synthetic
source                 1..119
                       mol_type = protein
                       organism = synthetic construct
SEQUENCE: 62
QVQLQQPGAE LVKPGASVKL SCRASGYTFT TYWMHWVKQR PGRGLEWIGW IDPNSGTTKY  60
NEKFKSKTTL TVDKPSSTAY MQLNSLTSED SAVYYCARGD SNYDYFDYWG QGTTLTVSS   119

SEQ ID NO: 63          moltype = AA  length = 109
FEATURE                Location/Qualifiers
REGION                 1..109
                       note = Synthetic
source                 1..109
                       mol_type = protein
                       organism = synthetic construct
SEQUENCE: 63
QAVVTQESAL TTSPGETVTL TCRSSTGAVT TSNYANWVQE KPDHLFTGLI GGTNNRAPGV  60
PARFSGSLIG DKAALTITGA QTEDEAIYFC ALWYSNHWVF GGGTKLTVL             109

SEQ ID NO: 64          moltype = AA  length = 120
FEATURE                Location/Qualifiers
REGION                 1..120
                       note = Synthetic
source                 1..120
                       mol_type = protein
                       organism = synthetic construct
SEQUENCE: 64
QVQLQQSGAE LVRPGASVKL SCTASGFNIK DDYMHWVKQR PEQGLEWIGW IDPENGDTEY  60
ASKFQGKATI TADTSSNTAY LQLSSLTSED TAVYYCTTDY GSSFSWFAYW GQGTLVTVSA  120

SEQ ID NO: 65          moltype = AA  length = 111
FEATURE                Location/Qualifiers
REGION                 1..111
                       note = Synthetic
source                 1..111
                       mol_type = protein
                       organism = synthetic construct
SEQUENCE: 65
DIVLTQSPAS LAVSLGQRAT ISCRASESVD NYGISFMNWF QQKPGQPPKL LIYAASNQGS  60
GVPARFSGSG SGTDFSLNIH PMEEDDTAMY FCQQSKEVPW TFGGGTKLEI K           111

SEQ ID NO: 66          moltype = AA  length = 117
FEATURE                Location/Qualifiers
REGION                 1..117
                       note = Synthetic
source                 1..117
                       mol_type = protein
                       organism = synthetic construct
SEQUENCE: 66
QVQLQQSGAE LMRPGASVRL SCTASGFDIK DYYLHWVKQR PDQGLEWIGR IDPEDGDTEY  60
```

```
APNFQGAATM TADTSSNTAY LHLNSLTSGD TAVYYCSRTG TRWIAYWGQG TLVTVSA     117

SEQ ID NO: 67          moltype = AA  length = 111
FEATURE                Location/Qualifiers
REGION                 1..111
                       note = Synthetic
source                 1..111
                       mol_type = protein
                       organism = synthetic construct
SEQUENCE: 67
DIVLTQSPAS LAVSLGQRAT ISCRASESVD NYGISFMNWF QQKPGQPPKL LIYAASNQGS  60
GVPARFSGSG SGTDFRLNIH PMEEDDTAMY FCQQSKEIPW TFGGGTKLEI K           111

SEQ ID NO: 68          moltype = AA  length = 118
FEATURE                Location/Qualifiers
REGION                 1..118
                       note = Synthetic
source                 1..118
                       mol_type = protein
                       organism = synthetic construct
SEQUENCE: 68
QVQLQQSGAE LVKPGASVKL SCTASDFNIK DFYIHWVKLR TEQGLEWIGR IDPEDGETKY  60
APKFQGKATI TADTSSNTAY LQLSSLTSED TAVYYCARAS SGPWFAYWGQ GTLVTVSA    118

SEQ ID NO: 69          moltype = AA  length = 107
FEATURE                Location/Qualifiers
REGION                 1..107
                       note = Synthetic
source                 1..107
                       mol_type = protein
                       organism = synthetic construct
SEQUENCE: 69
DIVMTQSPSS LSASLGDTIT ITCHASQNIN LWLSWYQQKP GNIPKLLISK ASNLHTGVPS  60
RFSGSGSGSG FTLTISSLQP EDIATYYCQQ GQSYPFTFGS GTKLEIK               107

SEQ ID NO: 70          moltype = AA  length = 114
FEATURE                Location/Qualifiers
REGION                 1..114
                       note = Synthetic
source                 1..114
                       mol_type = protein
                       organism = synthetic construct
SEQUENCE: 70
QVQLQQSGAE LAKPGASVRL SCKASGYTFT RYWMHWLKQR PGQGLEWIGY INPSSGYTEY  60
NQNFKDKATL TADKSSSTAY MQLSSLTYED SAVYYCARSY FDVWGTGTTV TVSS        114

SEQ ID NO: 71          moltype = AA  length = 109
FEATURE                Location/Qualifiers
REGION                 1..109
                       note = Synthetic
source                 1..109
                       mol_type = protein
                       organism = synthetic construct
SEQUENCE: 71
QAVVTQESAL TTSPGETVTL TCRSSTGAVT TSNYANWVQE KPDHLFTGLI GGTNNRAPGV  60
PARFSGSLIG DKAALTITGA QTEDEAIYFC ALWYSNHWVF GGGTKLTVL             109

SEQ ID NO: 72          moltype = AA  length = 122
FEATURE                Location/Qualifiers
REGION                 1..122
                       note = Synthetic
source                 1..122
                       mol_type = protein
                       organism = synthetic construct
SEQUENCE: 72
QVQLQQSGAE LVRPGASVKL SCTASGFNIK DDYMHWVKQR PEQGLEWIGW IDPENGDTEY  60
ASKFQGKATI TADTSSNTAY LQLSSLTSED TAVYYCTTSK NYYGSSFFFD YWGQGTTLTV  120
SS                                                                 122

SEQ ID NO: 73          moltype = AA  length = 107
FEATURE                Location/Qualifiers
REGION                 1..107
                       note = Synthetic
source                 1..107
                       mol_type = protein
                       organism = synthetic construct
SEQUENCE: 73
DIVMTQSPAT LSVTPGDRVS LSCRASQSIS DYLHWYQQKS HESPRLLIKY ASQSISGIPS  60
RFSGSGSGSD FTLSINSVEP EDVGVYYCQN GHSFPWTFGG GTKLEIK               107
```

```
SEQ ID NO: 74          moltype = AA  length = 117
FEATURE                Location/Qualifiers
REGION                 1..117
                       note = Synthetic
source                 1..117
                       mol_type = protein
                       organism = synthetic construct
SEQUENCE: 74
QVQLQQSGPE LVKPGASVKI SCKASGYAFS SSWMNWVKQR PGKGLEWIGR IYPGDGDTNY  60
NGKFKGKATL TADKSSSTAY MQLSSLTSED SAVYFCARGG GTWFAYWGQG TLVTVSA     117

SEQ ID NO: 75          moltype = AA  length = 107
FEATURE                Location/Qualifiers
REGION                 1..107
                       note = Synthetic
source                 1..107
                       mol_type = protein
                       organism = synthetic construct
SEQUENCE: 75
DIQMTQSPSS LSASLGERVS LTCRASQEIS GYLSWLQQKP DGTIKRLIYA ASTLDSGVPK  60
RFSGSRSGSD YSLTISSLES EDFANYYCLQ YATYPFTFGS GTKLEIK               107

SEQ ID NO: 76          moltype = AA  length = 115
FEATURE                Location/Qualifiers
REGION                 1..115
                       note = Synthetic
source                 1..115
                       mol_type = protein
                       organism = synthetic construct
SEQUENCE: 76
QVQLQQPGAE LVKPGASVKL SCKASGYTFT TYWMHWVKQR PGQGLEWIGE IDPSDSYTTY  60
NQKFTGKATL TVDTSSSTAY MQLSSLTSED SAVYFCLLPA WFGYWGQGTL VTVSA       115

SEQ ID NO: 77          moltype = AA  length = 107
FEATURE                Location/Qualifiers
REGION                 1..107
                       note = Synthetic
source                 1..107
                       mol_type = protein
                       organism = synthetic construct
SEQUENCE: 77
DILLTQSPAI LSVSPGERVS FSCRASQSIG TSIHWYQQRT NGSPRLLIKY ASESISGIPS  60
RFSGSGSGTD FTLSINSVES EDIADYYCQQ SNSWPTTFGG GTKLEIK               107

SEQ ID NO: 78          moltype = AA  length = 116
FEATURE                Location/Qualifiers
REGION                 1..116
                       note = Synthetic
source                 1..116
                       mol_type = protein
                       organism = synthetic construct
SEQUENCE: 78
EVQLQQSDAE LVKPGASVKI SCKVSGYTFT DHTIHWMKQR PEQGLEWIGY IYPRDGSTKY  60
NEKFKGKATL TADKSSSTAY MQLNSLTSED SAVYFCAIYR RGFAYWGQGT LVTVSA      116

SEQ ID NO: 79          moltype = AA  length = 113
FEATURE                Location/Qualifiers
REGION                 1..113
                       note = Synthetic
source                 1..113
                       mol_type = protein
                       organism = synthetic construct
SEQUENCE: 79
DIVMTQSPSS LTVTAGEKVT MSCKSSQSLL NSGNQKNYLT WYQQKPGQPP KLLIYWASTR  60
ESGVPDRFTG SGSGTDFTLT ISSVQAEDLA VYYCQNDYSY PLTFGAGTKL ELK         113

SEQ ID NO: 80          moltype = AA  length = 116
FEATURE                Location/Qualifiers
REGION                 1..116
                       note = Synthetic
source                 1..116
                       mol_type = protein
                       organism = synthetic construct
SEQUENCE: 80
EVQLQQSDAE LVKPGASVKI SCKVSGYTFT DHTIHWMKQR PEQGLEWIGY IYPRDGSTKY  60
NEKFKGKATL TADKSSSTAY MQLNSLTSED SAVYFCAFYY YGFAYWGQGT LVTVSA      116

SEQ ID NO: 81          moltype = AA  length = 109
```

```
FEATURE                Location/Qualifiers
REGION                 1..109
                       note = Synthetic
source                 1..109
                       mol_type = protein
                       organism = synthetic construct
SEQUENCE: 81
QAVVTQESAL TTSPGETVTL TCRSSTGAVT TSNYANWVQE KPDHLFTGLI GGTNNRAPGV  60
PARFSGSLIG DKAALTITGA QTEDEAIYFC ALWYSNHWVF GGGTKLTVL              109

SEQ ID NO: 82          moltype = AA  length = 119
FEATURE                Location/Qualifiers
REGION                 1..119
                       note = Synthetic
source                 1..119
                       mol_type = protein
                       organism = synthetic construct
SEQUENCE: 82
QVQLQQSGAE LVRPGASVKL SCTASGFNIK DDYMHWVKQR PEQGLEWIGW IDPENGDTEY  60
ASKFQGKATI TADTSSNTAY LQLSSLTSED TAVYYCTTYY YGSSDFAYWG QGTLVTVSA   119

SEQ ID NO: 83          moltype = AA  length = 112
FEATURE                Location/Qualifiers
REGION                 1..112
                       note = Synthetic
source                 1..112
                       mol_type = protein
                       organism = synthetic construct
SEQUENCE: 83
DIVMTQTPLS LPVTPGEPAS ISCRSSQSLL HSNEYNYLDW YLQKPGQSPQ LLIYLGSNRA  60
SGVPDRFSGS GSVTDFTLKI SRVEADDLGV YYCMQALQTP YTFGQGTKLE IK          112

SEQ ID NO: 84          moltype = AA  length = 124
FEATURE                Location/Qualifiers
REGION                 1..124
                       note = Synthetic
source                 1..124
                       mol_type = protein
                       organism = synthetic construct
SEQUENCE: 84
EVQLVESGGG VVQPGGSLRL SCATSGFTFS SYTMNWVRQA PGKGLEWVSC ISSSGSAIYF  60
ADSVKGRFAI SRDNVKNSLY LQMNSLRDED TAVYYCARGG YSSSSRYHDA FDIWGQGTMV  120
TVSS                                                               124

SEQ ID NO: 85          moltype = AA  length = 108
FEATURE                Location/Qualifiers
REGION                 1..108
                       note = Synthetic
source                 1..108
                       mol_type = protein
                       organism = synthetic construct
SEQUENCE: 85
EIVVTQSPAT LSLSPGERAT LSCRASQSVS SSYLAWYQQK PGQAPRLLIY GTSSRATGIP  60
DRFSGSGSGT DFTLIITRLE PEDFVVYYCQ QYGTSPRTFG QGTKVEIK               108

SEQ ID NO: 86          moltype = AA  length = 119
FEATURE                Location/Qualifiers
REGION                 1..119
                       note = Synthetic
source                 1..119
                       mol_type = protein
                       organism = synthetic construct
SEQUENCE: 86
QVQLQESGPG LVKPSGTLSL TCAVSGGSIS SINWWSWVRQ PPGKGLEWIG EIYHSGSTNY  60
NPSLKSRVTI SVDKSKNQFS LKLSSMTAAD TAVYYCARDE SGYDYFDYWG QGTLVTVSS   119

SEQ ID NO: 87          moltype = AA  length = 113
FEATURE                Location/Qualifiers
REGION                 1..113
                       note = Synthetic
source                 1..113
                       mol_type = protein
                       organism = synthetic construct
SEQUENCE: 87
DIVMTQSPDS LAVSLGERAT INCKSSQNVL YSSNNENYLA WYQQKPGQPP NLLIYWASTR  60
ESGVPDRFSG SGSGTDFTLT ISSLQAEDVA VYYCQQYYST PPTFGGGTKV EIK          113

SEQ ID NO: 88          moltype = AA  length = 120
FEATURE                Location/Qualifiers
```

-continued

```
REGION                  1..120
                        note = Synthetic
source                  1..120
                        mol_type = protein
                        organism = synthetic construct
SEQUENCE: 88
QVQLVESGGG VVQPGRSLRL SCAASGFTFS SYGMHWVRQA PGKGLEWVAV IWYDGGNKYY  60
ADSVKGRFII SRDNSRDTLY LQMNSLRAED TAVYYCARDW GSSWYLFDHW GQGTLVTVSS  120

SEQ ID NO: 89           moltype = AA  length = 107
FEATURE                 Location/Qualifiers
REGION                  1..107
                        note = Synthetic
source                  1..107
                        mol_type = protein
                        organism = synthetic construct
SEQUENCE: 89
DIQMTQSPSS LSASVGDRVT ITCRASQSIS NFLNWYQQRP GKVPKLLINA ASSLQSGVPS  60
RFSGRGSGTD FTLTIGSLQP EDFATYYCQQ SYITPLTFGG GTKVEIK                107

SEQ ID NO: 90           moltype = AA  length = 116
FEATURE                 Location/Qualifiers
REGION                  1..116
                        note = Synthetic
source                  1..116
                        mol_type = protein
                        organism = synthetic construct
SEQUENCE: 90
EVQLVESGGG LVQPGGSLRL SCAASGFTFS SYDMHWVRQP TGKGLEWVSS IGTAGNTNYP  60
GSVKGRFTIS RENAKNSLYL QMNSLRAGDT AVYYCARWVN WYFGLWGRGT LVTVSS      116

SEQ ID NO: 91           moltype = AA  length = 113
FEATURE                 Location/Qualifiers
REGION                  1..113
                        note = Synthetic
source                  1..113
                        mol_type = protein
                        organism = synthetic construct
SEQUENCE: 91
DIVMTQSPDS LAVSLGERAT IDCKSSQNVL YSSNNKNYLA WYQQKPGQPP KLIIYWASTR  60
ESGVPDRFSG SGSGTDFTLT ITSLQAEDVA IYYCQQYYST PLTFGGGTKV EIK         113

SEQ ID NO: 92           moltype = AA  length = 120
FEATURE                 Location/Qualifiers
REGION                  1..120
                        note = Synthetic
source                  1..120
                        mol_type = protein
                        organism = synthetic construct
SEQUENCE: 92
QVQLQESGPG LVKPSQTLSL TCTVSGGSFS SGGYYWSWIR QHPGKGLEWI GYIYYSGTTY  60
YTPSLKSRIT ISVDTSENQF SLKLNSVTAA DTAVYYCARA GFGYYYMDVW GKGTTVTVSS  120

SEQ ID NO: 93           moltype = AA  length = 108
FEATURE                 Location/Qualifiers
REGION                  1..108
                        note = Synthetic
source                  1..108
                        mol_type = protein
                        organism = synthetic construct
SEQUENCE: 93
EIVLTQSPAT LSLSPGERAT LSCRASQSVS SSYLAWYQQK PGQAPRLLIY GASSRATGIP  60
DRFSGSGSGT DFTLTISRLE PEDFAVYYCQ QYGSSPRTFG QGTKVEIK               108

SEQ ID NO: 94           moltype = AA  length = 121
FEATURE                 Location/Qualifiers
REGION                  1..121
                        note = Synthetic
source                  1..121
                        mol_type = protein
                        organism = synthetic construct
SEQUENCE: 94
EVQLVESGGG LVQPGGSLRL SCAASGFTFS SYAMSWVRQV SGKGLEWVSA ISGTGGNIYY  60
TDSVQDRFTI SRDNFKKTLY LHMNSLRAED TAVYYCAKSS YSGNFHVFDF WGQGTLVTVS  120
S                                                                  121

SEQ ID NO: 95           moltype = AA  length = 107
FEATURE                 Location/Qualifiers
REGION                  1..107
```

```
                        note = Synthetic
source                  1..107
                        mol_type = protein
                        organism = synthetic construct
SEQUENCE: 95
EIVLTQSPAT LSLSPGERAT LSCRASQSVS SSYLAWYQQK PGQAPRLLIY GASSRATGIP  60
DRFSGSGSGT DFTLTISRLE PEDFAVYYCQ QYGSSYTFGQ GTKLEIK               107

SEQ ID NO: 96           moltype = AA  length = 122
FEATURE                 Location/Qualifiers
REGION                  1..122
                        note = Synthetic
source                  1..122
                        mol_type = protein
                        organism = synthetic construct
SEQUENCE: 96
QVQLVQSGAE VKKPGASVKV SCKASGYTFT SYDINWVRQA TGQGLEWMGW MNPNSGNTGY  60
AQKFQGRVTM TRNTSISTAY MEMSSLRYED TAVYYCARRR LYNWNWGWFD PWGQGTLVTV  120
SS                                                                122

SEQ ID NO: 97           moltype = AA  length = 113
FEATURE                 Location/Qualifiers
REGION                  1..113
                        note = Synthetic
source                  1..113
                        mol_type = protein
                        organism = synthetic construct
SEQUENCE: 97
DIVMTQSPDS LAVSLGERAT INCKSSQSVL YSSNNKNYLA WYQQKPGQPP KLLIFWASTR  60
ESGVPDRFSG SGSGTDFTLT ISSLQAEDVA VYYCQQYYST PPTFGGGTKV EIK        113

SEQ ID NO: 98           moltype = AA  length = 122
FEATURE                 Location/Qualifiers
REGION                  1..122
                        note = Synthetic
source                  1..122
                        mol_type = protein
                        organism = synthetic construct
SEQUENCE: 98
EVQLVESGGG LVQPGRSLRL SCAASGFTFD DYAMHWVRQA PGKGLEWVSG ISWNRGSIDY  60
ADSVKGRFTI SRDNAKNSLY LQMNSLRAED TALYYCAKDI GITGTTEAFD IWGQGTMVTV  120
SS                                                                122

SEQ ID NO: 99           moltype = AA  length = 107
FEATURE                 Location/Qualifiers
REGION                  1..107
                        note = Synthetic
source                  1..107
                        mol_type = protein
                        organism = synthetic construct
SEQUENCE: 99
DIQMTQSPSS LSASVGDRVT ITCRASQGIN IWLAWYQQKP GKAPKLLIYA ASSLQSGVPS  60
RFSGSGSGTD FTLTISSLQP EDFATYYCQQ ANSFPITFGQ GTRLEIK               107

SEQ ID NO: 100          moltype = AA  length = 132
FEATURE                 Location/Qualifiers
REGION                  1..132
                        note = Synthetic
source                  1..132
                        mol_type = protein
                        organism = synthetic construct
SEQUENCE: 100
QVQLQESGPG LVKPSQTLSL TCTVSGGSIS SGGYYWSWIR QHPGKGLEWI GYIYYSGNTY  60
YNPSLKSRVA ISVGTSKNQF SLKLSSVTAA DTAVYYCARG GYYYGPGSYG DNSSGYYYFD  120
YWGQGTLVTV SS                                                     132

SEQ ID NO: 101          moltype = AA  length = 107
FEATURE                 Location/Qualifiers
REGION                  1..107
                        note = Synthetic
source                  1..107
                        mol_type = protein
                        organism = synthetic construct
SEQUENCE: 101
EIVLTQSPAT LSLSPGERAI LSCRASQSVS IYLAWYQQKP GQAPRLLIYD ASDRATGIPA  60
RFSGSGSETD FTLTISSLEP EDFAVYYCQQ RNNWPLTFGG GTKVEIK               107

SEQ ID NO: 102          moltype = AA  length = 121
FEATURE                 Location/Qualifiers
```

-continued

```
REGION                1..121
                      note = Synthetic
source                1..121
                      mol_type = protein
                      organism = synthetic construct
SEQUENCE: 102
EVQLVESGGG LVQPGGSLRL SCAASGFTFS SYAMSWVRQV SGKGLEWVSA ISGTGGNIYY  60
TDSVQDRFTI SRDNFKKTLY LHMNSLRAED TAVYYCAKSS YSGNFHVFDF WGQGTLVTVS  120
S                                                                  121

SEQ ID NO: 103        moltype = AA  length = 107
FEATURE               Location/Qualifiers
REGION                1..107
                      note = Synthetic
source                1..107
                      mol_type = protein
                      organism = synthetic construct
SEQUENCE: 103
EIVLTQSPAT LSLSPGERAT LSCRASQSVS SYLAWYQQKT GQAPRLLIYD ASDRATGIPA  60
RFSGSGSGTD FTLTISSLEP EDFAVYYCQQ RGNWPLTFGG GTKVEIK                107

SEQ ID NO: 104        moltype = AA  length = 121
FEATURE               Location/Qualifiers
REGION                1..121
                      note = Synthetic
source                1..121
                      mol_type = protein
                      organism = synthetic construct
SEQUENCE: 104
EVQLVESGGD LVQPGGSLRL SCAASGFSFS GYAMSWVRQV PGKGLEWVSA ISGSGGNTYY  60
ADSVKGRFTI SRDNSKNTLY LQMNSLRAED TAVYYCAKSS LSGNFHVFDF WGQGTLVTVS  120
S                                                                  121

SEQ ID NO: 105        moltype = AA  length = 107
FEATURE               Location/Qualifiers
REGION                1..107
                      note = Synthetic
source                1..107
                      mol_type = protein
                      organism = synthetic construct
SEQUENCE: 105
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPLTFGG GTKVEIK                107

SEQ ID NO: 106        moltype = AA  length = 122
FEATURE               Location/Qualifiers
REGION                1..122
                      note = Synthetic
source                1..122
                      mol_type = protein
                      organism = synthetic construct
SEQUENCE: 106
QVQLQESGPG LVKPSQTLSL TCAISGDSVS TNSAAWNWIR QSPSRGLEWL GRTYYRSKWY  60
NDYAVSVTSR ITINPDTSKN QFSLQLNSVT PEDTAVYYCA RDWWELIFFD YWGQGTLVTV  120
SS                                                                 122

SEQ ID NO: 107        moltype = AA  length = 106
FEATURE               Location/Qualifiers
REGION                1..106
                      note = Synthetic
source                1..106
                      mol_type = protein
                      organism = synthetic construct
SEQUENCE: 107
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNSITFGQG TRLEIK                 106

SEQ ID NO: 108        moltype = AA  length = 121
FEATURE               Location/Qualifiers
REGION                1..121
                      note = Synthetic
source                1..121
                      mol_type = protein
                      organism = synthetic construct
SEQUENCE: 108
EVQLVESGGG LVKPGGSLRL SCAASGFTFS SYSMNWVRQA PGKGLEWVSS ISSSTSYRYY  60
ADSVKGRFTI SRDNAKNSLY LQMNSLRAED TAVYYCARES GGVTNNWFDP WGQGTLVTVS  120
S                                                                  121
```

-continued

```
SEQ ID NO: 109          moltype = AA  length = 113
FEATURE                 Location/Qualifiers
REGION                  1..113
                        note = Synthetic
source                  1..113
                        mol_type = protein
                        organism = synthetic construct
SEQUENCE: 109
DIVMTQSPDS LAVSLGERAT ITCKSSQNVL YNSNNKNYLA WYQQKPGQPP KLLIYWASTR  60
ESGVPDRFSG SGSGTDFTLT ISSLQAEDVA VYCCQQYYSI PYTFGQGTKV EIK         113

SEQ ID NO: 110          moltype = AA  length = 125
FEATURE                 Location/Qualifiers
REGION                  1..125
                        note = Synthetic
source                  1..125
                        mol_type = protein
                        organism = synthetic construct
SEQUENCE: 110
EVQLVESGGG LVKPGGSLRL SCVVSGFTFS RFTMNWVRQA PGKGLEWVSS ISTSSSYIYY  60
GDSVKGRFTI SRDNAKNSLH LQMNSLRAED TAVYYCAREG GDWNHDYNYY YMDVWGKGTT  120
VTVSS                                                              125

SEQ ID NO: 111          moltype = AA  length = 113
FEATURE                 Location/Qualifiers
REGION                  1..113
                        note = Synthetic
source                  1..113
                        mol_type = protein
                        organism = synthetic construct
SEQUENCE: 111
DIVMTQSPDS LAVSLGERAT VTCKSSQNVL YNSNNKNYLA WYQQKPGQPP NLLIYWASTR  60
ESGVPDRFSG SGSGTDFTLT ISSLQAEDVA IYYCQQYYST PYTFGQGTKL EIK         113

SEQ ID NO: 112          moltype = AA  length = 125
FEATURE                 Location/Qualifiers
REGION                  1..125
                        note = Synthetic
source                  1..125
                        mol_type = protein
                        organism = synthetic construct
SEQUENCE: 112
EVQLVESGGG LVKPGGSLRI SCVVSGFTFS RFTMNWVRQA PGKGLEWVSS ISSTSSYVYY  60
GDSVKGRFTI SRDNAKNSLY LQMNSLRAED TAVYYCAREG GDWNYDYNYY YMDVWGKGTT  120
VTVSS                                                              125

SEQ ID NO: 113          moltype = AA  length = 107
FEATURE                 Location/Qualifiers
REGION                  1..107
                        note = Synthetic
source                  1..107
                        mol_type = protein
                        organism = synthetic construct
SEQUENCE: 113
DIQMTQSPSS VSASVGDRVT ITCRASQGIS SWLAWYQQKP GKAPKLLIYE ASSLQSGVPS  60
RFSGSGSGTD FTLTISSLQP EDFATYYCQQ DNSFPFTFGP GTKVDIK               107

SEQ ID NO: 114          moltype = AA  length = 117
FEATURE                 Location/Qualifiers
REGION                  1..117
                        note = Synthetic
source                  1..117
                        mol_type = protein
                        organism = synthetic construct
SEQUENCE: 114
QVQLVQSGSE LKKPGASVKV SCKASGYTFT SYAMNWVRQA PGQGLEWMGW INTNTGNPTY  60
AQGFTGRFVF SLDTSVSTAY LQISSLKAED TAVYYCARSL YWYFDLWGRG TLVTVSS     117

SEQ ID NO: 115          moltype = AA  length = 107
FEATURE                 Location/Qualifiers
REGION                  1..107
                        note = Synthetic
source                  1..107
                        mol_type = protein
                        organism = synthetic construct
SEQUENCE: 115
DIQMTQSPSS LSASVGDRVT ITCQANQDIT NYLNWYQQKP GKAPKLLIYD ASNLETGVPS  60
RFSGSGSGTD FTFTISSLQP EDIATYYCQQ YDNLPLTFGG GTKVEIK               107
```

```
SEQ ID NO: 116          moltype = AA  length = 122
FEATURE                 Location/Qualifiers
REGION                  1..122
                        note = Synthetic
source                  1..122
                        mol_type = protein
                        organism = synthetic construct
SEQUENCE: 116
EVQLVESGGG LVQPGGSLKL SCAASGFTFS GSAMDWVRQA SGKGLEWVGR IRSKANNYAT  60
AYAASVKGRF TISRDDSKNT AYLQMNSLKT EDTAVYYCTS RGYSGYDLFD YWGQGTLVTV  120
SS                                                                122

SEQ ID NO: 117          moltype = AA  length = 107
FEATURE                 Location/Qualifiers
REGION                  1..107
                        note = Synthetic
source                  1..107
                        mol_type = protein
                        organism = synthetic construct
SEQUENCE: 117
DIQMTQSPSS LSASVGDRVT ITCQASQDIS NYLNWYQQKP GKAPKVLIYD ASNLETGVPS  60
RFSGSGSGTD FTFTISSLQP EDIATYYCQQ YDNLPLTFGG GTKVEIK               107

SEQ ID NO: 118          moltype = AA  length = 125
FEATURE                 Location/Qualifiers
REGION                  1..125
                        note = Synthetic
source                  1..125
                        mol_type = protein
                        organism = synthetic construct
SEQUENCE: 118
EVQLVESGGG LVQPGGSLKL SCAASGFTFS GSAMHWVRQA SGKGLEWVGR IRSKANSYAT  60
AYAASVKGRF TISRDDSKNT AYLQMNSLKT EDTAVYYCTS RGYSGYDYSS YFDYWGQGTL  120
VTVSS                                                             125

SEQ ID NO: 119          moltype = AA  length = 108
FEATURE                 Location/Qualifiers
REGION                  1..108
                        note = Synthetic
source                  1..108
                        mol_type = protein
                        organism = synthetic construct
SEQUENCE: 119
EIVLTQSPAT LSLSPGERAT LSCRASQSFS SSYLAWYQQK PGQVPRLLIY GASSRATGIP  60
DRFSGSGSGT DFTLTISRLE PEDFAVYYCQ QYGSSPYTFG QGTKLEIK              108

SEQ ID NO: 120          moltype = AA  length = 123
FEATURE                 Location/Qualifiers
REGION                  1..123
                        note = Synthetic
source                  1..123
                        mol_type = protein
                        organism = synthetic construct
SEQUENCE: 120
QVQLQESGPG LVKPSGTLSL TCAVSGGSIS SSDWWSWVRQ PPGKGLEWLG EIHHSGNTNY  60
NPSLKSRVTI SVDKSKNHFS LKLRSVTAAD TAVYYCARLY SDGYNYYYYM DVWGKGTTVT  120
VSS                                                               123

SEQ ID NO: 121          moltype = AA  length = 107
FEATURE                 Location/Qualifiers
REGION                  1..107
                        note = Synthetic
source                  1..107
                        mol_type = protein
                        organism = synthetic construct
SEQUENCE: 121
DIQMTQSPSS LSASVGDRVT ITCQASQDIS NYLNWYQQKP GKAPKVLIYD ASNLEKGVPS  60
RFSGSGSGTD FTFTISSLQP EDIGTYYCQQ YDNLPITFGG GTKVEIK               107

SEQ ID NO: 122          moltype = AA  length = 125
FEATURE                 Location/Qualifiers
REGION                  1..125
                        note = Synthetic
source                  1..125
                        mol_type = protein
                        organism = synthetic construct
SEQUENCE: 122
EVQLVESGGG LVQPGGSLKL SCAASGFTFS GSAMHWVRQA SGKGLEWIGR IRSKANNDAT  60
SYDASVKGRF TISRNDSKNT AYLQMNSLKT EDTAVYYCTS RGYSGYDYSS YFDYWGQGTL  120
```

```
VTVSS                                                           125

SEQ ID NO: 123         moltype = AA  length = 108
FEATURE                Location/Qualifiers
REGION                 1..108
                       note = Synthetic
source                 1..108
                       mol_type = protein
                       organism = synthetic construct
SEQUENCE: 123
EIVLTQSPAT LSLSPGERAT LSCRASQSVS SNFLAWYQQK PGQAPRLLIY GASSRATGIP  60
DRFSGSGSGT DFTLTISRLE PEDFAVYYCQ QYGNSPWTFG QGTKVEIK              108

SEQ ID NO: 124         moltype = AA  length = 125
FEATURE                Location/Qualifiers
REGION                 1..125
                       note = Synthetic
source                 1..125
                       mol_type = protein
                       organism = synthetic construct
SEQUENCE: 124
QVQLQESGPG LVKPSQTLSL TCAISGDSVS SNSAAWNWIR QSPSRGLEWL GRTYYRSKWY  60
NDYAVSVKGR IAINPDTSKN HFSLQLTSVT PEDTAVYYCA RDPRFTWNYG AFDIWGQGTM  120
VTVSS                                                           125

SEQ ID NO: 125         moltype = AA  length = 107
FEATURE                Location/Qualifiers
REGION                 1..107
                       note = Synthetic
source                 1..107
                       mol_type = protein
                       organism = synthetic construct
SEQUENCE: 125
DIQMTQSPSS LSASVGDRVT ITCQASQDIS NYLNWYQQKP GKAPKVLIYD ASNLETGVPS  60
RFSGSGSGTD FTFTISSLQP EDIATYYCQQ YDNVPLTFGG GTKVEIK               107

SEQ ID NO: 126         moltype = AA  length = 125
FEATURE                Location/Qualifiers
REGION                 1..125
                       note = Synthetic
source                 1..125
                       mol_type = protein
                       organism = synthetic construct
SEQUENCE: 126
EVQLVESGGG LVQPGGSLKL SCAASGFTFS GSAMHWVRQA SGKGLEWVGR IRSKANNYAT  60
AYAASVKVRF TISRDDSMTT AYLHMNSLKT EDTAVYYCTS RGFSGYDYSS YFDYWGQGTL  120
VTVSS                                                           125

SEQ ID NO: 127         moltype = AA  length = 107
FEATURE                Location/Qualifiers
REGION                 1..107
                       note = Synthetic
source                 1..107
                       mol_type = protein
                       organism = synthetic construct
SEQUENCE: 127
DIQMTQSPSS LSASVGDRVT ITCQASQDIR NYLNWYQQKP GKAPKLLIYD ASNLETGVPS  60
RFSGSGSGTD FTFTISSLQP EDIATYYCQP YDNLMYTFGG GTKVEIK               107

SEQ ID NO: 128         moltype = AA  length = 117
FEATURE                Location/Qualifiers
REGION                 1..117
                       note = Synthetic
source                 1..117
                       mol_type = protein
                       organism = synthetic construct
SEQUENCE: 128
EVQLVESGGG LVQPGGSLRL SCAASGFTFS SYDMHWVRQA TGKGLEWVSG INTDGDTFYP  60
GSVKGRFTIS RENAKNSLYL QMNSLRAGDT AVYYCARRGW NYGFDYWGQG TLVTVSS     117

SEQ ID NO: 129         moltype = AA  length = 107
FEATURE                Location/Qualifiers
REGION                 1..107
                       note = Synthetic
source                 1..107
                       mol_type = protein
                       organism = synthetic construct
SEQUENCE: 129
DIQMTQSPSS LSASVGDRVT ITCQANQDIT NYLNWYQQKP GKAPKLLIYD ASNLETGVPS  60
```

```
RFSGSGSGTD FTFTISSLQP EDIATYYCQQ YDNLPLTFGG GTKVEIK              107

SEQ ID NO: 130         moltype = AA  length = 122
FEATURE                Location/Qualifiers
REGION                 1..122
                       note = Synthetic
source                 1..122
                       mol_type = protein
                       organism = synthetic construct
SEQUENCE: 130
EVQLVESGGG LVQPGGSLKL SCAASGFTFS GSAMDWVRQA SGKGLEWVGR IRSKANNYAT  60
AYAASVKGRF TISRDDSKNT AYLQMNSLKT EDTAVYYCTS RGYSGYDLFD YWGQGTLVTV  120
SS                                                               122

SEQ ID NO: 131         moltype = AA  length = 107
FEATURE                Location/Qualifiers
REGION                 1..107
                       note = Synthetic
source                 1..107
                       mol_type = protein
                       organism = synthetic construct
SEQUENCE: 131
DIQMTQSPSS LSASVGDRVT ITCQASQDIS NYLNWYQQKP GKAPKVLIYD ASNLETGVPS  60
RFSGSGSGTD FTFTISSLQP EDIATYYCQQ YDNLPLTFGG GTKVEIK              107

SEQ ID NO: 132         moltype = AA  length = 125
FEATURE                Location/Qualifiers
REGION                 1..125
                       note = Synthetic
source                 1..125
                       mol_type = protein
                       organism = synthetic construct
SEQUENCE: 132
EVQLVESGGG LVQPGGSLKL SCAASGFTFS GSAMHWVRQA SGKGLEWVGR IRSKANNYAT  60
AYAASVKGRF TISRDDSKNT AYLQMNSLKT EDTAVYYCTS RGYSGYDYSS YFDYWGQGTL  120
VTVSS                                                            125

SEQ ID NO: 133         moltype = AA  length = 107
FEATURE                Location/Qualifiers
REGION                 1..107
                       note = Synthetic
source                 1..107
                       mol_type = protein
                       organism = synthetic construct
SEQUENCE: 133
DIQMTQSPSS LSASVGDRVT ITCRASQGIS NYLAWYQQKP GKVPKLLIYA ASTLQSGVPS  60
RFSGSGSGTD FTLTISSLQP EDVATYYCQK YNSAPLTFGG GTKVEIK              107

SEQ ID NO: 134         moltype = AA  length = 121
FEATURE                Location/Qualifiers
REGION                 1..121
                       note = Synthetic
source                 1..121
                       mol_type = protein
                       organism = synthetic construct
SEQUENCE: 134
QVQLQESGPG LVKPSGTLSL TCAVSAGSIS SSNWWSWVRQ PPGKGLEWIG EISHSGSTNY  60
NPSLKSRVTI SVDKSKNQFS LKLSSVTAAD TAVYYCARYN SGDDVDWFDP WGQGTLVSVS  120
S                                                                121

SEQ ID NO: 135         moltype = AA  length = 107
FEATURE                Location/Qualifiers
REGION                 1..107
                       note = Synthetic
source                 1..107
                       mol_type = protein
                       organism = synthetic construct
SEQUENCE: 135
EIVMTQSPAT LSLSPGERAT LSCRASQSVN NNLAWYQQKP GQAPRLLIYG ASTRATGIPA  60
RFSGSGSGTE FTLTISSLQS EDFAVYYCQQ YNNWPLTFGG GTKVEIK              107

SEQ ID NO: 136         moltype = AA  length = 123
FEATURE                Location/Qualifiers
REGION                 1..123
                       note = Synthetic
source                 1..123
                       mol_type = protein
                       organism = synthetic construct
SEQUENCE: 136
```

```
QVQLVQSGAE VKKPGASVKV SCKASGYTFT GYDMHWVRQA PGQGLEWMGW INPNSGGTNY  60
AQKFQGRVTM TRDTSITTVY MELSRLRYDD TAVYYCARDG SLAARPHNWF DPWGQGTLVT  120
VSS                                                                123

SEQ ID NO: 137         moltype = AA  length = 107
FEATURE                Location/Qualifiers
REGION                 1..107
                       note = Synthetic
source                 1..107
                       mol_type = protein
                       organism = synthetic construct
SEQUENCE: 137
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYIIPFTFGP GTKLDIK               107

SEQ ID NO: 138         moltype = AA  length = 121
FEATURE                Location/Qualifiers
REGION                 1..121
                       note = Synthetic
source                 1..121
                       mol_type = protein
                       organism = synthetic construct
SEQUENCE: 138
QVQLQESGPG LVKPSQTLSL TCAISGDSVS SNSAAWNWIR QSPSRGLEWL GRTYYRSKWY  60
NDYAVSVKSR ITINPDTSKN QFSLQLNSVT PEDTAVYYCA RAPNWGSFDY WGQGTLVTVS  120
S                                                                  121

SEQ ID NO: 139         moltype = AA  length = 107
FEATURE                Location/Qualifiers
REGION                 1..107
                       note = Synthetic
source                 1..107
                       mol_type = protein
                       organism = synthetic construct
SEQUENCE: 139
DIQMTQSPSS LSASVGDRVT ITCQASQDIR NYLNWYQQKP GKAPKVLIYD ASNLETGVPS  60
RFSGSGSGTD FTFTISSLQP EDIATYYCQQ YDNLPITFGQ GTRLEIK               107

SEQ ID NO: 140         moltype = AA  length = 122
FEATURE                Location/Qualifiers
REGION                 1..122
                       note = Synthetic
source                 1..122
                       mol_type = protein
                       organism = synthetic construct
SEQUENCE: 140
EVQLVESGGG LVQPGGSLKL SCAASGFTFS GSAMHWVRQA SGKGLEWVGR IRSKANNYAT  60
VYAASVKGRF TISRDDSKST AYLQMNSLKT EDTAVYYCAS RGYSAYDYFD YWGQGTLVTV  120
SS                                                                 122

SEQ ID NO: 141         moltype = AA  length = 107
FEATURE                Location/Qualifiers
REGION                 1..107
                       note = Synthetic
source                 1..107
                       mol_type = protein
                       organism = synthetic construct
SEQUENCE: 141
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYIIPFTFGP GTKLDIK               107

SEQ ID NO: 142         moltype = AA  length = 121
FEATURE                Location/Qualifiers
REGION                 1..121
                       note = Synthetic
source                 1..121
                       mol_type = protein
                       organism = synthetic construct
SEQUENCE: 142
QVQLQESGPG LVKPSQTLSL TCAISGDSVS SNSAAWNWIR QSPSRGLEWL GRTYYRSKWY  60
NDYAVSVKSR ITINPDTSKN QFSLQLNSVT PEDTAVYYCA RAPNWGSFDY WGQGTLVTVS  120
S                                                                  121

SEQ ID NO: 143         moltype = AA  length = 107
FEATURE                Location/Qualifiers
REGION                 1..107
                       note = Synthetic
source                 1..107
                       mol_type = protein
```

```
                        organism = synthetic construct
SEQUENCE: 143
DIQMTQSPSS LSASVGDRVT ITCRASQDIS NYLNWYQQKP GKAPKLLIYD ASNLDKGVPS  60
GFSGSGSGTD FTFTISSLQP EHIATYYCQQ YDNLPITFGQ GTRLEIK               107

SEQ ID NO: 144          moltype = AA  length = 122
FEATURE                 Location/Qualifiers
REGION                  1..122
                        note = Synthetic
source                  1..122
                        mol_type = protein
                        organism = synthetic construct
SEQUENCE: 144
EVQLVESGGG LVQPGGSLKL SCAASGFTFS GCAMHWVRQA SGKGLEWVGR IRSKANNYAT  60
TYAASVKGRF TISRDDSKNT AYLQMNSLKT EDTAVYYCTS RGYSGFDWFD YWGQGTLVSV  120
SS                                                                 122

SEQ ID NO: 145          moltype = AA  length = 107
FEATURE                 Location/Qualifiers
REGION                  1..107
                        note = Synthetic
source                  1..107
                        mol_type = protein
                        organism = synthetic construct
SEQUENCE: 145
DIQMTQSPSS LSASVGDRVS ITCRASQSIS SYLNWYQQKP GKAPKLLIYA ASSLQSGVPS  60
RFSGSGSGTD FTLTISSLQP EDFATYYCQQ SYSTPLTFGG GTKVEIK               107

SEQ ID NO: 146          moltype = AA  length = 123
FEATURE                 Location/Qualifiers
REGION                  1..123
                        note = Synthetic
source                  1..123
                        mol_type = protein
                        organism = synthetic construct
SEQUENCE: 146
QVQLVQSGAE VKKPGASVKV SCKASGYTFT SYDINWVRQA TGQGLEWMGW MNPNSGNTGY  60
AQKFQGRVTM TRNTSISTAY MELSSLRSED TAVYYCARRV WIAARPANWF DPWGQGTLVT  120
VSS                                                                123

SEQ ID NO: 147          moltype = AA  length = 111
FEATURE                 Location/Qualifiers
REGION                  1..111
                        note = Synthetic
source                  1..111
                        mol_type = protein
                        organism = synthetic construct
SEQUENCE: 147
EIVLTQSPAT LSLSPGERAT LSCRASESVD SYGKSFMHWY QQKPGQAPRL LIYRASNLES  60
GIPARFSGSG SGTDFTLTIS SLEPEDFAVY YCQQSNEDPW TFGGGTKLEI K           111

SEQ ID NO: 148          moltype = AA  length = 119
FEATURE                 Location/Qualifiers
REGION                  1..119
                        note = Synthetic
source                  1..119
                        mol_type = protein
                        organism = synthetic construct
SEQUENCE: 148
QVQLVQSGPE VKKPGASVKV SCKASGYTFT DYAVHWVRQA PGKRLEWIGV ISTYNDYTYN  60
NQDFKGRVTM TRDTSASTAY MELSRLRSED TAVYYCARGN SYFYALDYWG QGTSVTVSS   119

SEQ ID NO: 149          moltype = AA  length = 5
FEATURE                 Location/Qualifiers
REGION                  1..5
                        note = Synthetic
source                  1..5
                        mol_type = protein
                        organism = synthetic construct
SEQUENCE: 149
TYWMH                                                              5

SEQ ID NO: 150          moltype = AA  length = 7
FEATURE                 Location/Qualifiers
REGION                  1..7
                        note = Synthetic
source                  1..7
                        mol_type = protein
                        organism = synthetic construct
```

```
SEQUENCE: 150
GYTFTTY                                                           7

SEQ ID NO: 151          moltype = AA  length = 8
FEATURE                 Location/Qualifiers
REGION                  1..8
                        note = Synthetic
source                  1..8
                        mol_type = protein
                        organism = synthetic construct
SEQUENCE: 151
GYTFTTYW                                                          8

SEQ ID NO: 152          moltype = AA  length = 13
FEATURE                 Location/Qualifiers
REGION                  1..13
                        note = Synthetic
source                  1..13
                        mol_type = protein
                        organism = synthetic construct
SEQUENCE: 152
KASGYTFTTY WMH                                                    13

SEQ ID NO: 153          moltype = AA  length = 6
FEATURE                 Location/Qualifiers
REGION                  1..6
                        note = Synthetic
source                  1..6
                        mol_type = protein
                        organism = synthetic construct
SEQUENCE: 153
TTYWMH                                                            6

SEQ ID NO: 154          moltype = AA  length = 10
FEATURE                 Location/Qualifiers
REGION                  1..10
                        note = Synthetic
source                  1..10
                        mol_type = protein
                        organism = synthetic construct
SEQUENCE: 154
GYTFTTYWMH                                                        10

SEQ ID NO: 155          moltype = AA  length = 17
FEATURE                 Location/Qualifiers
REGION                  1..17
                        note = Synthetic
source                  1..17
                        mol_type = protein
                        organism = synthetic construct
SEQUENCE: 155
EIDPSDSYTT YNQKFTG                                                17

SEQ ID NO: 156          moltype = AA  length = 6
FEATURE                 Location/Qualifiers
REGION                  1..6
                        note = Synthetic
source                  1..6
                        mol_type = protein
                        organism = synthetic construct
SEQUENCE: 156
DPSDSY                                                            6

SEQ ID NO: 157          moltype = AA  length = 8
FEATURE                 Location/Qualifiers
REGION                  1..8
                        note = Synthetic
source                  1..8
                        mol_type = protein
                        organism = synthetic construct
SEQUENCE: 157
IDPSDSYT                                                          8

SEQ ID NO: 158          moltype = AA  length = 10
FEATURE                 Location/Qualifiers
REGION                  1..10
                        note = Synthetic
source                  1..10
                        mol_type = protein
```

```
                        organism = synthetic construct
SEQUENCE: 158
EIDPSDSYTT                                                          10

SEQ ID NO: 159          moltype = AA  length = 13
FEATURE                 Location/Qualifiers
REGION                  1..13
                        note = Synthetic
source                  1..13
                        mol_type = protein
                        organism = synthetic construct
SEQUENCE: 159
WIGEIDPSDS YTT                                                      13

SEQ ID NO: 160          moltype = AA  length = 6
FEATURE                 Location/Qualifiers
REGION                  1..6
                        note = Synthetic
source                  1..6
                        mol_type = protein
                        organism = synthetic construct
SEQUENCE: 160
PAWFGY                                                              6

SEQ ID NO: 161          moltype = AA  length = 8
FEATURE                 Location/Qualifiers
REGION                  1..8
                        note = Synthetic
source                  1..8
                        mol_type = protein
                        organism = synthetic construct
SEQUENCE: 161
LLPAWFGY                                                            8

SEQ ID NO: 162          moltype = AA  length = 7
FEATURE                 Location/Qualifiers
REGION                  1..7
                        note = Synthetic
source                  1..7
                        mol_type = protein
                        organism = synthetic construct
SEQUENCE: 162
LLPAWFG                                                             7

SEQ ID NO: 163          moltype = AA  length = 11
FEATURE                 Location/Qualifiers
REGION                  1..11
                        note = Synthetic
source                  1..11
                        mol_type = protein
                        organism = synthetic construct
SEQUENCE: 163
RASQEISGYL S                                                        11

SEQ ID NO: 164          moltype = AA  length = 6
FEATURE                 Location/Qualifiers
REGION                  1..6
                        note = Synthetic
source                  1..6
                        mol_type = protein
                        organism = synthetic construct
SEQUENCE: 164
QEISGY                                                              6

SEQ ID NO: 165          moltype = AA  length = 7
FEATURE                 Location/Qualifiers
REGION                  1..7
                        note = Synthetic
source                  1..7
                        mol_type = protein
                        organism = synthetic construct
SEQUENCE: 165
SGYLSWL                                                             7

SEQ ID NO: 166          moltype = AA  length = 7
FEATURE                 Location/Qualifiers
REGION                  1..7
                        note = Synthetic
source                  1..7
```

```
                        mol_type = protein
                        organism = synthetic construct
SEQUENCE: 166
AASTLDS                                                                7

SEQ ID NO: 167          moltype =   length =
SEQUENCE: 167
000

SEQ ID NO: 168          moltype = AA  length = 8
FEATURE                 Location/Qualifiers
REGION                  1..8
                        note = Synthetic
source                  1..8
                        mol_type = protein
                        organism = synthetic construct
SEQUENCE: 168
YAASTLDS                                                               8

SEQ ID NO: 169          moltype = AA  length = 10
FEATURE                 Location/Qualifiers
REGION                  1..10
                        note = Synthetic
source                  1..10
                        mol_type = protein
                        organism = synthetic construct
SEQUENCE: 169
RLIYAASTLD                                                             10

SEQ ID NO: 170          moltype = AA  length = 9
FEATURE                 Location/Qualifiers
REGION                  1..9
                        note = Synthetic
source                  1..9
                        mol_type = protein
                        organism = synthetic construct
SEQUENCE: 170
LQYATYPFT                                                              9

SEQ ID NO: 171          moltype = AA  length = 8
FEATURE                 Location/Qualifiers
REGION                  1..8
                        note = Synthetic
source                  1..8
                        mol_type = protein
                        organism = synthetic construct
SEQUENCE: 171
LQYATYPF                                                               8

SEQ ID NO: 172          moltype = AA  length = 115
FEATURE                 Location/Qualifiers
REGION                  1..115
                        note = Synthetic
source                  1..115
                        mol_type = protein
                        organism = synthetic construct
SEQUENCE: 172
QVQLVQSGAE VKKPGASVKV SCKASGYTFT TYWMHWVRQA PGQGLEWMGE IDPSDSYTTY  60
NQKFTGRVTM TRDTSTSTVY MELSSLRSED TAVYYCLLPA WFGYWGQGTL VTVSS       115

SEQ ID NO: 173          moltype = AA  length = 115
FEATURE                 Location/Qualifiers
REGION                  1..115
                        note = Synthetic
source                  1..115
                        mol_type = protein
                        organism = synthetic construct
SEQUENCE: 173
QVQLVQSGAE VKKPGASVKV SCKASGYTFT TYWMHWVRQA PGQGLEWMGE IDPSDSYTTY  60
NQKFTGRVTM TVDTSTSTVY MELSSLRSED TAVYYCLLPA WFGYWGQGTL VTVSS       115

SEQ ID NO: 174          moltype = AA  length = 115
FEATURE                 Location/Qualifiers
REGION                  1..115
                        note = Synthetic
source                  1..115
                        mol_type = protein
                        organism = synthetic construct
SEQUENCE: 174
```

```
QVQLVQSGAE VKKPGASVKV SCKASGYTFT TYWMHWVRQA PGQGLEWMGE IDPSDSYTTY  60
NQKFTGRVTM TRDTSTSTAY MELSSLRSED TAVYYCLLPA WFGYWGQGTL VTVSS       115

SEQ ID NO: 175         moltype = AA  length = 115
FEATURE                Location/Qualifiers
REGION                 1..115
                       note = Synthetic
source                 1..115
                       mol_type = protein
                       organism = synthetic construct
SEQUENCE: 175
QVQLVQSGAE VKKPGASVKV SCKASGYTFT TYWMHWVRQA PGQGLEWMGE IDPSDSYTTY  60
NQKFTGRVTM TRDTSTSTVY MELSSLRSED TAVYFCLLPA WFGYWGQGTL VTVSS       115

SEQ ID NO: 176         moltype = AA  length = 115
FEATURE                Location/Qualifiers
REGION                 1..115
                       note = Synthetic
source                 1..115
                       mol_type = protein
                       organism = synthetic construct
SEQUENCE: 176
QVQLVQSGAE VKKPGASVKV SCKASGYTFT TYWMHWVRQA PGQGLEWMGE IDPSDSYTTY  60
NQKFTGRVTM TVDTSTSTVY MELSSLRSED TAVYFCLLPA WFGYWGQGTL VTVSS       115

SEQ ID NO: 177         moltype = AA  length = 115
FEATURE                Location/Qualifiers
REGION                 1..115
                       note = Synthetic
source                 1..115
                       mol_type = protein
                       organism = synthetic construct
SEQUENCE: 177
QVQLVQSGAE VKKPGASVKV SCKASGYTFT TYWMHWVRQA PGQGLEWMGE IDPSDSYTTY  60
NQKFTGRVTM TRDTSTSTAY MELSSLRSED TAVYFCLLPA WFGYWGQGTL VTVSS       115

SEQ ID NO: 178         moltype = AA  length = 115
FEATURE                Location/Qualifiers
REGION                 1..115
                       note = Synthetic
source                 1..115
                       mol_type = protein
                       organism = synthetic construct
SEQUENCE: 178
QVQLVQSGAE VKKPGASVKV SCKASGYTFT TYWMHWVRQA PGQGLEWMGE IDPSDSYTTY  60
NQKFTGRVTM TVDTSTSTAY MELSSLRSED TAVYFCLLPA WFGYWGQGTL VTVSS       115

SEQ ID NO: 179         moltype = AA  length = 115
FEATURE                Location/Qualifiers
REGION                 1..115
                       note = Synthetic
source                 1..115
                       mol_type = protein
                       organism = synthetic construct
SEQUENCE: 179
QVQLVQSGAE VKKPGASVKV SCKASGYTFT TYWMHWVRQA PGQGLEWIGE IDPSDSYTTY  60
NQKFTGRVTM TVDTSTSTAY MELSSLRSED TAVYFCLLPA WFGYWGQGTL VTVSS       115

SEQ ID NO: 180         moltype = AA  length = 115
FEATURE                Location/Qualifiers
REGION                 1..115
                       note = Synthetic
source                 1..115
                       mol_type = protein
                       organism = synthetic construct
SEQUENCE: 180
QVQLVQSGAE VKKPGASVKV SCKASGYTFT TYWMHWVRQA PGQGLEWMGE IDPSDSYTTY  60
NQKFTGRVTL TVDTSTSTAY MELSSLRSED TAVYFCLLPA WFGYWGQGTL VTVSS       115

SEQ ID NO: 181         moltype = AA  length = 115
FEATURE                Location/Qualifiers
REGION                 1..115
                       note = Synthetic
source                 1..115
                       mol_type = protein
                       organism = synthetic construct
SEQUENCE: 181
QVQLVQSGAE VKKPGASVKV SCKASGYTFT TYWMHWVRQA PGQGLEWIGE IDPSDSYTTY  60
NQKFTGRVTL TVDTSTSTAY MELSSLRSED TAVYFCLLPA WFGYWGQGTL VTVSS       115
```

```
SEQ ID NO: 182          moltype = AA  length = 115
FEATURE                 Location/Qualifiers
REGION                  1..115
                        note = Synthetic
source                  1..115
                        mol_type = protein
                        organism = synthetic construct
SEQUENCE: 182
QVQLVQSGAE VKKPGASVKL SCKASGYTFT TYWMHWVRQA PGQGLEWIGE IDPSDSYTTY  60
NQKFTGRVTL TVDTSTSTAY MELSSLRSED TAVYFCLLPA WFGYWGQGTL VTVSS       115

SEQ ID NO: 183          moltype = AA  length = 107
FEATURE                 Location/Qualifiers
REGION                  1..107
                        note = Synthetic
source                  1..107
                        mol_type = protein
                        organism = synthetic construct
SEQUENCE: 183
DIQMTQSPSS LSASVGDRVT ITCRASQEIS GYLSWYQQKP EKAPKSLIYA ASTLDSGVPS  60
RFSGSGSGTD FTLTISSLQP EDFATYYCLQ YATYPFTFGQ GTKLEIK                107

SEQ ID NO: 184          moltype = AA  length = 107
FEATURE                 Location/Qualifiers
REGION                  1..107
                        note = Synthetic
source                  1..107
                        mol_type = protein
                        organism = synthetic construct
SEQUENCE: 184
DIQMTQSPSS LSASVGDRVT ITCRASQEIS GYLSWYQQKP EKAPKRLIYA ASTLDSGVPS  60
RFSGSGSGTD FTLTISSLQP EDFATYYCLQ YATYPFTFGQ GTKLEIK                107

SEQ ID NO: 185          moltype = AA  length = 107
FEATURE                 Location/Qualifiers
REGION                  1..107
                        note = Synthetic
source                  1..107
                        mol_type = protein
                        organism = synthetic construct
SEQUENCE: 185
DIQMTQSPSS LSASVGDRVT ITCRASQEIS GYLSWLQQKP EKAPKRLIYA ASTLDSGVPS  60
RFSGSGSGTD FTLTISSLQP EDFATYYCLQ YATYPFTFGQ GTKLEIK                107

SEQ ID NO: 186          moltype = AA  length = 107
FEATURE                 Location/Qualifiers
REGION                  1..107
                        note = Synthetic
source                  1..107
                        mol_type = protein
                        organism = synthetic construct
SEQUENCE: 186
DIQMTQSPSS LSASVGDRVT ITCRASQEIS GYLSWLQQKP EKAPKRLIYA ASTLDSGVPS  60
RFSGSRSGTD FTLTISSLQP EDFATYYCLQ YATYPFTFGQ GTKLEIK                107

SEQ ID NO: 187          moltype = AA  length = 107
FEATURE                 Location/Qualifiers
REGION                  1..107
                        note = Synthetic
source                  1..107
                        mol_type = protein
                        organism = synthetic construct
SEQUENCE: 187
DIQMTQSPSS LSASVGDRVT ITCRASQEIS GYLSWLQQKP EKAPKRLIYA ASTLDSGVPS  60
RFSGSGSGTD YTLTISSLQP EDFATYYCLQ YATYPFTFGQ GTKLEIK                107

SEQ ID NO: 188          moltype = AA  length = 107
FEATURE                 Location/Qualifiers
REGION                  1..107
                        note = Synthetic
source                  1..107
                        mol_type = protein
                        organism = synthetic construct
SEQUENCE: 188
DIQMTQSPSS LSASVGDRVT ITCRASQEIS GYLSWLQQKP EKAPKRLIYA ASTLDSGVPS  60
RFSGSRSGTD YTLTISSLQP EDFATYYCLQ YATYPFTFGQ GTKLEIK                107

SEQ ID NO: 189          moltype = AA  length = 107
```

```
FEATURE                 Location/Qualifiers
REGION                  1..107
                        note = Synthetic
source                  1..107
                        mol_type = protein
                        organism = synthetic construct
SEQUENCE: 189
DIQMTQSPSS LSASVGDRVT ITCRASQEIS GYLSWLQQKP EKTPKRLIYA ASTLDSGVPS  60
RFSGSRSGTD YTLTISSLQP EDFATYYCLQ YATYPFTFGQ GTKLEIK                107

SEQ ID NO: 190          moltype = AA  length = 107
FEATURE                 Location/Qualifiers
REGION                  1..107
                        note = Synthetic
source                  1..107
                        mol_type = protein
                        organism = synthetic construct
SEQUENCE: 190
DIQMTQSPSS LSASVGDRVT ITCRASQEIS GYLSWLQQKP EKAPKRLIYA ASTLDSGVPS  60
RFSGSRSGSD YTLTISSLQP EDFATYYCLQ YATYPFTFGQ GTKLEIK                107

SEQ ID NO: 191          moltype = AA  length = 107
FEATURE                 Location/Qualifiers
REGION                  1..107
                        note = Synthetic
source                  1..107
                        mol_type = protein
                        organism = synthetic construct
SEQUENCE: 191
DIQMTQSPSS LSASVGDRVT ITCRASQEIS GYLSWLQQKP EKTPKRLIYA ASTLDSGVPS  60
RFSGSRSGSD YTLTISSLQP EDFATYYCLQ YATYPFTFGQ GTKLEIK                107

SEQ ID NO: 192          moltype = AA  length = 107
FEATURE                 Location/Qualifiers
REGION                  1..107
                        note = Synthetic
source                  1..107
                        mol_type = protein
                        organism = synthetic construct
SEQUENCE: 192
DIQMTQSPSS LSASVGDRVT LTCRASQEIS GYLSWLQQKP EKTPKRLIYA ASTLDSGVPS  60
RFSGSRSGSD YTLTISSLQP EDFATYYCLQ YATYPFTFGQ GTKLEIK                107

SEQ ID NO: 193          moltype = AA  length = 115
FEATURE                 Location/Qualifiers
REGION                  1..115
                        note = Synthetic
source                  1..115
                        mol_type = protein
                        organism = synthetic construct
SEQUENCE: 193
QVQLVQSGAE VKKPGASVKV SCKASGYTFT TYWMHWVRQA PGQGLEWMGE IDPSDSYTTY  60
NQKFTGRVTM TVDTSTSTAY MELSSLRSED TAVYYCLLPA WFGYWGQGTL VTVSS       115

SEQ ID NO: 194          moltype = AA  length = 107
FEATURE                 Location/Qualifiers
REGION                  1..107
                        note = Synthetic
source                  1..107
                        mol_type = protein
                        organism = synthetic construct
SEQUENCE: 194
DIQMTQSPSS LSASVGDRVT ITCRASQEIS GYLSWLQQKP EKAPKSLIYA ASTLDSGVPS  60
RFSGSRSGTD FTLTISSLQP EDFATYYCLQ YATYPFTFGQ GTKLEIK                107

SEQ ID NO: 195          moltype = AA  length = 107
FEATURE                 Location/Qualifiers
REGION                  1..107
                        note = Synthetic
source                  1..107
                        mol_type = protein
                        organism = synthetic construct
SEQUENCE: 195
DIQMTQSPSS LSASVGDRVT ITCRASQEIS GYLSWLQQKP EKAPKSLIYA ASTLDSGVPS  60
RFSGSRSGTD YTLTISSLQP EDFATYYCLQ YATYPFTFGQ GTKLEIK                107

SEQ ID NO: 196          moltype = AA  length = 115
FEATURE                 Location/Qualifiers
REGION                  1..115
```

-continued

```
                        note = Synthetic
source                  1..115
                        mol_type = protein
                        organism = synthetic construct
SEQUENCE: 196
QVQLVQSGAE VKKPGASVKV SCKASGYTFT TYWMHWVRQA PGQGLEWMGE IDPSDSYTTY  60
NQKFTGRVTL TVDTSTSTAY MELSSLRSED TAVYYCLLPA WFGYWGQGTL VTVSS       115

SEQ ID NO: 197          moltype = AA  length = 115
FEATURE                 Location/Qualifiers
REGION                  1..115
                        note = Synthetic
source                  1..115
                        mol_type = protein
                        organism = synthetic construct
SEQUENCE: 197
QVQLVQSGAE VKKPGASVKV SCKASGYTFT TYWMHWVRQA PGQGLEWMGE IDPSDSYTTY  60
NQKFTGRVTL TVDTSTSTVY MELSSLRSED TAVYYCLLPA WFGYWGQGTL VTVSS       115

SEQ ID NO: 198          moltype = AA  length = 1070
FEATURE                 Location/Qualifiers
SITE                    1..1070
                        note = Human PTK7
source                  1..1070
                        mol_type = protein
                        organism = Homo sapiens
SEQUENCE: 198
MGAARGSPAR PRRLPLLSVL LLPLLGGTQT AIVFIKQPSS QDALQGRRAL LRCEVEAPGP  60
VHVYWLLDGA PVQDTERRFA QGSSLSFAAV DRLQDSGTFQ CVARDDVTGE EARSANASFN  120
IKWIEAGPVV LKHPASEAEI QPQTQVTLRC HIDGHPRPTY QWFRDGTPLS DGQSNHTVSS  180
KERNLTLRPA GPEHSGLYSC CAHSAFGQAC SSQNFTLSIA DESFARVVLA PQDVVVARYE  240
EAMFHCQFSA QPPPSLQWLF EDETPITNRS RPPHLRRATV FANGSLLLTQ VRPRNAGIYR  300
CIGQGQRGPP IILEATLHLA EIEDMPLFEP RVFTAGSEER VTCLPPKGLP EPSVWWEHAG  360
VRLPTHGRVY QKGHELVLAN IAESDAGVYT CHAANLAGQR RQDVNITVAT VPSWLKKPQD  420
SQLEEGKPGY LDCLTQATPK PTVVWYRNQM LISEDSRFEV FKNGTLRINS VEVYDGTWYR  480
CMSSTPAGSI EAQARVQVLE KLKFTPPPQP QQCMEFDKEA TVPCSATGRE KPTIKWERAD  540
GSSLPEWVTD NAGTLHFARV TRDDAGNYTC IASNGPQGQI RAHVQLTVAV FITFKVEPER  600
TTVYQGHTAL LQCEAQGDPK PLIQWKGKDR ILDPTKLGPR MHIFQNGSLV IHDVAPEDSG  660
RYTCIAGNSC NIKHTEAPLY VVDKPVPEES EGPGSPPPYK MIQTIGLSVG AAVAYIIAVL  720
GLMFYCKKRC KAKRLQKQPE GEEPEMECLN GGPLQNGQPS AEIQEEVALT SLGSGPAATN  780
KRHSTSDKMH FPRSSLQPIT TLGKSEFGEV FLAKAQGLEE GVAETLVLVK SLQSKDEQQQ  840
LDFRRELEMF GKLNHANVVR LLGLCREAEP HYMVLEYVDL GDLKQFLRIS KSKDEKLKSQ  900
PLSTKQKVAL CTQVALGMEH LSNNRFVHKD LAARNCLVSA QRQVKVSALG LSKDVYNSEY  960
YHFRQAWVPL RWMSPEAILE GDFSTKSDVW AFGVLMWEVF THGEMPHGGQ ADDEVLADLQ  1020
AGKARLPQPE GCPSKLYRLM QRCWALSPKD RPSFSEIASA LGDSTVDSKP             1070

SEQ ID NO: 199          moltype = AA  length = 107
FEATURE                 Location/Qualifiers
SITE                    1..107
                        note = Human Light Chain Constant Region
source                  1..107
                        mol_type = protein
                        organism = Homo sapiens
SEQUENCE: 199
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 200          moltype = AA  length = 330
FEATURE                 Location/Qualifiers
SITE                    1..330
                        note = Human Heavy Chain Constant Region
source                  1..330
                        mol_type = protein
                        organism = Homo sapiens
SEQUENCE: 200
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 201          moltype = AA  length = 330
FEATURE                 Location/Qualifiers
SITE                    1..330
                        note = Human Effectorless Heavy Chain Constant Region
source                  1..330
                        mol_type = protein
                        organism = Homo sapiens
```

```
SEQUENCE: 201
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LAAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 202          moltype = AA  length = 5
FEATURE                 Location/Qualifiers
REGION                  1..5
                        note = Synthetic
source                  1..5
                        mol_type = protein
                        organism = synthetic construct
SEQUENCE: 202
RFTMN                                                             5

SEQ ID NO: 203          moltype = AA  length = 7
FEATURE                 Location/Qualifiers
REGION                  1..7
                        note = Synthetic
source                  1..7
                        mol_type = protein
                        organism = synthetic construct
SEQUENCE: 203
GFTFSRF                                                           7

SEQ ID NO: 204          moltype = AA  length = 8
FEATURE                 Location/Qualifiers
REGION                  1..8
                        note = Synthetic
source                  1..8
                        mol_type = protein
                        organism = synthetic construct
SEQUENCE: 204
GFTFSRFT                                                          8

SEQ ID NO: 205          moltype = AA  length = 13
FEATURE                 Location/Qualifiers
REGION                  1..13
                        note = Synthetic
source                  1..13
                        mol_type = protein
                        organism = synthetic construct
SEQUENCE: 205
VVSGFTFSRF TMN                                                    13

SEQ ID NO: 206          moltype = AA  length = 6
FEATURE                 Location/Qualifiers
REGION                  1..6
                        note = Synthetic
source                  1..6
                        mol_type = protein
                        organism = synthetic construct
SEQUENCE: 206
SRFTMN                                                            6

SEQ ID NO: 207          moltype = AA  length = 17
FEATURE                 Location/Qualifiers
REGION                  1..17
                        note = Synthetic
source                  1..17
                        mol_type = protein
                        organism = synthetic construct
SEQUENCE: 207
SISSTSSYVY YGDSVKG                                                17

SEQ ID NO: 208          moltype = AA  length = 6
FEATURE                 Location/Qualifiers
REGION                  1..6
                        note = Synthetic
source                  1..6
                        mol_type = protein
                        organism = synthetic construct
SEQUENCE: 208
SSTSSY                                                            6

SEQ ID NO: 209          moltype = AA  length = 8
```

```
FEATURE                 Location/Qualifiers
REGION                  1..8
                        note = Synthetic
source                  1..8
                        mol_type = protein
                        organism = synthetic construct
SEQUENCE: 209
ISSTSSYV                                                                  8

SEQ ID NO: 210          moltype = AA  length = 10
FEATURE                 Location/Qualifiers
REGION                  1..10
                        note = Synthetic
source                  1..10
                        mol_type = protein
                        organism = synthetic construct
SEQUENCE: 210
SISSTSSYVY                                                                10

SEQ ID NO: 211          moltype = AA  length = 13
FEATURE                 Location/Qualifiers
REGION                  1..13
                        note = Synthetic
source                  1..13
                        mol_type = protein
                        organism = synthetic construct
SEQUENCE: 211
WVSSISSTSS YVY                                                            13

SEQ ID NO: 212          moltype = AA  length = 16
FEATURE                 Location/Qualifiers
REGION                  1..16
                        note = Synthetic
source                  1..16
                        mol_type = protein
                        organism = synthetic construct
SEQUENCE: 212
EGGDWNYDYN YYYMDV                                                         16

SEQ ID NO: 213          moltype = AA  length = 18
FEATURE                 Location/Qualifiers
REGION                  1..18
                        note = Synthetic
source                  1..18
                        mol_type = protein
                        organism = synthetic construct
SEQUENCE: 213
AREGGDWNYD YNYYYMDV                                                       18

SEQ ID NO: 214          moltype = AA  length = 17
FEATURE                 Location/Qualifiers
REGION                  1..17
                        note = Synthetic
source                  1..17
                        mol_type = protein
                        organism = synthetic construct
SEQUENCE: 214
AREGGDWNYD YNYYYMD                                                        17

SEQ ID NO: 215          moltype = AA  length = 17
FEATURE                 Location/Qualifiers
REGION                  1..17
                        note = Synthetic
source                  1..17
                        mol_type = protein
                        organism = synthetic construct
SEQUENCE: 215
KSSQNVLYNS NNKNYLA                                                        17

SEQ ID NO: 216          moltype = AA  length = 12
FEATURE                 Location/Qualifiers
REGION                  1..12
                        note = Synthetic
source                  1..12
                        mol_type = protein
                        organism = synthetic construct
SEQUENCE: 216
QNVLYNSNNK NY                                                             12
```

```
SEQ ID NO: 217          moltype = AA  length = 7
FEATURE                 Location/Qualifiers
REGION                  1..7
                        note = Synthetic
source                  1..7
                        mol_type = protein
                        organism = synthetic construct
SEQUENCE: 217
KNYLAWY                                                            7

SEQ ID NO: 218          moltype = AA  length = 7
FEATURE                 Location/Qualifiers
REGION                  1..7
                        note = Synthetic
source                  1..7
                        mol_type = protein
                        organism = synthetic construct
SEQUENCE: 218
WASTRES                                                            7

SEQ ID NO: 219          moltype =   length =
SEQUENCE: 219
000

SEQ ID NO: 220          moltype = AA  length = 8
FEATURE                 Location/Qualifiers
REGION                  1..8
                        note = Synthetic
source                  1..8
                        mol_type = protein
                        organism = synthetic construct
SEQUENCE: 220
YWASTRES                                                           8

SEQ ID NO: 221          moltype = AA  length = 10
FEATURE                 Location/Qualifiers
REGION                  1..10
                        note = Synthetic
source                  1..10
                        mol_type = protein
                        organism = synthetic construct
SEQUENCE: 221
LLIYWASTRE                                                         10

SEQ ID NO: 222          moltype = AA  length = 9
FEATURE                 Location/Qualifiers
REGION                  1..9
                        note = Synthetic
source                  1..9
                        mol_type = protein
                        organism = synthetic construct
SEQUENCE: 222
QQYYSTPYT                                                          9

SEQ ID NO: 223          moltype = AA  length = 8
FEATURE                 Location/Qualifiers
REGION                  1..8
                        note = Synthetic
source                  1..8
                        mol_type = protein
                        organism = synthetic construct
SEQUENCE: 223
QQYYSTPY                                                           8

SEQ ID NO: 224          moltype = AA  length = 5
FEATURE                 Location/Qualifiers
REGION                  1..5
                        note = Synthetic
source                  1..5
                        mol_type = protein
                        organism = synthetic construct
SEQUENCE: 224
SYDMH                                                              5

SEQ ID NO: 225          moltype = AA  length = 7
FEATURE                 Location/Qualifiers
REGION                  1..7
                        note = Synthetic
source                  1..7
```

```
                        mol_type = protein
                        organism = synthetic construct
SEQUENCE: 225
GFTFSSY                                                     7

SEQ ID NO: 226          moltype = AA  length = 8
FEATURE                 Location/Qualifiers
REGION                  1..8
                        note = Synthetic
source                  1..8
                        mol_type = protein
                        organism = synthetic construct
SEQUENCE: 226
GFTFSSYD                                                    8

SEQ ID NO: 227          moltype = AA  length = 13
FEATURE                 Location/Qualifiers
REGION                  1..13
                        note = Synthetic
source                  1..13
                        mol_type = protein
                        organism = synthetic construct
SEQUENCE: 227
AASGFTFSSY DMH                                              13

SEQ ID NO: 228          moltype = AA  length = 6
FEATURE                 Location/Qualifiers
REGION                  1..6
                        note = Synthetic
source                  1..6
                        mol_type = protein
                        organism = synthetic construct
SEQUENCE: 228
SSYDMH                                                      6

SEQ ID NO: 229          moltype = AA  length = 16
FEATURE                 Location/Qualifiers
REGION                  1..16
                        note = Synthetic
source                  1..16
                        mol_type = protein
                        organism = synthetic construct
SEQUENCE: 229
GINTDGDTFY PGSVKG                                           16

SEQ ID NO: 230          moltype = AA  length = 5
FEATURE                 Location/Qualifiers
REGION                  1..5
                        note = Synthetic
source                  1..5
                        mol_type = protein
                        organism = synthetic construct
SEQUENCE: 230
NTDGD                                                       5

SEQ ID NO: 231          moltype = AA  length = 7
FEATURE                 Location/Qualifiers
REGION                  1..7
                        note = Synthetic
source                  1..7
                        mol_type = protein
                        organism = synthetic construct
SEQUENCE: 231
INTDGDT                                                     7

SEQ ID NO: 232          moltype = AA  length = 9
FEATURE                 Location/Qualifiers
REGION                  1..9
                        note = Synthetic
source                  1..9
                        mol_type = protein
                        organism = synthetic construct
SEQUENCE: 232
GINTDGDTF                                                   9

SEQ ID NO: 233          moltype = AA  length = 12
FEATURE                 Location/Qualifiers
REGION                  1..12
                        note = Synthetic
```

```
source                  1..12
                        mol_type = protein
                        organism = synthetic construct
SEQUENCE: 233
WVSGINTDGD TF                                                          12

SEQ ID NO: 234          moltype = AA  length = 9
FEATURE                 Location/Qualifiers
REGION                  1..9
                        note = Synthetic
source                  1..9
                        mol_type = protein
                        organism = synthetic construct
SEQUENCE: 234
RGWNYGFDY                                                              9

SEQ ID NO: 235          moltype = AA  length = 11
FEATURE                 Location/Qualifiers
REGION                  1..11
                        note = Synthetic
source                  1..11
                        mol_type = protein
                        organism = synthetic construct
SEQUENCE: 235
ARRGWNYGFD Y                                                           11

SEQ ID NO: 236          moltype = AA  length = 10
FEATURE                 Location/Qualifiers
REGION                  1..10
                        note = Synthetic
source                  1..10
                        mol_type = protein
                        organism = synthetic construct
SEQUENCE: 236
ARRGWNYGFD                                                             10

SEQ ID NO: 237          moltype = AA  length = 11
FEATURE                 Location/Qualifiers
REGION                  1..11
                        note = Synthetic
source                  1..11
                        mol_type = protein
                        organism = synthetic construct
SEQUENCE: 237
QASQDIRNYL N                                                           11

SEQ ID NO: 238          moltype = AA  length = 6
FEATURE                 Location/Qualifiers
REGION                  1..6
                        note = Synthetic
source                  1..6
                        mol_type = protein
                        organism = synthetic construct
SEQUENCE: 238
QDIRNY                                                                 6

SEQ ID NO: 239          moltype = AA  length = 7
FEATURE                 Location/Qualifiers
REGION                  1..7
                        note = Synthetic
source                  1..7
                        mol_type = protein
                        organism = synthetic construct
SEQUENCE: 239
RNYLNWY                                                                7

SEQ ID NO: 240          moltype = AA  length = 7
FEATURE                 Location/Qualifiers
REGION                  1..7
                        note = Synthetic
source                  1..7
                        mol_type = protein
                        organism = synthetic construct
SEQUENCE: 240
DASNLET                                                                7

SEQ ID NO: 241          moltype =   length =
SEQUENCE: 241
000
```

-continued

```
SEQ ID NO: 242          moltype = AA  length = 8
FEATURE                 Location/Qualifiers
REGION                  1..8
                        note = Synthetic
source                  1..8
                        mol_type = protein
                        organism = synthetic construct
SEQUENCE: 242
YDASNLET                                                        8

SEQ ID NO: 243          moltype = AA  length = 10
FEATURE                 Location/Qualifiers
REGION                  1..10
                        note = Synthetic
source                  1..10
                        mol_type = protein
                        organism = synthetic construct
SEQUENCE: 243
LLIYDASNLE                                                      10

SEQ ID NO: 244          moltype = AA  length = 9
FEATURE                 Location/Qualifiers
REGION                  1..9
                        note = Synthetic
source                  1..9
                        mol_type = protein
                        organism = synthetic construct
SEQUENCE: 244
QPYDNLMYT                                                       9

SEQ ID NO: 245          moltype = AA  length = 8
FEATURE                 Location/Qualifiers
REGION                  1..8
                        note = Synthetic
source                  1..8
                        mol_type = protein
                        organism = synthetic construct
SEQUENCE: 245
QPYDNLMY                                                        8
```

The invention claimed is:

1. An isolated anti-PTK7 antibody or an antigen-binding portion thereof, comprising heavy chain CDR (HCDR) 1-3 and light chain CDR (LCDR) 1-3 comprising SEQ ID NOs: 151, 157, 161, 164, 167, and 170, respectively.

2. The isolated antibody or portion of claim 1, comprising a heavy chain variable domain ($V_H$) and a light chain variable domain ($V_L$) comprising SEQ ID NOs: 76 and 75, respectively.

3. The isolated antibody or portion of claim 1, comprising a $V_H$ comprising SEQ ID NOs: 154, 155, and 161, and a $V_L$ comprising SEQ ID NOs: 163, 166, and 170.

4. The isolated antibody or portion of claim 3, wherein the antibody or portion is humanized.

5. The isolated antibody or portion of claim 4, wherein a) the $V_H$ utilizes framework regions from a human IGHV1-46*01 germline gene;

b) the $V_L$ utilizes framework regions from a human IGKVID-16*01 germline gene; or c) a) and b).

6. The isolated antibody or portion of claim 4, wherein a) the $V_H$ utilizes framework regions from a human IGHV1-46*01 germline gene and comprises one or more back mutations selected from Y91F, R71V, V78A, M48I, M69L, and V20L, wherein the numbering is according to SEQ ID NO:172;

b) the $V_L$ utilizes framework regions from a human IGKVID-16*01 germline gene and comprises one or more back mutations selected from I21L, Y36L, A43T, S46R, G66R, T69S, and F71Y, wherein the numbering is according to SEQ ID NO: 183; or c) a) and b).

7. The isolated antibody or portion of claim 4, wherein a) the $V_H$ comprises any one of SEQ ID NOs: 172-182, 193, 196, and 197, or an amino acid sequence at least 95% identical thereto;

b) the $V_L$ comprises any one of SEQ ID NOs: 183-192, 194, and 195, or an amino acid sequence at least 95% identical thereto; or c) a) and b).

8. The isolated antibody or portion of claim 7, wherein the $V_H$ and the $V_L$ comprise SEQ ID NOs: 193 and 188, respectively.

9. The isolated antibody or portion of claim 7, wherein the $V_H$ and the $V_L$ comprise SEQ ID NOs: 178 and 188, respectively, or SEQ ID NOs: 173 and 188, respectively.

10. The isolated antibody or portion of claim 1, wherein the antibody comprises a human $IgG_1$ constant region.

11. The isolated antibody or portion of claim 1, wherein the antibody comprises a) a human heavy chain constant region that comprises SEQ ID NO:201, with or without the C-terminal lysine;

b) a human light chain constant region that comprises SEQ ID NO:199; or c) a) and b).

12. The isolated antibody or portion of claim 1, wherein the antibody or portion is conjugated to a cytotoxin or a detectable label.

13. A pharmaceutical composition comprising the isolated antibody or portion of claim 1 and a pharmaceutically acceptable excipient.

14. Nucleic acid molecule(s) encoding the isolated antibody or portion of claim 1.

15. Expression vector(s) comprising the nucleic acid molecule(s) of claim 14.

16. A recombinant host cell comprising the expression vector(s) of claim 15.

17. A method of making an anti-PTK7 antibody or an antigen-binding portion thereof, comprising:

culturing the recombinant host cell of claim 16 under conditions that allow expression of the antibody or portion, and isolating the antibody or portion from the cell culture.

18. An isolated anti-PTK7 antibody comprising a heavy chain that comprises the amino acid sequences of SEQ ID NOs:193 and 201, with or without the C-terminal lysine of SEQ ID NO: 201, and a light chain that comprises the amino acid sequences of SEQ ID NOs:188 and 199.

19. The isolated antibody of claim 18, wherein the antibody is conjugated to a cytotoxin or a detectable label.

20. A pharmaceutical composition comprising the isolated antibody of claim 18 and a pharmaceutically acceptable excipient.

21. Nucleic acid molecule(s) encoding the isolated antibody of claim 18.

22. Expression vector(s) comprising the nucleic acid molecule(s) of claim 21.

23. A recombinant host cell comprising the expression vector(s) of claim 22.

24. A method of making an anti-PTK7 antibody, comprising:

culturing the recombinant host cell of claim 23 under conditions that allow expression of the antibody, and isolating the antibody from the cell culture.

25. A method of treating a PTK7-positive cancer in a patient in need thereof, comprising administering to the patient the isolated antibody or portion of claim 1.

26. The method of claim 25, wherein the PTK7-positive cancer is selected from head and neck cancer, non-small cell lung cancer, small-cell lung cancer, breast cancer, cervical cancer, endometrial cancer, ovarian cancer, and sarcoma.

27. A method of treating a PTK7-positive cancer in a patient in need thereof, comprising administering to the patient the isolated antibody of claim 18.

28. The method of claim 27, wherein the PTK7-positive cancer is selected from head and neck cancer, non-small cell lung cancer, small-cell lung cancer, breast cancer, cervical cancer, endometrial cancer, ovarian cancer, and sarcoma.

* * * * *